United States Patent
Ingber et al.

(10) Patent No.: US 11,083,754 B2
(45) Date of Patent: Aug. 10, 2021

(54) METHODS FOR GENERATION OF PODOCYTES FROM PLURIPOTENT STEM CELLS AND CELLS PRODUCED BY THE SAME

(71) Applicant: PRESIDENT AND FELLOWS OF HARVARD COLLEGE, Cambridge, MA (US)

(72) Inventors: Donald E. Ingber, Boston, MA (US); Samira Musah, Malden, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

(21) Appl. No.: 14/950,859

(22) Filed: Nov. 24, 2015

(65) Prior Publication Data
US 2016/0143949 A1    May 26, 2016

Related U.S. Application Data

(60) Provisional application No. 62/084,220, filed on Nov. 25, 2014.

(51) Int. Cl.
*C12N 5/071*  (2010.01)
*A61K 35/22*  (2015.01)
*A61K 35/545* (2015.01)

(52) U.S. Cl.
CPC .......... *A61K 35/22* (2013.01); *C12N 5/0686* (2013.01); *A61K 35/545* (2013.01); *C12N 2501/155* (2013.01); *C12N 2501/16* (2013.01); *C12N 2501/165* (2013.01); *C12N 2501/385* (2013.01); *C12N 2501/415* (2013.01); *C12N 2501/727* (2013.01); *C12N 2506/02* (2013.01); *C12N 2506/45* (2013.01); *C12N 2533/52* (2013.01)

(58) Field of Classification Search
None
See application file for complete search history.

(56) References Cited

U.S. PATENT DOCUMENTS

| 8,647,861 | B2 |  | 2/2014 | Ingber et al. | |
|---|---|---|---|---|---|
| 8,809,302 | B2 | * | 8/2014 | Cohen | A61K 31/137 514/56 |
| 2006/0019326 | A1 | * | 1/2006 | Vacanti | C12Q 1/00 435/18 |
| 2010/0111908 | A1 | * | 5/2010 | Lin | A61K 38/30 424/93.7 |
| 2011/0082563 | A1 | * | 4/2011 | Charest | A61F 2/022 623/23.65 |
| 2011/0250585 | A1 |  | 10/2011 | Ingber et al. | |

FOREIGN PATENT DOCUMENTS

| WO | 2009/102983 A2 | 8/2009 |
|---|---|---|
| WO | 2012/011610 A1 | 1/2012 |
| WO | 2013/094771 A1 | 6/2013 |
| WO | WO2015014731 A1 * | 2/2015 |
| WO | 2015/138032 A2 | 9/2015 |
| WO | 2015/138034 A2 | 9/2015 |

OTHER PUBLICATIONS

Reinecke et al. Cardiogenic Differentiation and Transdifferentiation of Progenitor Cells. Circulation Research, 2008. 103:105801071.*
Bernard et al. Wnt4 Action in Gonadal Development and Sex Determination. The International Journal of Biochemistry & Cell Biology, 2007.*
Shanklan et al. Podocytes in Culture: Past, Present, and Future. Kidney International, 2007. 72:26-36.*
Da Sacco et al. A Novel Source of Cultured Podocytes. Pols One, 2013. 8(12): e81812, 15 pages.*
Humphreys. Kidney Structures Differentiated from Stem Cells. Nature Cell Biology, 2014. 16(1) 19-21.*
Lipsitch et al. Negative Control: A tool for Detecting Confounding and Bias in Observational Studies. Epidemiology, 2010. 21(3):383-388.*
Karihaloo et al. Vascular Endothelial Growth Factor Induces Branching Morphogenesis/Tubulogenesis in Renal Epithelial Cells in a Neuropilin-Dependent Fashion. Molecular and Cellular Biology, 2005. 7441-7448.*
Guan et al. Autocrine VEGF-A System in Podocytes Regulates Podocin and its Interaction with CD2AP. American Journal of Physiology Renal Physiology, 2006. 291:F422-F428.*
Dressler et al., 1993, Nature 362: 65-67.*
Quaggin, 2002, Microscopy Research and Technique 57: 208-211.*
Barisoni et al., 2000, Kidney Int'l 58: 137-143.*
Shankland et al., 2000, Kidney Int'l 58: 674-683.*
Dubiel et al., 2014, Cell Mol Bioeng 7: 243-253.*
Pye et al., 2014, Pharmacol Res 85:45-54.*
Chittiprol et al. Marker Expression, Behaviours, and Responses Vary in Different Lines of Conditionally Immortalized Cultured Podocytes. American Journal of Physiology Renal Physiology, 2011. 301:F660-F671.*
Eyre et al. Statin-Sensitive Endocytosis of Albumin by Glomerular Podocytes. American Journal of Physiology Renal Physiology, 2006. 292:F674-F681.*
Dobrinskikh et al. Human Podocytes Perform Polarized, Caveolae-dependent Albumin Endocytosis. American Journal of Physiology Renal Physiology, 2014. 306:F941-951.*
Friedrich et al. Podocytes Are Sensitive to Fluid Shear Stress In Vitro, American Journal of Physiology, Renal Physiology, 2006. 291: F856-F865.*

(Continued)

*Primary Examiner* — Michael D Burkhart
(74) *Attorney, Agent, or Firm* — Nixon Peabody LLP

(57) ABSTRACT

Embodiments of various aspects described herein relate to methods, kits, and cell culture media for generation of podocytes from pluripotent stem (PS) cells, as well as cells produced by the same, and methods of use.

59 Claims, 16 Drawing Sheets
(12 of 16 Drawing Sheet(s) Filed in Color)

(56) References Cited

OTHER PUBLICATIONS

Lam et al., "Rapid and Efficient Differentiation of Human Pluripotent Stem Cells into Intermediate Mesoderm That Forms Tubules Expressing Kidney Proximal Tubular Markers" J Am Soc Nephrol, 25:1211-25 (2014).

Lian et al., "Efficient differentiation of human pluripotent stem cells to endothelial progenitors via small-molecule activation of WNT signaling", Stem Cell Reports, 3(5):804-16 (2014).

Mae et al., "Monitoring and robust induction of nephrogenic intermediate mesoderm from human pluripotent stem cells", Nat Commun, 4:1367 (2013).

Song et al., "The directed differentiation of human iPS cells into kidney podocytes", PLoS One, 7(9):1-9 (2012).

Takasato et al., "Directing human embryonic stem cell differentiation towards a renal lineage generates a self-organizing kidney." Nature Cell Biology 16(1):118-126 (2014).

* cited by examiner

METHODS FOR GENERATION OF PODOCYTES FROM PLURIPOTENT STEM CELLS AND CELLS PRODUCED BY THE SAME

CROSS-REFERENCE TO RELATED APPLICATIONS

This Application claims benefit under 35 U.S.C. § 119(e) of the U.S. Provisional Application No. 62/084,220 filed Nov. 25, 2014, the contents of which are incorporated herein by reference in their entirety.

GOVERNMENT SUPPORT

The invention was made with Government Support under Contract No. W911NF-12-2-0036 awarded by the Defense Advanced Research Projects Agency (DARPA). The government has certain rights in the invention.

TECHNICAL DISCLOSURE

Embodiments of various aspects described herein relate to methods, kits, and cell culture media for generation of podocytes from pluripotent stem (PS) cells, cells produced by the same, and methods of use.

BACKGROUND

Human pluripotent stem (hPS) cells, which include embryonic (hES) and induced pluripotent stem (iPS) cells, have a remarkable capacity to self-renew indefinitely and differentiate into almost any cell type. As such, hPS cells represent a potentially unlimited supply of tissue/organ-specific cells for disease modeling, drug and toxicity testing, cell-based therapeutics, and understanding human developmental processes. Realizing the full potential of hPS cells hinges on the ability to direct their differentiation into desired cell types, such as podocytes. Podocytes are highly differentiated cells that encase kidney glomerular capillaries and constitute a major portion of the filtration barrier between blood and urinary spaces. Loss or dysfunction of podocytes is a hallmark of progressive kidney or glomerular diseases or disorders resulting in proteinuria and nephron degeneration. The ability to generate podocytes from hPS cells has significant value for developing in vitro models to advance therapeutic discovery and use as cell-based therapeutics for kidney disease and regeneration as well as for elucidating mechanisms of human kidney development and disease progression.

Previous attempts to generate podocytes from hPS cells focused on non-specific differentiation of human iPS cells and are poorly reproducible. Song et al. (2012) *PLoS One* 7, e46453. Therefore, there is no existing method that can direct differentiation of hPS cells into podocytes. Accordingly, there is a need for developing a robust method for directed differentiation of hPS cells into human kidney podocytes.

SUMMARY

Aspects described herein stem from, at least in part, development of novel podocyte induction media and methods that efficiently direct differentiation of pluripotent stem (PS) cells and/or mesodermal cells into podocytes. In particular, the inventors have demonstrated inter alia that a podocyte induction medium comprising activin A, bone morphogenetic protein (BMP), an inhibitor of glycogen synthase kinase 3 (GSK-3) or an activator of Wnt signaling pathway, vascular endothelial growth factor (VEGF), and retinoic acid, efficiently induces differentiation of at least about 93% or more human PS cell (hPS)-derived intermediate mesoderm cells into podocytes within 3-5 days. Unlike pseudo-podocytes generated by existing differentiation methods that exhibit immature phenotype, in some embodiments, hPS cell-derived podocytes formed using the novel podocyte induction media and/or the differentiation methods described herein exhibited mature phenotype, e.g., Pax-2 negative, and minimal or no proliferation capability. The inventors have also demonstrated that mechanical forces and/or shear stress can be used in conjunction with the podocyte induction media described herein to enhance differentiation of hPS cells and their derivatives into podocytes, and/or enhance interaction of differentiated podocytes with endothelial cells or any other cell type, e.g., in a co-culture.

The hPS cell-derived podocytes generated by the methods described herein can be used in various applications, including, e.g., but not limited to, as an in vitro model for a kidney/glomerular disorder, therapeutic applications (e.g., tissue regeneration and/or repair or transplantation), drug discovery and/or developments, and/or tissue engineering. Accordingly, embodiments of various aspects described herein relate to methods, kits, and cell culture media for generation of podocytes from pluripotent stem (PS) cells, cells produced by the same, and methods of use.

Accordingly, some aspects described herein contribute to a strategy to increasing the efficiency of podocyte formation from pluripotent stem (PS) cells. In one aspect, for example, as shown in FIG. 1A or FIG. 3A, the starting porting for such strategy is differentiating the PS cells into mesoderm cells (stage 1 differentiation, e.g., using the first mesoderm differentiation media as described herein), and then differentiating these cells into intermediate mesoderm cells, e.g., using the second mesoderm differentiation media as described herein). This step-wise differentiation strategy can be further expanded to enable efficient differentiation of mesoderm and/or intermediate mesoderm cells into podocytes, e.g., podocytes expressing nephrin and WT-1, but negative for Pax-2, wherein the method comprises contacting the mesodermal cells and/or intermediate mesodermal cells with a medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid.

Various aspects described herein relates to methods for generating a population of podocytes. In one aspect, the method comprises contacting a population of pluripotent stem (PS) cells with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free. The method produces a population of cells that comprises an increased percentage of podocytes, as compared to the pluripotent stem cells not contacted with the podocyte induction medium. In some embodiments, at least about 80% or more of the pluripotent stem cells are differentiated into podocytes.

The PS cells can come from various sources and include, e.g., embryonic stem cells and/or induced pluripotent stem cells.

The pluripotent stem cells can be contacted with the podocyte induction medium for a pre-determined period of time, e.g., until at least a portion of the cells display one or more podocyte-specific marker, or until the cells reach a desirable differentiation stage (e.g., podocyte progenitors, immature podocytes, or mature podocytes), or until the cells differentiate into post-mitotic podocytes. For example, in some embodiments, if the differentiated cells were to be used for transplantation, it can be desirable that the cells are not fully differentiated into post-mitotic podocytes, such that they can integrate better with other cells upon transplantation. Accordingly, the period of time can range from about 1 day to 1 week to 2 weeks or longer. In some embodiments, the period of time can be at least about 3 days or longer. In some embodiments, the period of time can be at least about 5 days or longer. In some embodiments, the period of time can be at least 7 days or longer.

While not necessary, in some embodiments, the PS cells can be cultured under a condition to induce formation of embryoid bodies and/or organoids prior to or during the contact with the podocyte induction medium.

In another aspect, a method of generating a population of podocytes comprises contacting a population of mesodermal cells and/or intermediate mesodermal cells with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free. The method produces a population of cells that comprises an increased percentage of podocytes, as compared to percentages of podocytes differentiated from mesodermal cells and/or intermediate mesodermal cells not contacted with the podocyte induction medium. In some embodiments, at least about 80% or more of the mesodermal cells and/or intermediate mesodermal cells are differentiated into podocytes.

The mesodermal cells or intermediate mesodermal cells can be contacted with the podocyte induction medium for a pre-determined period of time, e.g., until at least a portion of the cells display one or more podocyte-specific marker, or until the cells reach a desirable differentiation stage (e.g., podocyte progenitors, immature podocytes, or mature podocytes), or until the cells differentiate into post-mitotic podocytes. For example, in some embodiments, if the differentiated cells were to be used for transplantation, it can be desirable that the cells are not fully differentiated into post-mitotic podocytes, such that they can integrate better with other cells upon transplantation. Accordingly, the period of time can range from about 1 day to 1 week to 2 weeks or longer. In some embodiments, the period of time can be at least about 1 day, at least about 2 days, at least about 3 days, at least about 4 days, at least about 5 days or longer.

In some embodiments, the mesodermal cells and/or intermediate mesodermal cells can be derived or produced from a population of pluripotent stem cells. For example, as discussed previously, the mesodermal cells can be derived from pluripotent stem (PS) cells by contacting a population of pluripotent stem cells with a serum-free first mesoderm differentiation medium comprising activin A and an inhibitor of glycogen synthase kinase 3 (GSK-3) or an activator of Wnt signaling pathway. In some embodiments, the pluripotent stem cells can be contacted with the first mesoderm differentiation medium for a period of time until at least a portion of the cells display one or more mesodermal cell-specific markers. Non-limiting examples of mesodermal cell-specific markers include Brachyury, Goosecoid, Snail, Twist-1, Twist-2, Wnt-8a, N-Cadherin, MIXL1 (Mix/Bix paired-like homeodomain protein), GDF-1 (Growth/differentiation factors-1), and a combination of two or more thereof. In some embodiments, the period of time can be about 1 day to about 5 days.

In some embodiments, the intermediate mesodermal cells can be produced by contacting mesodermal cells or PS cell-derived mesodermal cells with a serum-free second mesoderm differentiation medium comprising BMP and an inhibitor of glycogen synthase kinase 3 (GSK-3) or an activator of Wnt signaling pathway. In some embodiments, the BMP is BMP-7. In some embodiments, the mesodermal cells are contacted with the second mesoderm differentiation medium for a period of time until at least a portion of the mesodermal cells display one or more intermediate mesodermal cell-specific marker. Non-limiting examples of intermediate mesodermal cell-specific markers include OSR1 (Odd-Skipped Related Transcription Factor 1), Pax2 (Paired Box 2), Pax8 ((Paired Box 8), SIX2 (SIX homeobox 2), WT1 (Wilms tumor 1), Cited2 (Cbp/p300-interacting transactivator, with Glu/Asp-rich carboxy-terminal domain, 2), Eya1 (Eyes absent homolog 1), Sall1 (spalt-like transcription factor 1), and a combination of two or more thereof. In some embodiments, the period of time can be about 5 days or longer.

In another aspect, a method of generating a population of podocytes is provided herein. The method comprises: (a) contacting a population of pluripotent cells with a serum-free first mesoderm differentiation medium comprising activin A and an inhibitor of glycogen synthase kinase 3 (GSK-3) or an activator of Wnt signaling pathway; (b) contacting a population of cells from step (a) with a serum-free second mesoderm differentiation medium comprising BMP and an inhibitor of glycogen synthase kinase 3 (GSK-3) or an activator of Wnt signaling pathway; and (c) contacting a population of cells from step (b) with a serum-free podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid. The method produces a population of cells that comprises an increased percentage of podocytes, as compared to the cells from step (b) not contacted with the podocyte induction medium. In some embodiments, at least about 80% or more of the pluripotent stem cells are differentiated into podocytes.

In some embodiments, the BMP is BMP-7.

In some embodiments, the contact period of time in step (a) can range from about 12 hours to about 10 days, or about 1 day to about 5 days, or about 1 day to about 3 days, or about 1 day to about 2 days.

In some embodiments, the contact period of time in step (b) can range from about 3 days to about 30 days, or about 5 days to about 25 days, or about 10 days to about 20 days, or about 15 days to about 20 days.

In some embodiments, the contact period of time in step (c) can range from about 12 hours to about 20 days, or about 1 day to about 15 days, or about 2 days to about 10 days, or about 3 days to about 5 days.

In some embodiments of this aspect and other aspects described herein, the method can further comprise subjecting the cells to a mechanical strain and/or shear stress. For example, a fluid (e.g., an appropriate medium depending on the stage of the differentiation process) can be continuously flown over the cells at a flow rate that generates a physiologically-relevant shear stress to the cells. In other embodiments, the cells can be periodically stretched or compressed during the differentiation process.

In some embodiments of this aspect and other aspects described herein, the cells to be differentiated can be co-cultured with endothelial cells (e.g., glomerular endothelial cells). In some embodiments, the cells to be differentiated and endothelial cells can be co-cultured in individual chambers separated by a fluid-permeable structure (e.g., a porous membrane). In these embodiments, while not necessary, application of mechanical strain to the cells can enhance extension of podocyte foot processes through the fluid-permeable structure.

In some embodiments of this aspect and other aspects described herein, the GSK-3 inhibitor can be selected from the group consisting of: CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), GSK-3 inhibitor VI (2-Chloro-1-(4,5-dibromo-thiophen-2-yl)-ethanone), GSK-3 inhibitor VII (2,4'-Dibromoacetophenone), GSK-3 inhibitor X (6-Bromoindirubin-3'-acetoxime), GSK-3 inhibitor IX ((2Z, 3E)-6'-Bromo-3-(hydroxyimino)[2,3'-biindolinylidene]-2'-one), GSK-3 inhibitor XII (TWS119; 3-[[6-(3-aminophenyl)-7H-pyrrolo[2,3-d]pyrimidin-4-yl]oxy]-phenol), GSK-3 inhibitor XV (pyridocarbazolo-cyclopentadienyl ruthenium complex), GSK-3 inhibitor XVI (6-(2-(4-(2,4-Dichlorophenyl)-5-(4-methyl-1H-imidazol-2-yl)-pyrimidin-2-ylamino)ethyl-amino)-nicotinonitrile), lithium chloride, valproic acid (2-Propylpentanoic acid), SB216763 (3-(2,4-Dichlorophenyl)-4-(1-methyl-1H-indol-3-yl)-1H-pyrrole-2,5-dione), SB415286 (3-[(3-Chloro-4-hydroxyphenyl)amino]-4-(2-nitrophenyl)-1H-pyrrole-2,5-dione), Indirubin (6-bromoindirubin-3'-[O-(N,N-diethylcarbamyl)-oxime; 6-bromoindirubin-3'-[O-(2-morpholin-1-ylethyl)-oxime]hydrochloride), Kenpaullone (9-Bromo-7,12-dihydroindolo-[3,2-d][1]benzazepin-6(5H)-one), Hymenidin (2-Debromooroidin), a combination of two or more thereof, or variants or derivatives thereof.

In some embodiments of this aspect and other aspects described herein, the activator of Wnt signaling pathway can be selected from the group consisting of Wnt3a, FGF18, beta-catenin, norrin, R-spondin2, and a combination of two or more thereof.

In some embodiments of this aspect and other aspects described herein, the BMP can be any member of BMP family. In some embodiments, the BMP can be BMP-2, BMP-4, BMP-7, or a combination of two or more thereof. In some embodiments, the BMP can be BMP-7.

The concentrations of each individual component in the first mesoderm differentiation medium, the second mesoderm differentiation medium and/or the podocyte induction medium can vary from ng/mL to mg/mL or from nM to µM. In some embodiments of this aspect and other aspects described herein, the concentration of the activin A can range from about 50 ng/mL to about 500 ng/mL.

In some embodiments of this aspect and other aspects described herein, the concentration of the BMP can range from about 50 ng/mL to about 500 ng/mL.

In some embodiments of this aspect and other aspects described herein, the concentration of the inhibitor of GSK-3 or the activator of Wnt signaling pathway can range from about 0.1 µM to about 10 µM.

In some embodiments of this aspect and other aspects described herein, the concentration of the VEGF can range from about 25 ng/mL to about 250 ng/mL.

In some embodiments of this aspect and other aspects described herein, the concentration of the retinoic acid can range from about 0.01 µM to about 1 µM.

Individual components in the first mesoderm differentiation medium, the second mesoderm differentiation medium and/or the podocyte induction medium can each be independently present in solution (e.g., in a soluble form) or be immobilized on a biomaterial substrate in which the cells are cultured. In some embodiments, at least one or more (including, e.g., at least two or more) of the components (i)-(v) (i.e., (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid) in the podocyte induction medium can be immobilized on a biomaterial substrate.

The pluripotent stem cells, mesodermal cells, and/or intermediate mesodermal cells in the methods of various aspects described herein can be cultured in any appropriate mode, including, e.g., adherent cultures (2-dimensional or 3-dimensional), suspension cultures (e.g., non-adherent cultures), scaffold cultures, or a combination of two or more thereof.

In some embodiments of this aspect and other aspects described herein, the pluripotent stem cells, mesodermal cells, and/or intermediate mesodermal cells can be cultured as adherent cells during the contacting step. While not necessary, it can be desirable to have cell culture environment mimic the physiological microenvironment of a kidney or glomerulus, and/or to promote cell adhesion to a substrate surface. Accordingly, in some embodiments, the pluripotent stem cells, mesodermal cells, and/or intermediate mesodermal cells can be cultured on a surface coated with at least one extracellular matrix. Non-limiting examples of extracellular matrix include, but are not limited to, laminin, collagen, fibronectin, vitronectin, hyaluronic acid, peptides, gelatin, matrigel, decellularized matrix, and a combination of two or more thereof. In some embodiments, the pluripotent stem cells, mesodermal cells, and/or intermediate mesodermal cells can be cultured on a surface coated with laminin and/or collagen. In some embodiments, the pluripotent stem cells, mesodermal cells, and/or intermediate mesodermal cells can be cultured on a surface coated with decellularized matrix produced by glomerular endothelial cells.

In some embodiments of this aspect and other aspects described herein, the pluripotent stem cells, mesodermal cells, and/or intermediate mesodermal cells can be cultured suspension or embedded in a biomaterial scaffold during the contacting step.

In some embodiments of the methods described herein where multi-stages of cell cultures are involved, cells in each stage can be independently cultured in the same culture mode (e.g., adherent, suspension, or scaffold), or in different culture modes (e.g., adherent, suspension, or scaffold).

The pluripotent stem cells, mesodermal cells, and/or intermediate mesodermal cells used in the methods of various aspects described herein can be of any species, including, e.g., but not limited to, human cells and animal cells. In some embodiments of this aspect and other aspects described herein, the pluripotent stem cells, mesodermal cells, and/or intermediate mesodermal cells can be human cells.

The methods of various aspects described herein generally can efficiently generate podocytes from the pluripotent stem cells, mesodermal cells and/or intermediate mesodermal cells. For example, the methods of various aspects described herein can induce differentiation of at least about 80% or more (up to 100%) of the pluripotent stem cells, mesodermal cells and/or intermediate mesodermal cells into podocytes. Accordingly, while not necessary, in some embodiments where it is desirable to generate a pure (100%) population of podocytes, the methods of various aspects described herein can further comprise selecting the podocytes upon the contacting step. Cell selection can be performed by any methods known in the art, including, e.g., cell cytometry and/or immunostaining. In some embodiments, the podocytes can be selected by at least one or more of the following criteria:

a. the podocytes are substantially negative for a pluripotency marker;
b. the podocytes are positive (e.g., at or above a threshold level corresponding to the level present in mature podocytes in vivo) for at least one or more podocyte marker;
c. the podocytes have low or substantially no expression of progenitor cell marker; and
d. the podocytes are substantially incapable of proliferation (e.g., are terminally differentiated).

Isolated populations of podocytes produced by the methods of any aspects described herein are also provided. In some embodiments, the podocytes can be post-mitotic (mature) podocytes. In some embodiments, the podocytes can be immature podocytes. In some embodiments, the isolated population of podocytes can comprise at least 80%, at least 90%, at least 95%, or up to 100% of podocytes.

In some embodiments, the podocytes can comprise at least one or more genetic modifications. In some embodiments, the podocytes can be genetically modified or engineered to express at least one or more mesodermal-specific reporters (e.g., but not limited to, fluorescently-labeled Brachyury, Goosecoid, SNAIL, TWIST-1, TWIST-2, WNT-8a, N-Cadherin, MIXL1, or GDF-1); kidney-specific reporters (e.g., but not limited to, fluorescently-labeled Wilm's tumor protein 1 (WT1), GDNF (glial cell derived neurotrophic factor), RET (ret proto-oncogene), WNT4 (wingless-type MMTV integration site family, member 4), CDH16 (cadherin 16, KSP-cadherin), CLCN5 (chloride channel, voltage-sensitive 5), CYP27/CYP27A1 (Cytochrome P450, Family 27, Subfamily A, Polypeptide), or SLC12A1 (solute carrier family 12 (sodium/potassium/chloride transporter), member 1); podocyte-specific reporters (e.g., but not limited to fluorescently-labeled nephrin, Apolipoprotein L1 (APOL1), alpha-actinin 4, podocin, podocalyxin, and synaptopodin), or a combination of two or more thereof. In some embodiments, the podocytes can be genetically modified or engineered to correct or introduce defect(s) or mutation(s) in podocyte genes (e.g., but not limited to nephrin, WT1, APOL1, alpha-actinin 4, podocin, podocalyxin, synaptopodin, and a combination of two or more thereof).

In some embodiments, the podocytes can have a cell size ranging from about 30 μm to about 90 μm, when they are dissociated (e.g., non-adherent) or in a suspension. As the podocytes attach and spread on a surface (e.g., a solid substrate surface with or without extracellular matrix proteins), the cells can be larger in size, e.g., up to about 250 μm or higher.

In some embodiments, the podocytes can exhibit an increased uptake of exogenous albumin, e.g., by at least about 10% or more, as compared to mature podocytes naturally occurring in vivo or immortalized podocytes.

One aspect provided herein relates to a synthetic tissue scaffold comprising a biopolymer and an isolated population of podocytes distributed therein, wherein the isolated population of podocytes is produced by the methods of any aspects described herein.

In some embodiments, the synthetic tissue scaffold can further comprise one or more kidney-associated cells distributed in the biopolymer. Non-limiting examples of kidney-associated cells include, but are not limited to, endothelial cells, mesangial cells, epithelial cells, smooth muscle cells or myocytes, granular cells (Juxtaglomerular cells), parietal cells, proximal tubular cells, loop of Henle thin segment cells, duct cells, connective tissue fibroblasts, pericytes, insulin-producing cells, and a combination of two or more thereof.

Podocytes (e.g., immature or mature) produced by the methods of various aspects described herein can be used in different applications where podocytes are required, including, e.g., but not limited to, as an in vitro model for a kidney/glomerular disorder, therapeutic applications (e.g., tissue regeneration and/or repair or transplantation), drug discovery and/or developments, and/or tissue engineering. In one aspect, a method of modeling a kidney-specific condition in vitro is provided herein. The method comprises culturing in a cell or tissue culture device the isolated population of podocytes described herein. In some embodiments, the podocytes can be post-mitotic podocytes.

The podocytes can be cultured in any cell or tissue culture device selected to suit the need of an application. Examples of a cell or tissue culture device include, but are not limited to, a transwell, a microwell, a microfluidic device, a bioreactor, a culture plate, or any combinations thereof. In some embodiments, the podocytes can be used for 3D printing to generate artificial kidney tissue. In some embodiments, the methods described herein can be performed in a microfluidic device. In one embodiment, the microfluidic device can be an organ-on-a-chip device. In one embodiment, the organ-on-a-chip device can comprise a first channel and a second channel separated by a membrane, where a first surface of the membrane facing the first channel comprises the podocytes adhered thereon. In some embodiments, a second surface of the membrane facing the second channel can comprise kidney capillary endothelial cells or glomerular endothelial cells adhered thereon.

The podocytes can be differentiated from mesoderm and/or intermediate mesoderm cells according to the methods and compositions described herein, and then transferred to a cell or tissue culture device for modeling a kidney-specific condition in vitro, or they can be differentiated in the cell or tissue culture device from pluripotent stem cells, mesodermal cells and/or intermediate mesodermal cells using the differentiation methods of various aspects described herein, prior to the culturing. The pluripotent stem cells, mesodermal cells, and/or intermediate mesodermal cells can be derived from normal, healthy cells or diseased cells. In some embodiments, the diseased cells can be derived from a subject having a kidney and/or glomerular disorder, or a subject with a predisposition (e.g., but not limited to single nucleotide polymorphism) that increases his or her risk of developing a kidney and/or glomerular disorder. Examples of a kidney and/or glomerular disorder include, without limitations, podocyte injury, proteinuria, glomerulosclerosis, diabetic nephropathy, chemotherapy-related nephrotoxicity, and a podocytopathy resulting from one or more mutations in podocyte genes (e.g., genes encoding nephrin, WT1, APOL1, alpha-actinin 4, podocin, podocalyxin, synaptopodin, or a combination of two or more thereof).

In some embodiments where normal, healthy podocytes are used, the podocytes can be contacted with an agent that induces the podocytes to acquire at least one phenotypic characteristic associated with a kidney and/or glomerular disorder, thereby modeling a kidney and/or glomerular disorder in vitro. By way of example only, in some embodiments, doxorubicin and/or Adriamycin can be introduced to induce podocytes injury to model a kidney or glomerulus-specific condition in vitro.

Not only can an in vitro model of a kidney or glomerulus-specific condition (a normal or diseased condition) be used to elucidate mechanisms of kidney development and/or disease progression, but it can also be employed to advance therapeutic discovery. Accordingly, a method of screening for an agent to reduce at least one phenotypic characteristic of podocytes associated with a kidney and/or glomerular disorder is also provided herein. The method comprises (a) culturing the isolated population of podocytes described herein that display at least one phenotypic characteristic associated with the kidney and/or glomerular disorder; (b) contacting the podocytes with a library of candidate agents; and (c) detecting response of the podocytes to the candidate agents to identify an agent based on detection of the presence of a reduction in the phenotypic characteristic of the podocytes associated with the kidney and/or glomerular disorder. The candidate agents can be selected from the group consisting of proteins, peptides, nucleic acids (e.g., but not limited to, siRNA, anti-miRs, antisense oligonucleotides, and ribozymes), small molecules, drugs, and a combination of two or more thereof.

In another aspect, the podocytes generated by the differentiation methods described herein can be used as cell-based therapeutics for treatment of a kidney and/or glomerular disorder (including, e.g., but not limited to, podocyte injury, proteinuria, glomerulosclerosis, diabetic nephropathy, chemotherapy-related nephrotoxicity or combinations thereof. Thus, methods of treating a kidney and/or glomerular disorder are also provided herein. In one embodiment, the method comprises transplanting to a subject in need thereof (e.g., suffering from a kidney and/or glomerular disorder) an isolated population of podocytes generated by the differentiation methods of any aspects described herein or a synthetic tissue scaffold as described herein.

In some embodiments, the podocytes and/or the synthetic tissue scaffold can be transplanted at or in close proximity to a pre-determined location of a kidney of the subject. For example, the podocytes and/or the synthetic tissue scaffold can be transplanted at or in close proximity to a damaged area of a kidney of the subject. The transplanted podocytes can migrate and localize into at least one or more glomerular capillary structure of the kidney tissue.

Podocyte transplantation can be an autologous transplant or an allogeneic transplant. Thus, in some embodiments, the podocytes can be differentiated from pluripotent stem cells derived from somatic cells of the subject to be treated. In other embodiments, the differentiated podocytes can be allogeneic cells.

Kits for generating a population of podocytes are also provided herein. In some embodiments, the kit comprises: (a) a first container comprising activin A and an inhibitor of glycogen synthase kinase 3 (GSK-3) or an activator of Wnt signaling pathway; a second container comprising bone morphogenetic protein (BMP) and an inhibitor of glycogen synthase kinase 3 (GSK-3) or an activator of Wnt signaling pathway; and (c) a third container comprising (i) activin A, (ii) BMP, (iii) an inhibitor of GSK-3 or an activator of Wnt signaling pathway, (iv) vascular endothelial growth factor (VEGF), and (v) retinoic acid, and wherein the first container, the second container and the third container are each serum-free.

In some embodiments, the kit can further comprise a cell culture device. Examples of a cell culture device include, but are not limited to, a transwell, a microwell, a microfluidic device, a bioreactor, a culture plate, or any combinations thereof. In some embodiments, the kit can further comprise a microfluidic device. In some embodiments, the microfluidic device can be an organ-on-a-chip device. In one embodiment, the organ-on-a-chip device can comprise a first channel and a second channel separated by a membrane, where a first surface of the membrane facing the first channel comprises the podocytes adhered thereon. In some embodiments, a second surface of the membrane facing the second channel can comprise kidney capillary endothelial cells or glomerular endothelial cells adhered thereon.

In some embodiments, individual components in the first, second or third container can be in a form of powder, e.g., lyophilized powder. The powder can be reconstituted upon use. In some embodiments, individual components in the first, second or third container can be in a form of liquid.

In some embodiments, the kit can further comprise one or more vials of pluripotent stem cells, mesodermal cells and/or intermediate mesodermal cells. In some embodiments, the cells can be frozen or cryopreserved, or are present in cryopreservation medium.

In some embodiments, the kit can further comprise one or more vials of immortalized podocytes.

In some embodiments, the kit can comprise one or more vials of cryopreserved/frozen podocytes, or podocytes in a cryopreservation medium.

In some embodiments, the kit can further comprise one or more containers each containing a detectable label that specifically binds to a pluripotency marker, a podocyte-specific marker, or a progenitor cell marker.

Yet another aspect described herein is a podocyte induction medium (e.g., powder or liquid) for differentiation of pluripotent stem cells, mesodermal cells and/or intermediate mesodermal cells into podocytes. The podocyte induction medium is serum-free and comprises (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid. In some embodiments, the concentration of the activin A can range from about 50 ng/mL to about 500 ng/mL. In some embodiments, the concentration of the BMP can range from about 50 ng/mL to about 500 ng/mL. In some embodiments, the concentration of the inhibitor of GSK-3 or the activator of Wnt signaling pathway can range from about 0.1 µM to about 10 µM. In some embodiments, the concentration of the VEGF can range from about 25 ng/mL to about 250 ng/mL. In some embodiments, the concentration of the retinoic acid can range from about 0.01 µM to about 1 µM.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) An exemplary schematic timeline for directed differentiation. BMP-7: Bone morphogenetic protein 7; VEGF: Vascular endothelial growth factor; RA: Retinoic acid; PIM: podocyte induction medium. (FIG. 1B) Bright field images of undifferentiated human iPS cells (left), podocytes derived from human iPS cells using the methods described herein (middle), and immortalized human podocyte cell line as positive control (right). (FIG. 1C) Representative fluorescent images showing human iPS cell-derived podocytes immunostained for WT1 (Wilm's tumor protein 1, a marker of kidney cells) and nephrin (podocyte-specific marker). The podocytes were derived from the human iPS cells using the methods described herein.

(FIG. 2A) Flow cytometry analysis for expression of podocyte markers. Immortalized human podocyte cell line was used as positive control. For each plot, x-axis represents the level of WT1 expression and the y-axis represents the expression level of nephrin. (FIG. 2B) Quantification of human iPS cell-derived podocytes indicates upregulation of podocyte markers (WT1 and nephrin), with corresponding decrease in Oct4 pluripotency marker. The decrease in progenitor cell markers (Pax2 and OSR1) and lack of EdU incorporation indicate that the cells are post-mitotic and terminally differentiated, as in mature podocytes.

(FIG. 3A) An exemplary schematic timeline for directed differentiation of human PS cells into podocytes. BMP7: Bone morphogenetic protein 7; VEGF: Vascular endothelial growth factor; RA: Retinoic acid; PIM: Podocyte induction medium. (FIG. 3B) Low magnification (top panel) and high magnification (bottom panel) bright field images of undifferentiated human iPS cells (leftmost column), mesoderm derived from human iPS cells (second column from left), intermediate mesoderm derived from human iPS cells (third column from left), and podocytes (rightmost column) derived from human iPS cells.

Figure 3A:
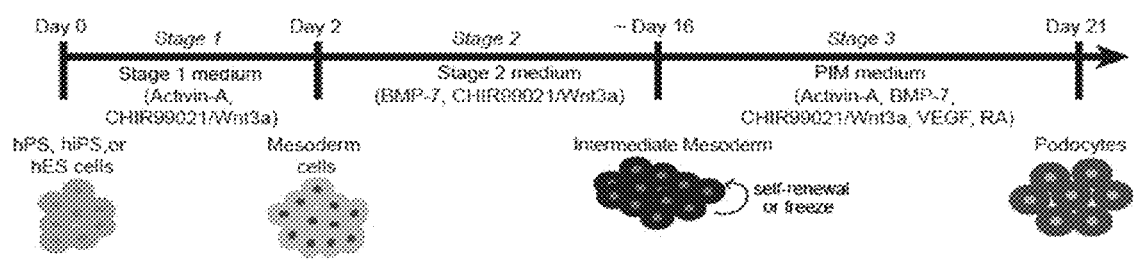
FIGS. 3A-3B show directed differentiation of hPS cells into podocytes according to another embodiment of the methods described herein.

Unless otherwise stated, podocytes as shown in FIGS. 3B-FIG. 13 were derived from human pluripotent stem cells using the method or protocol as illustrated in FIG. 3A.

Figure 4A:
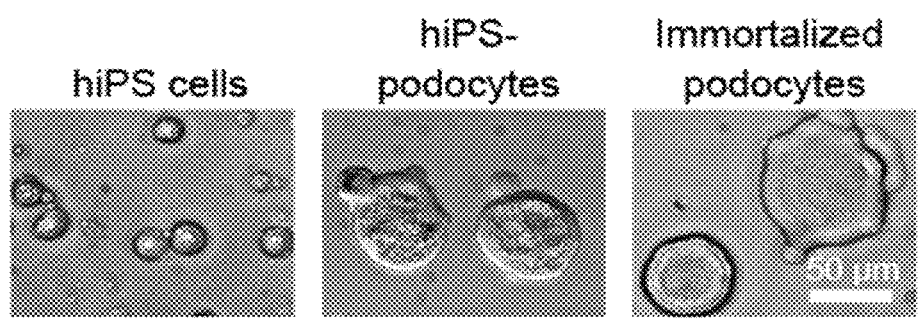
Figure 4B:
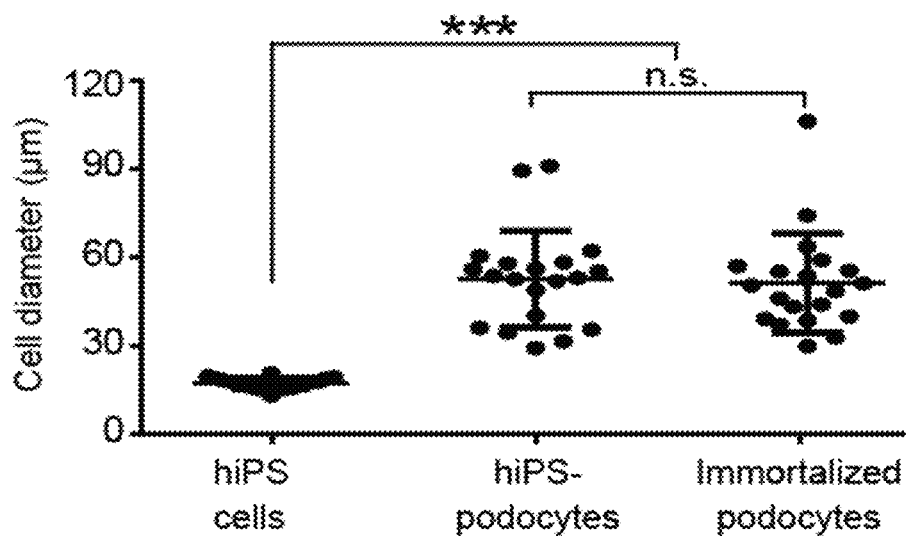

FIGS. 4A-4B show size characterization of human iPS cells and podocytes derived therefrom. (FIG. 4A) Bight field images of dissociated/non-adhered human iPS cells (left), human iPS-derived podocytes (middle), and immortalized human podocytes as positive control (right). (FIG. 4B) Dot plot showing diameter (y-axis) of dissociated/non-adhered human iPS cells (left), hiPS-derived podocytes (middle), and immortalized human podocyte (right). Error bars represent the standard deviation of the mean, n=20 cells. n.s.: not significant. ***denotes p-value <0.0001.

Figure 5A:
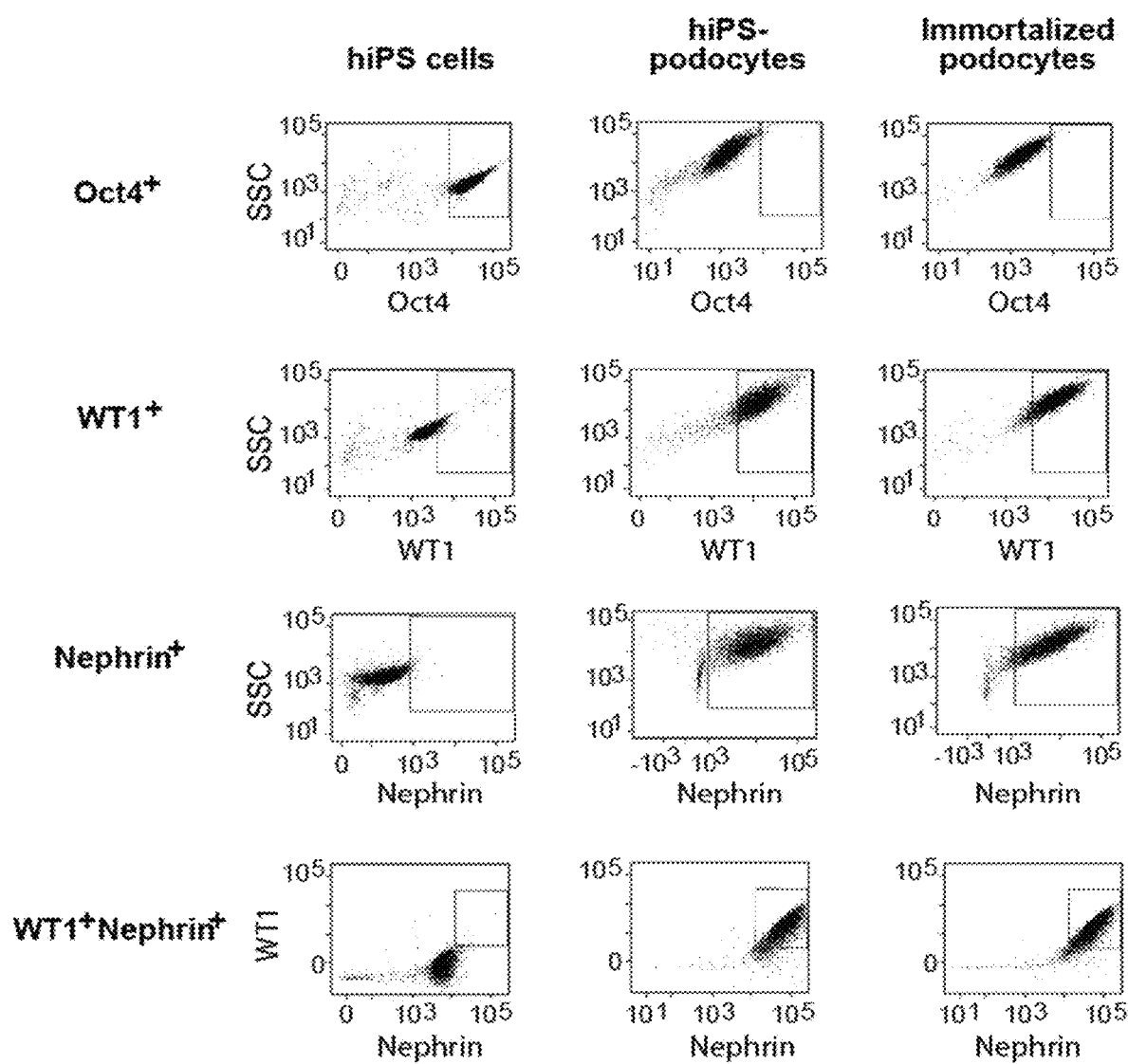
Figure 5B:
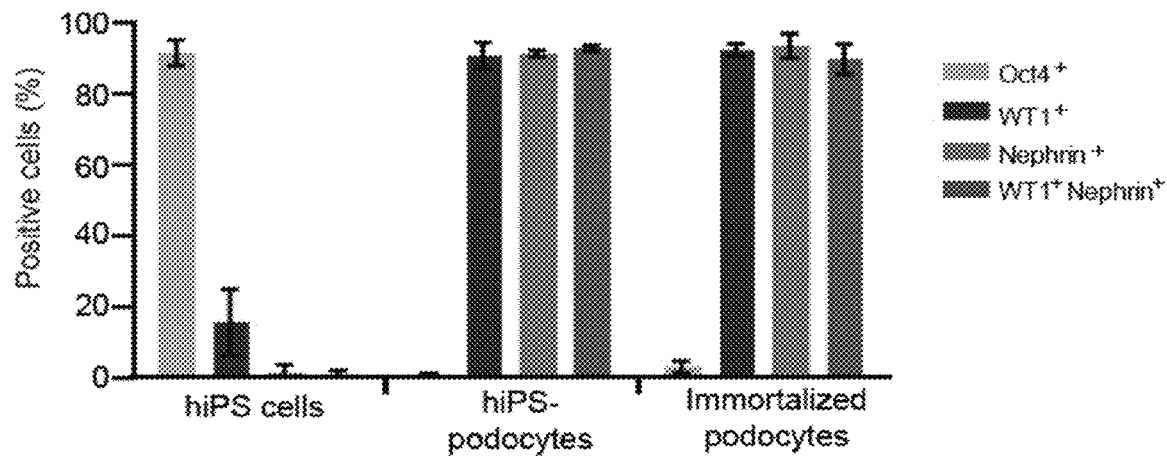

FIGS. 5A-5B show quantification and efficiency of the derivation of podocytes from human PS cells. (FIG. 5A) Flow cytometry analyses for the expression of pluripotency and podocyte markers in human iPS cells (left column), human iPS-derived podocytes (middle column), and immortalized human podocytes (right column). Immortalized human podocytes were used as positive control for podocyte markers. Representative plots for the expression levels of Oct4 pluripotency marker (top row, x-axis), Wilm's tumor protein 1 (WT1, a marker of kidney cells) (second row, x-axis), nephrin (podocyte-specific marker) (third row, x-axis), and dual expression of WT1 and nephrin (fourth row, nephrin on x-axis and WT1 on y-axis). (FIG. 5B) Quantitative representation of flow cytometry analyses illustrated in FIG. 5A. Y-axis represents the percentage of cells positive for Oct4, WT1, nephrin, and dual positive for WT1 and nephrin. Error bars represent standard deviation of the mean, n=3.

Figure 6A:
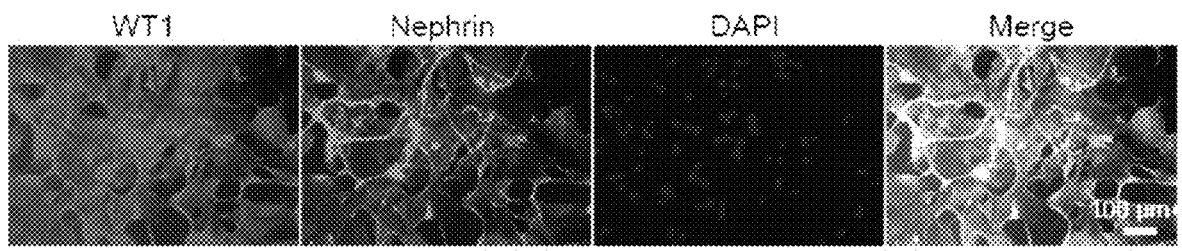
Figure 6B:
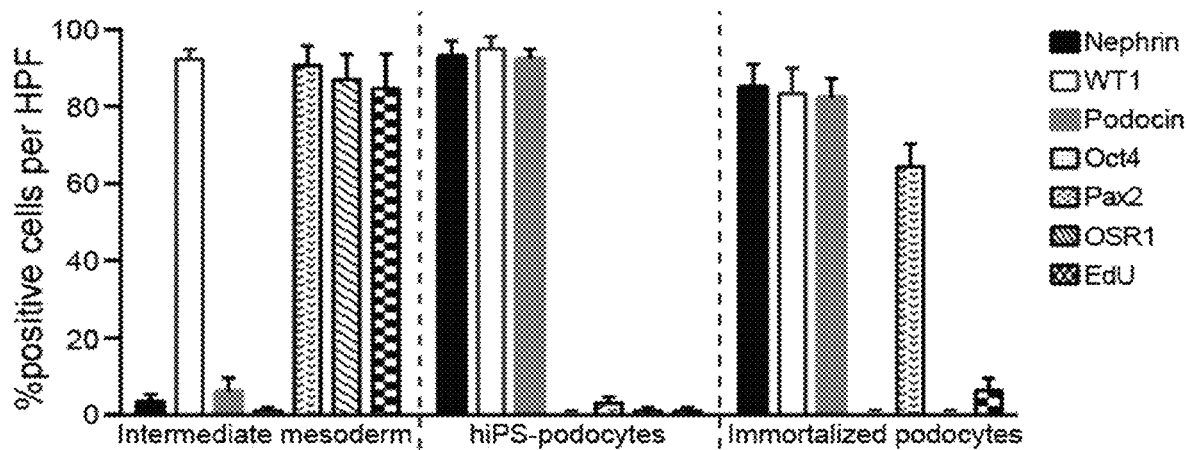

FIGS. 6A-6B show immunohistochemical analysis of human PS-derived podocytes. (FIG. 6A) Representative fluorescent images showing human iPS-derived podocytes immunostained for WT1 and nephrin, and counterstained with DAPI (nuclei). (FIG. 6B) Quantification of human iPS-derived podocytes indicates upregulation of podocyte markers (nephrin, WT1, and podocin), with corresponding decrease in pluripotency marker (Oct4). The decrease in progenitor cell markers (Pax2 and OSR1) and lack of EdU incorporation in human iPS-derived podocytes indicate that the cells are post-mitotic and terminally differentiated, as in mature podocytes. Error bars represent standard deviation of the mean, n=3. HPF: high power field; OSR1: odd-skipped related transcription factor protein 1; EdU: 5-ethynyl-2'-deoxyuridine.

Figure 7A:
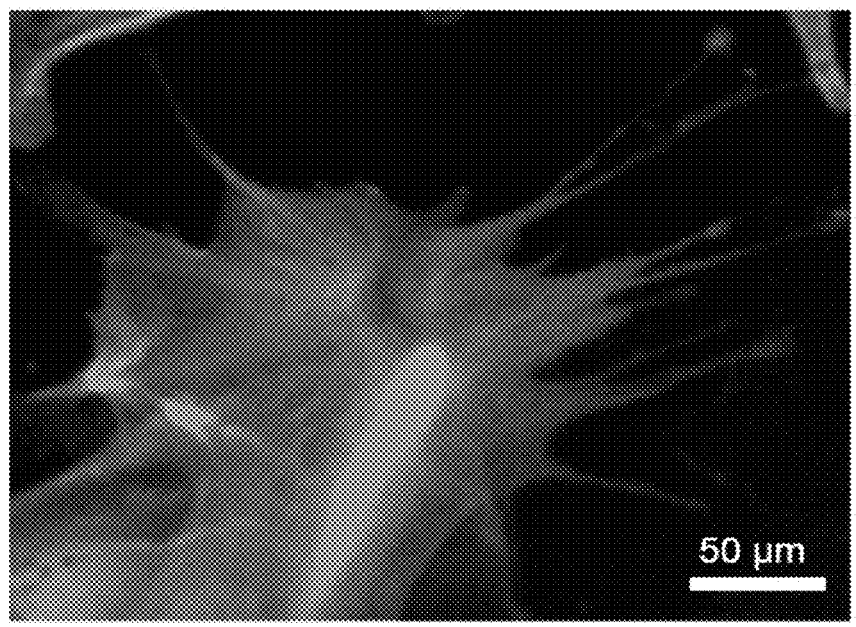
Figure 7B:
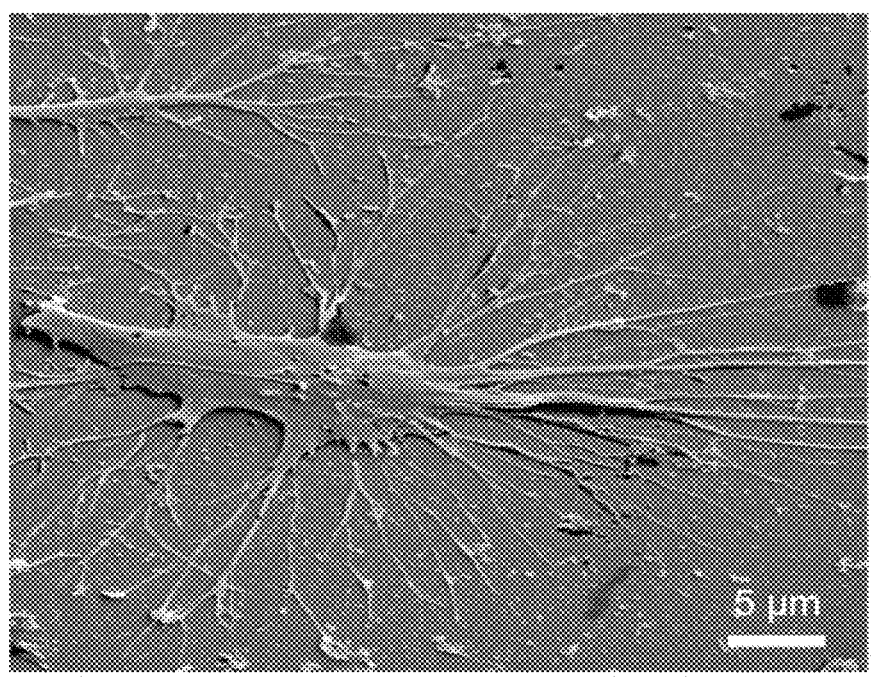

FIGS. 7A-7B are images of human PS-derived podocytes exhibiting foot processes. (FIG. 7A) Fluorescence microscopy image of human iPS-derived podocytes immunostained for podocin. The cells express podocin in both the cell body and foot processes. (FIG. 7B) Scanning electron microscopy image of human iPS-derived podocytes. The differentiated cells exhibit primary and secondary foot processes as in mature and functional glomerular podocytes.

Figure 8A:
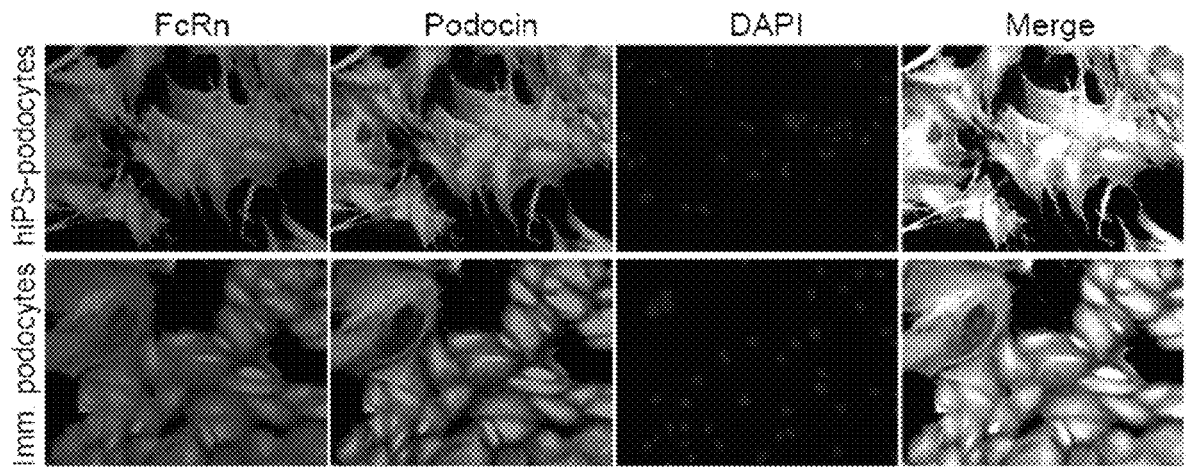
Figure 8B:
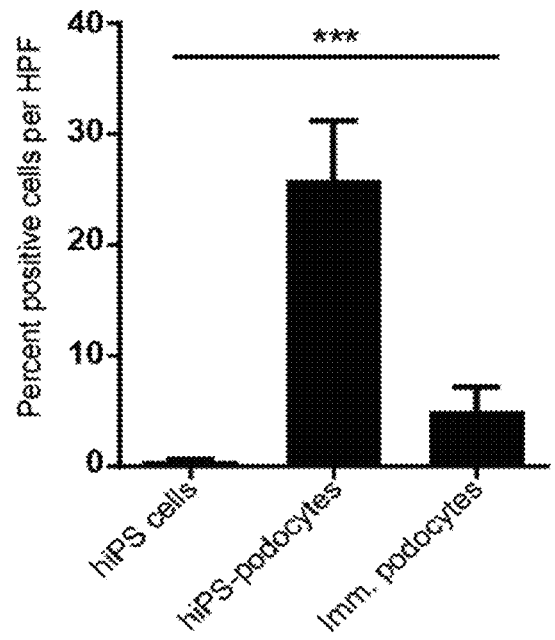

FIGS. 8A-8B show that human PS-derived podocytes express receptor for IgG and albumin transport, and uptake exogenous albumin. (FIG. 8A) Fluorescence microscopy images of human iPS-derived podocytes (top panel) immunoreactive for FcRn (IgG and albumin transport receptor) and podocin (podocyte marker). Human iPS-derived podocytes express FcRn in the cell nucleus, cytoplasm, and foot processes. Human immortalized podocytes (bottom panel) were used as positive control. Cells were counterstained with DAPI (nuclei). (FIG. 8B) Quantification of cells that exhibit uptake of fluorescently labeled albumin. Y-axis represents the percentage of cells that exhibit uptake of labeled albumin after 1 hr exposure. Human iPS-derived podocytes display enhanced ability to uptake exogenous albumin, a feature of functional glomerular podocytes. Error bars represent standard deviation of the mean, n=3. HPF: high power field; ***denotes p-value <0.0001.

Figure 9A:
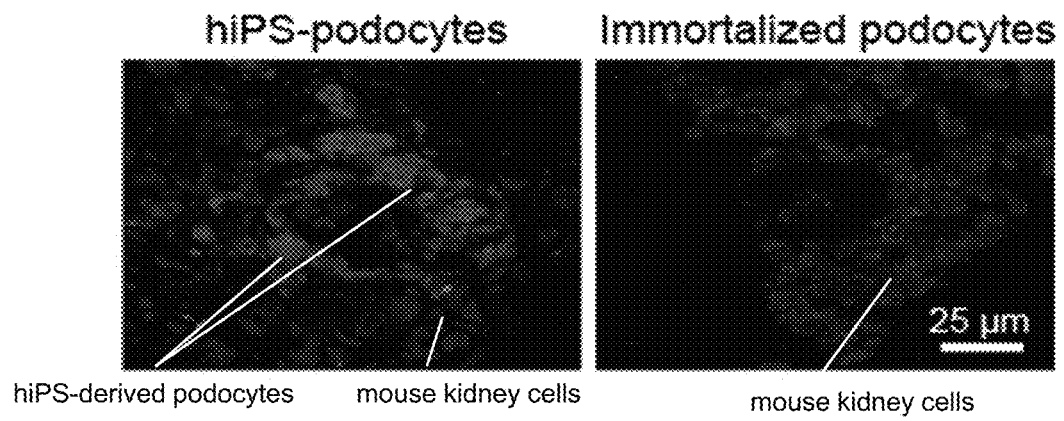
Figure 9B:
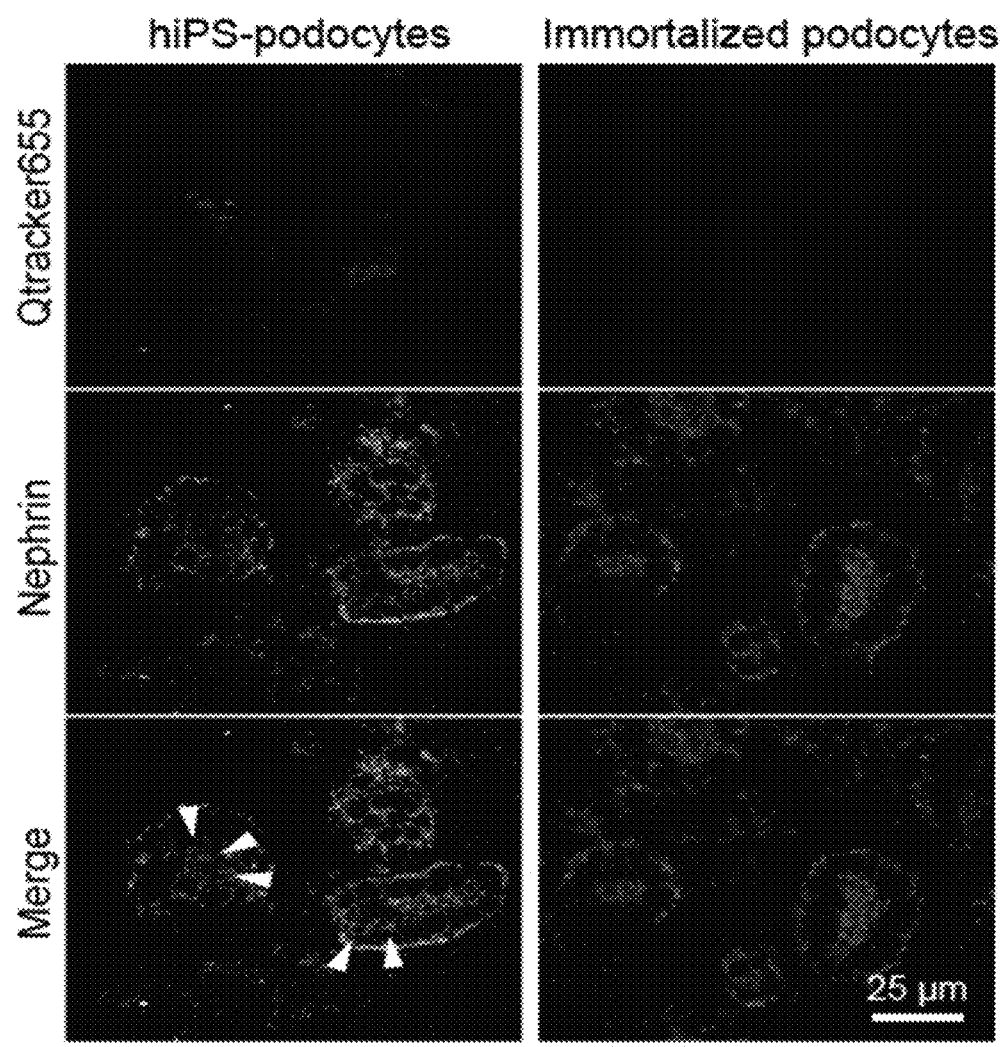
Figure 9C:
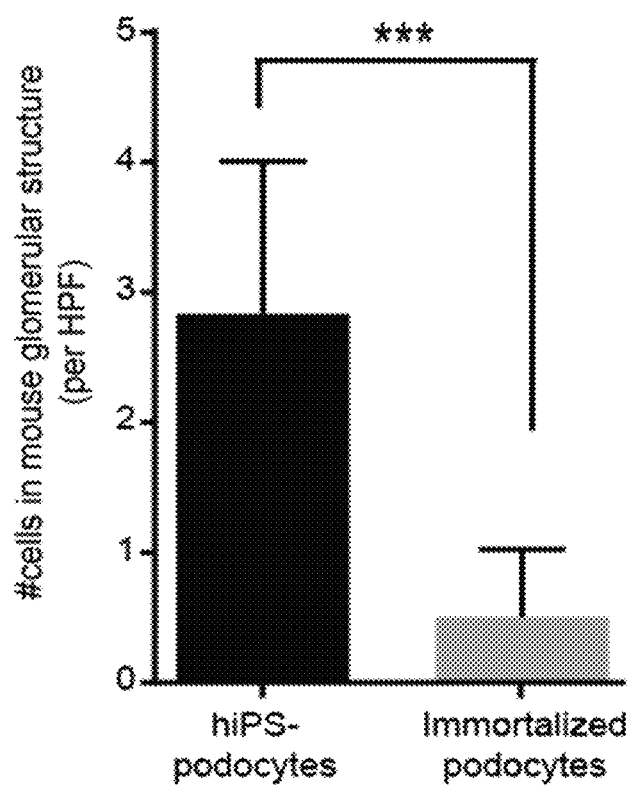

FIGS. 9A-9C show that human PS-derived podocytes integrate into developing mouse kidneys and localize to glomerular capillary structures. (FIG. 9A) Fluorescent images of sectioned embryonic mouse kidneys (E16) microinjected with pre-labeled (Qtracker655-labeled) human iPS-derived podocytes (left) and immortalized human podocytes (right) and cultured for 3 days. Kidneys were sectioned and counterstained with DAPI (nucleus). Images show that the microinjected cells integrate into the mouse kidneys. (FIG. 9B) Representative immunofluorescence images of sectioned mouse kidneys show immunoreactivity for nephrin, a podocyte marker and indicator of glomerular capillary structures. Images show that human iPS-derived podocytes localize into glomerular structures (white arrow heads) more efficiently than immortalized human podocyte cell line. Images are representative of 3 independent experiments and total of 9 kidneys per experimental condition. (FIG. 9C) Quantification of the number of human iPS-derived podocytes and immortalized human podocytes localized to nephrin-positive glomerular capillary structures in mouse embryonic kidneys. The ability of human PS-derived podocytes to integrate into the kidney and localize to glomerular structures indicates that the cells can be used for tissue/organ regeneration and/or development of cell-based therapeutics. Error bars represent standard deviation of the mean, n=3. HPF: high power field; ***denotes p-value <0.0001.

FIGS. 10A-10G show use of an organ-on-chip microphysiological device to perform the differentiation of human iPS-derived podocytes and to model the structure and function of human glomerular capillary wall. (FIG. 10A) Schematic representation of glomerular capillary wall showing podocytes and endothelial cells separated by glomerular basement membrane (GBM). Exemplary directional flow of molecules from capillary lumen to urinary space is shown by arrowed line. (FIG. 10B) Photograph (left) and schematic (right) of an exemplary microfluidic organ-on-chip device with compartments simulating the function of the urinary and capillary components of the glomerulus. The glomerular basement membrane is modeled by a porous PDMS membrane that is amenable to functionalization with ECM protein(s). (FIG. 10C) Fluorescent images of human iPS-derived podocytes differentiated in organs-on-chips microfluidic devices. Cells were differentiated in static (left), fluid flow (middle), or fluid flow and mechanical strain (right) conditions. Fluid was flowed at a rate of about 60 µL/hr in both the urinary and capillary compartments of the device. Strain was applied by mechanically stretching the PDMS membrane using vacuum. Cyclic strain was applied at 1 Hertz and 10% stretch of the membrane. Cells were immunostained for nephrin and counterstained with DAPI. (FIG. 10D) Human iPS-derived podocytes differentiated in microfluidic organs-on-chips with human glomerular endothelial cells cultured on opposite side of the PDMS membrane. The cells were cultured static flow, or fluid flow (shear stress) with or without mechanical strain. Cells were immunostained for nephrin and counterstained with DAPI. (FIG. 10E) An in vitro model of glomerular tissue-tissue interface established by co-culture of human iPS-derived podocytes (immunostained for nephrin, top layer) and human glomerular endothelial cells (immunostained for VE-cadherein, bottom layer) in organs-on-chips microphysiological devices, separated by a flexible ECM-coated PDMS membrane. Cells were cultured under static (left), fluid flow (middle), or fluid flow and mechanical strain (right). (FIG. 10F) A view of the tissue-tissue interface formed by human iPS-derived podocytes (top layer) and human glomerular endothelial cells (bottom layer) show that mechanical strain (right) enhanced extension of podocyte foot processes through the basement membrane (the flexible ECM-coated PDMS membrane separating the podocytes and endothelial cells). This data indicate that in some embodiments, the podocyte differentiation strategy and/or mechanical forces can be used to facilitate interactions between podocytes and endothelial cells or any other cell type, thereby modulating tissue development and function. (FIG. 10G) Quantification of glomerular filtration of albumin and inulin continuously infused into the capillary channel of organs-on-chips lined by human iPS-derived podocytes and glomerular endothelial cells. This data shows selective retention of albumin in the capillary channel and filtration of inulin into the urinary channel, as in functional glomerulus in vivo. Error bars represent standard deviation of the mean, n=6. *denotes p-value <0.05 between experimental replicates.

Figure 11:
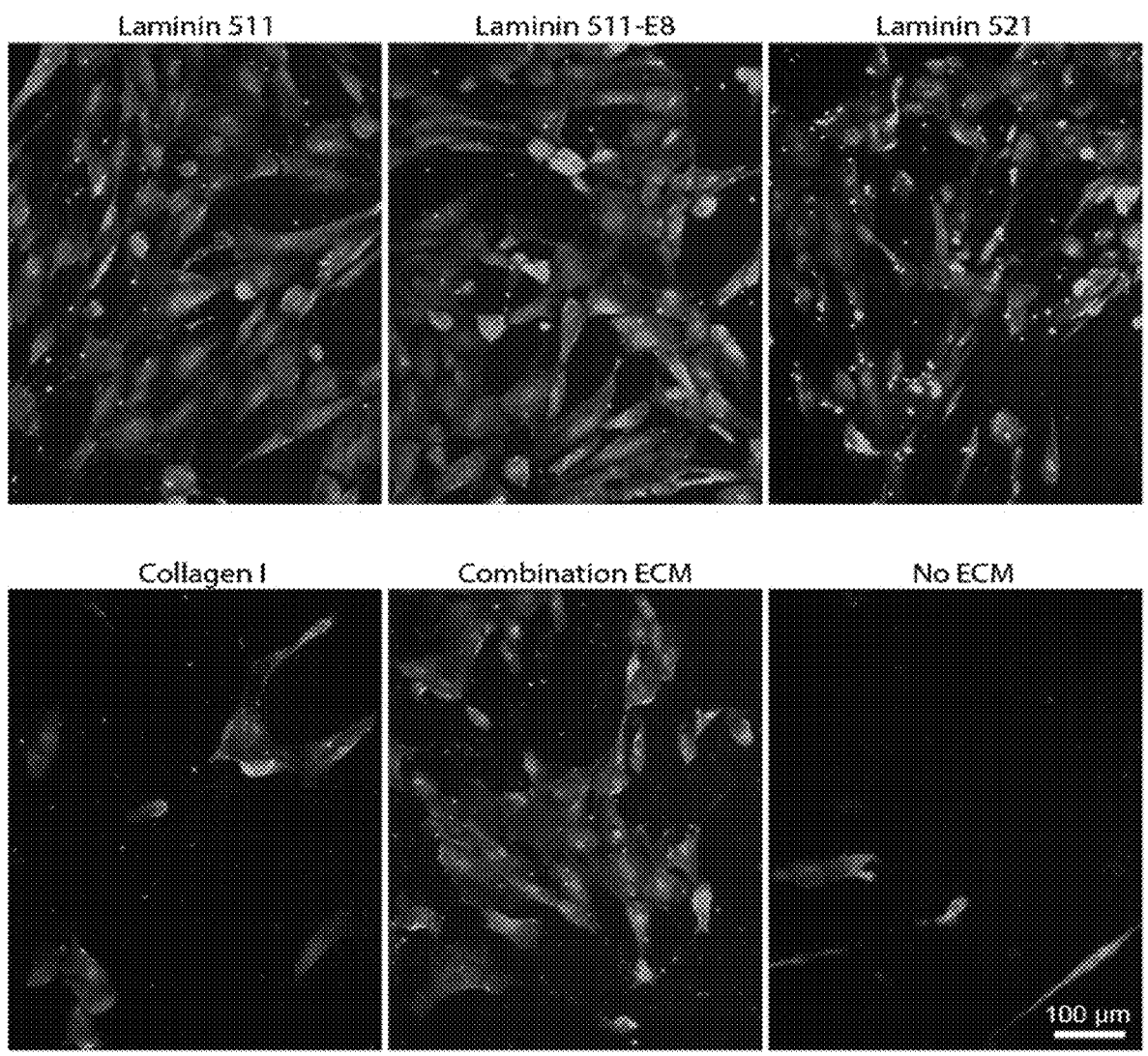

FIG. 11 is a set of fluorescent images showing extracellular matrix (ECM) proteins support the differentiation of human PS cells into podocytes. Immunofluorescent images of human iPS cells differentiated into podocytes when they were cultured with podocyte induction medium on tissue culture surfaces functionalized with either the extracellular matrix (ECM) protein laminin 511, laminin 511-E8 (a fragment of laminin 511), laminin 521 (also known as laminin 11), or collagen I. A combination of two or more of the above ECM proteins can also support the differentiation of human iPS cells into podocytes when used in combination with the podocyte induction medium. An exemplary surface functionalized with all of the above ECM proteins is shown (combination ECM). It should be noted that tissue culture surfaces lacking functionalization with ECM components or their mimetics can also support differentiation of human PS cells into podocytes, albeit sub-optimal for cell adhesion. Cells were immunostained for podocin.

Figure 12:
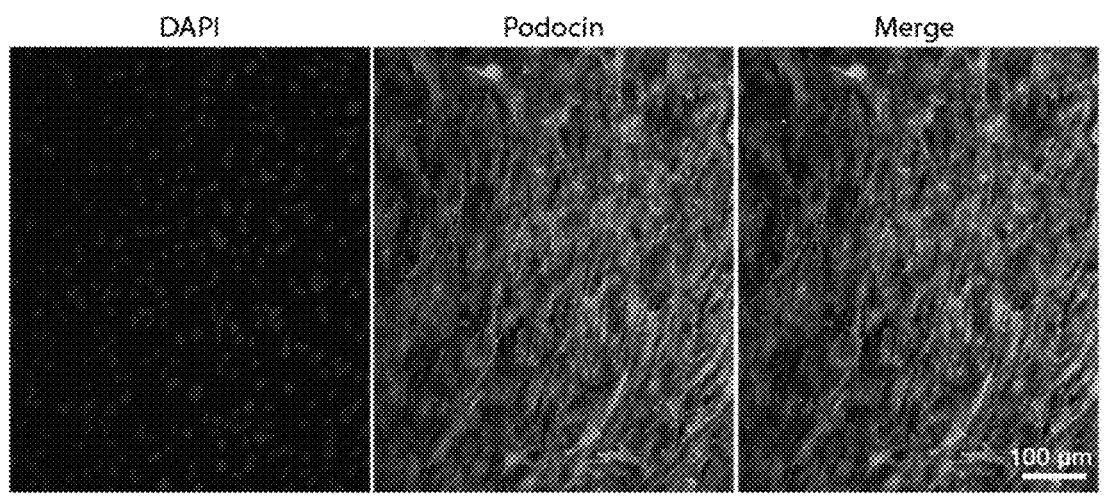

FIG. 12 is a set of fluorescent images showing that decellularized ECM supports adhesion and differentiation of human PS cells into podocytes. Exemplary images showing human iPS-derived podocytes that were differentiated by culturing on decellularized matrix produced by human glomerular endothelial cells. Differentiated human iPS cells were immunostained for podocin and counterstained with DAPI.

Figure 13:
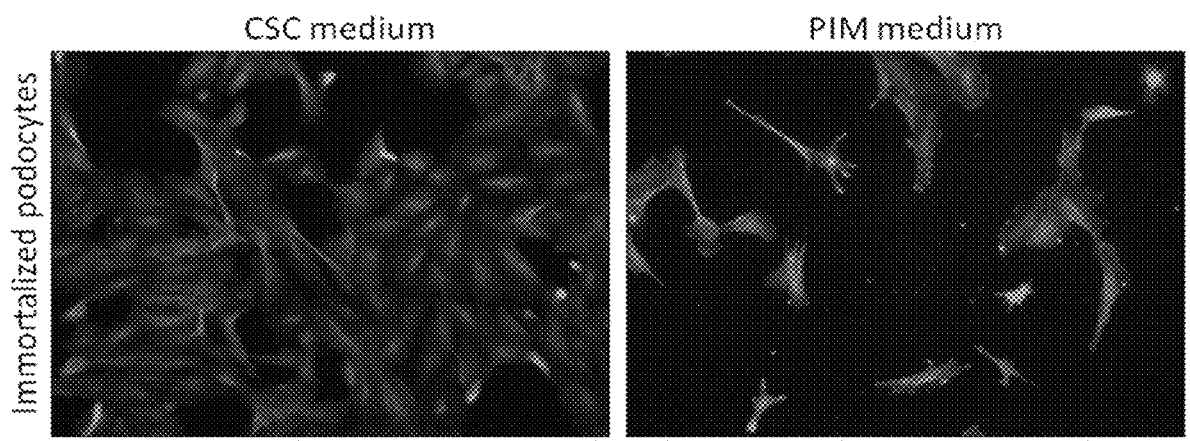

FIG. 13 is a set of fluorescent images showing that podocyte induction medium promotes differentiation and foot process development in immortalized human podocytes. Shown are fluorescent images of immortalized human podocytes cultured with regular CSC (Cell Systems Corporation) medium (left) typically used for culturing podocyte cell lines or the podocyte induction medium (right) described herein (e.g., as shown in FIG. 3A: stage 3 human PS cell differentiation medium). Cells were immunostained for podocin. The data shows that immortalized human podocytes cultured with the podocyte induction medium decrease proliferation and develop foot processes—both of which indicate enhanced podocyte specialization and maturation. Thus, this data underscores that the podocyte induction strategy described herein can be used to enhance differentiation and functional maturation of any podocyte cell type including precursor cells that give rise to the same, diseased or healthy cells.

DETAILED DESCRIPTION OF THE INVENTION

Aspects described herein stem from, at least in part, development of novel podocyte induction media and methods that efficiently direct differentiation of pluripotent stem (PS) cells and/or mesodermal cells into podocytes. In particular, the inventors have demonstrated inter alia that a podocyte induction medium comprising activin A, bone morphogenetic protein (BMP), an inhibitor of glycogen synthase kinase 3 (GSK-3) or an activator of Wnt signaling pathway, vascular endothelial growth factor (VEGF), and retinoic acid, efficiently induces differentiation of at least about 93% or more human PS cell (hPS)-derived intermediate mesoderm cells into podocytes within 3-5 days. Unlike pseudo-podocytes generated by existing differentiation methods that exhibit immature podocyte phenotype, in some embodiments, the novel podocyte induction media and/or the differentiation methods described herein can provide a reliable source of podocytes with mature phenotype, e.g., Pax-2 negative, and minimal or no proliferation capability. In addition, the hPS-derived podocytes exhibit primary and secondary foot processes as in mature and functional glomerular podocytes naturally occurring in vivo. The inventors have also demonstrated that mechanical forces and/or shear stress can be used in conjunction with the podocyte induction media described herein to enhance differentiation of hPS cells and their derivatives into podocytes, and/or to enhance interaction of differentiated podocytes with endothelial cells or any other cell type, e.g., in a co-culture. For example, the inventors have shown that application of a mechanical strain to the podocytes can enhance extension of podocyte foot processes toward the endothelial cells. The hPS cell-derived podocytes can be used in various applications, including, e.g., but not limited to, as an in vitro model for modeling a kidney/glomerular disorder, therapeutic clinical applications (e.g., tissue regeneration and/or repair or transplantation), drug discovery and/or developments, and/or tissue engineering. Accordingly, embodiments of various aspects described herein relate to methods, kits, and cell culture media for generation of podocytes from pluripotent stem (PS) cells, cells produced by the same, and methods of use.

Methods for Generating a Population of Podocytes

Various aspects described herein relates to methods for generating a population of podocytes. As used herein, the term "podocytes" refers to mitotic and/or post-mitotic cells that express at least one or more (e.g., at least two or more) podocyte-specific and/or kidney-specific markers and are differentiated or derived from pluripotent stem cells, mesodermal cells, and/or intermediate mesodermal cells using one or more embodiments of the differentiation methods of various aspects described herein. Examples of podocyte-specific marker include but are not limited to nephrin, APOL1, alpha-actinin 4, podocin, podocalyxin, synaptopodin, the 13A antigen, B7-1, CD2AP, CD10, cortactin, desmin, dystroglycan, ezrin, FAT, GLEPP1 (glomerular epithelial protein 1), Lmxlb, MAP-LC3 (microtubule-associated protein 1 light chain 3, myocilin, NEPH1, P-cadherin, PHM-5, podoplanin, Wilms' tumor-1 protein (WT-1), and a combination of two or more thereof. In some embodiments, the term "podocytes" refers to mitotic and/or post-mitotic cells that express nephrin and/or WT-1, and are differentiated or derived from pluripotent stem cells, mesodermal cells, and/or intermediate mesodermal cells using one or more embodiments of the differentiation methods of various aspects described herein. In some embodiments, the differentiated podocytes do not express any detectable levels of pluripotency markers known by one of ordinary skill in the art, including but not limited to Alkaline Phosphatase, SSEA3, SSEA4, Sox2, Oct3/4, Nanog, T AI60, TRA I81, TDGF 1, Dnmt3b, FoxD3, GDF3, Cyp26al, TERT, and zfp42.

In some embodiments, the podocytes generated by the methods of various aspects described herein are mitotic podocytes. In general, immature (mitotic) differentiated podocytes can express one or more (e.g., one, two, three or more) intermediate mesodermal cell-specific markers described herein (e.g., but not limited to, OSR1, OSR2, PAX2, or a combination of two or more thereof). Further, they can express one or more (e.g., one, two, three or more) podocyte-specific markers described herein (e.g., but not limited to, WT1, nephrin, podocin, podocalyxin, synaptopodin, APOL1, and a combination of two or more thereof).

In some embodiments, the podocytes generated by the methods of various aspects described herein are post-mitotic podocytes. Mature (post-mitotic) differentiated podocytes are substantially negative for at least one or more (including, e.g., at least two, at least three or more) intermediate mesodermal cell-specific markers described herein (e.g., but not limited to, PAX2, OSR1, and OSR2), and substantially positive for at least one or more (including, e.g., at least two, at least three or more) podocyte-specific markers described herein (e.g., but not limited to, WT1, nephrin, podocin, podocalyxin, synaptopodin, and APOL1). In some embodiments, mature (post-mitotic) differentiated podocytes can be substantially negative for PAX2, OSR1, and OSR2; and substantially positive for WT1, nephrin, podocin, podocalyxin, synaptopodin, and APOL1.

The term "substantially negative," when used with respect to the expression of certain cell-specific marker in a cell or a population of cells, means that the marker is not present or expressed, or is present or expressed at a level that is not detectable by methods known in the art, or is present or expressed at a level that does not confer any significant or detectable biological effect on the cell(s). In some embodiments, when the term "substantially negative" is used in connection with a population of cells, it can mean that at least about 70% or more, including, e.g., at least about 80%, at least about 90%, at least about 95% or more (including up to 100%) of the total cell population do not express a cell-specific marker, or express a marker at a level that is not detectable by methods known in the art, or express a marker at a level that does not confer any significant or detectable biological effect on the cells.

The term "substantially positive," when used with respect to the expression of certain cell-specific marker in a cell or a population of cells, means that the marker is present or expressed in the cell(s). In some embodiments, the level (e.g., protein or mRNA level) of the marker present or expressed in cell(s) is comparable to or greater than a reference level. For example, when the differentiated podocytes are substantially positive for at least one or more (including, e.g., at least two, at least three or more) podocyte-specific markers, in some embodiments, the level (e.g., protein or mRNA level) of the podocyte-specific specific marker(s) expressed in the podocytes can be comparable (e.g., within 10%, within 5% or less) to the level (e.g., protein or mRNA level) of the corresponding marker(s) expressed in mature podocytes naturally occurring in vivo or established podocyte cell lines. In some embodiments, the level (e.g., protein or mRNA level) of the podocyte-specific specific marker(s) expressed in the podocytes can be greater than the level (e.g., protein or mRNA level) of the corresponding marker(s) expressed in mature podocytes naturally occurring in vivo or established podocyte cell lines, for example, by at least 30% or more, including, e.g., at least 40%, at least 50%, at least 60%, at least 70%, at least 80%, at least 90%, at least 95% or more. In some embodiments, the level (e.g., protein or mRNA level) of the podocyte-specific specific marker(s) expressed in the podocytes can be greater than the level (e.g., protein or mRNA level) of the corresponding marker(s) expressed in mature podocytes naturally occurring in vivo or established podocyte cell lines, for example, by at least 1.1-fold or more, including, e.g., at least 1.5-fold, at least 2-fold, at least 3-fold, at least 4-fold, at least 5-fold, at least 10-fold, at least 25-fold, at least 50-fold, or more. In some embodiments, when the term "substantially positive" is used in connection with a population of cells, it can mean that at least about 70% or more, including, e.g., at least about 80%, at least about 90%, at least about 95% or more (including up to 100%) of the total cell population express a cell-specific marker, e.g., at a level that is comparable to or greater than a reference level.

In one aspect, the method comprises contacting a population of pluripotent stem (PS) cells with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free.

The method produces a population of cells that comprises an increased percentage of podocytes, e.g., by at least about 30% or more, including, e.g., at least about 40%, at least about 50%, at least about 60%, at least about 70%, at least about 80%, at least about 90%, or more, as compared to the pluripotent stem cells not contacted with the podocyte induction medium. In some embodiments, the method can produce a population of cells that comprises an increased percentage of podocytes, e.g., by at least about 1.1-fold or more, including, e.g., at least about 1.5-fold, at least about 2-fold, at least about 3-fold, at least about 4-fold, at least about 5-fold, at least about 10-fold, or more, as compared to the pluripotent stem cells not contacted with the podocyte induction medium.

In some embodiments, at least about 70% or higher, including, e.g., at least about 80%, at least about 90%, at least about 95%, or more (up to 100%) of the pluripotent stem cells can be differentiated into podocytes.

Podocyte induction medium: In some embodiments of the methods of various aspects described herein, the podocyte induction medium can be prepared from a basal culture medium supplemented with at least (i) activin A, (ii) BMP, (iii) a GSK-3 inhibitor or an activator of Wnt signaling pathway, (iv) VEGF, and (v) retinoic acid. Examples of a basal culture medium include, without limitations, Minimum Essential Medium (MEM), Eagle's Medium, Dulbecco's Modified Eagle Medium (DMEM), Dulbecco's Modified Eagle Medium: Nutrient Mixture F-12 (DMEM F12), F-10 Nutrient Mixture, Ham's F-10 Nutrient Mix, Ham's F12 Nutrient Mixture, Medium 199, RPMI, RPMI 1640, reduced serum medium, basal medium (BME), DMEM/F12 (1:1), and the like, and combinations thereof.

In the methods of various aspects described herein, the concentrations of each individual component in the podocyte induction medium can vary from ng/mL to mg/mL or from nM to µM.

(i) Activin A: Activins are homodimers or heterodimers of various beta subunit isoforms. As used herein and throughout the specification, the term "Activin A" generally refers to an activin A (beta A-beta A) polypeptide or a fragment thereof that is similar or identical to the sequence of a wild-type activin A (beta A-beta A) or fragment thereof. For example, an activin A polypeptide or fragment thereof has an amino acid sequence that is at least 70% or more (including at least 75%, at least 80%, at least 85%, at least 90%, at least 95%, at least 97%, at least 99%, or 100%) identical to that of a wild-type activin A (beta A-beta A), and is capable of having the normal functioning of activin A with respect to differentiation of pluripotent stem cells into podocytes. The activin A (beta A-beta A) used in the methods of various aspects described herein can be naturally occurring or recombinant protein or peptide.

In some embodiments of this aspect and other aspects described herein, the concentration of the activin A can range from about 50 ng/mL to about 500 ng/mL or from about 75 ng/mL to about 250 ng/mL, or from about 75 ng/mL to about 150 ng/mL, or from about 90 ng/mL to about 110 ng/mL. In one embodiment of this aspect and other aspects described herein, the concentration of the activin A is about 100 ng/mL.

(ii) Bone morphogenetic protein (BMP): As used interchangeably herein and throughout the specification, the terms "bone morphogenetic protein" and "BMP" generally refer to a BMP polypeptide or a fragment thereof that is similar or identical to the sequence of a wild-type BMP or fragment thereof. For example, a BMP polypeptide or fragment thereof has an amino acid sequence that is at least 70% or more (including at least 75%, at least 80%, at least 85%, at least 90%, at least 95%, at least 97%, at least 99%, or 100%) identical to that of a wild-type BMP, and is capable of having the normal functioning of BMP with respect to differentiation of pluripotent stem cells into podocytes. The BMP used in the methods of various aspects described herein can be naturally occurring or recombinant protein or peptide.

Twenty BMPs have been discovered to date, of these, six BMPs (i.e., BMP-2 through BMP-7) belong to the Transforming growth factor β (beta) super family of proteins. In particular, the BMPs that are associated with stem cell differentiation and/or implicated in tissue development arising from the mesodermal lineage can be used in the differentiation methods of various aspects described herein. Non-limiting examples of BMP include, but are not limited to, BMP-2, BMP-4, BMP-5, BMP-6, and BMP-7. In a specific embodiment, the BMP is human BMP.

In some embodiments of this aspect and other aspects described herein, the BMP can be any member of BMP family. In some embodiments, the BMP can be BMP-2, BMP-4, BMP-7, or a combination of two or more thereof. In some embodiments, the BMP can be BMP-7.

In some embodiments of this aspect and other aspects described herein, the concentration of the BMP can range about 50 ng/mL to about 500 ng/mL or from about 75 ng/mL to about 250 ng/mL, or from about 75 ng/mL to about 150 ng/mL, or from about 90 ng/mL to about 110 ng/mL. In one embodiment of this aspect and other aspects described herein, the concentration of the BMP is about 100 ng/mL.

(iii)(a) GSK-3 inhibitors: As used interchangeably herein and throughout the specification, the terms "inhibitor of glycogen synthase kinase (GSK-3)" and "GSK-3 inhibitor" refer to an agent that interferes with the normal functioning of GSK-3 protein kinase activity (e.g., the capacity of beta catenin phosphorylation), either by decreasing transcription or translation of GSK-3-encoding nucleic acid, or by inhibiting or blocking GSK-3 polypeptide activity, or both. Examples of GSK-3 inhibitors include, but are not limited to, antisense polynucleotides, interfering RNAs, catalytic RNAs, RNA-DNA chimeras, GSK-3-specific aptamers, anti-GSK-3 antibodies, GSK-3-binding fragments of anti-GSK-3 antibodies, GSK-3-binding small molecules, GSK-3-binding peptides, and other polypeptides that specifically bind GSK-3 (including, but not limited to, GSK-3-binding fragments of one or more GSK-3 ligands, optionally fused to one or more additional domains), such that the interaction between the GSK-3 inhibitor and GSK-3 results in a reduction or cessation of GSK-3 activity or expression.

In some embodiments of this aspect and other aspects described herein, the GSK-3 inhibitor can be selected from the group consisting of: CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), GSK-3 inhibitor VI (2-Chloro-1-(4,5-dibromo-thiophen-2-yl)-ethanone), GSK-3 inhibitor VII (2,4'-Dibromoacetophenone), GSK-3 inhibitor X (6-Bromoindirubin-3'-acetoxime), GSK-3 inhibitor IX ((2Z, 3E)-6'-Bromo-3-(hydroxyimino)-[2,3'-bi-indolinylidene]-2'-one), GSK-3 inhibitor XII (TWS119; 3-[[6-(3-aminophenyl)-7H-pyrrolo[2,3-d]pyrimidin-4-yl]oxy]-phenol), GSK-3 inhibitor XV (pyridocarbazolo-cyclopentadienyl ruthenium complex), GSK-3 inhibitor XVI (6-(2-(4-(2,4-Dichlorophenyl)-5-(4-methyl-1H-imidazol-2-yl)-pyrimidin-2-ylamino)ethyl-amino)-nicotinonitrile), lithium chloride, valproic acid (2-Propylpentanoic acid), SB216763 (3-(2,4-Dichlorophenyl)-4-(1-methyl-1H-indol-3-yl)-1H-pyrrole-2,5-dione), SB415286 (3-[(3-Chloro-4-hydroxyphenyl)amino]-4-(2-nitrophenyl)-1H-pyrrole-2,5-dione), Indirubin (6-bromoindirubin-3'-[O-(N,N-diethylcarbamyl)-oxime; 6-bromoindirubin-3'-[O-(2-morpholin-1-ylethyl)-oxime] hydrochloride), Kenpaullone (9-Bromo-7,12-dihydroindolo-[3,2-d][1]benzazepin-6(5H)-one), Hymenidin (2-Debromooroidin), variants thereof, and a combination of two or more thereof. In one embodiment, the GSK-3 inhibitor used in the methods of various aspects described herein is CHIR 99021 or a variant thereof.

In some embodiments of this aspect and other aspects described herein, the concentration of the inhibitor of GSK-3 can range from about 0.1 µM to about 10 µM, or from about 0.5 µM to about 5 µM, or from about 1 µM to about 5 µM. In one embodiment of this aspect and other aspects described herein, the concentration of the inhibitor of GSK-3 is about 3 µM.

(iii)(b) Activators of Wnt signaling pathway: As used interchangeably herein and throughout the specification, the term "activator of Wnt signaling pathway" refers to an agent that enhances or stimulates the normal functioning of Wnt signaling pathway, either by increasing transcription or translation of Wnt-encoding nucleic acid, and/or by inhibiting or blocking activity of a molecule that inhibits Wnt expression or Wnt activity, and/or by enhancing normal Wnt activity. For example, the Wnt activator can be selected from an antibody, an antigen-binding fragment, an aptamer, an interfering RNA, a small molecule, a peptide, an antisense molecule, and another binding polypeptide. In another example, the Wnt activator can be a polynucleotide selected from an aptamer, interfering RNA, or antisense molecule that interferes with the transcription and/or translation of a Wnt-inhibitory molecule.

As used herein, the term "Wnt" is meant the family of highly conserved secreted signaling molecules which play key roles in both embryogenesis, tissue regeneration, and mature tissues. The human Wnt gene family has at least 19 members (Wnt-1, Wnt-2, Wnt-2B/Wnt-13, Wnt-3, Wnt3a, Wnt-4, Wnt~5A, Wnt-5B, Wnt-6, Wnt-7A, Wnt-7B, Wnt-8A, Wnt-8B, Wnt-9A/Wnt-14, Wnt-9B Wnt-15, Wnt-10A, Wnt-10B, Wnt-11, and Wnt-16). Wnt proteins modulate cell activity by binding to Wnt receptor complexes that include a polypeptide from the Frizzled (Fz) family of proteins and a polypeptide of the low-density lipoprotein receptor (LDLR)-related protein (LRP) family of proteins. Once activated by Wnt binding, the Wnt receptor complex will activate one or more intracellular signaling cascades. These include the canonical Wnt signaling pathway: the Wnt planar cell polarity (Wnt PCP) pathway: and the Wnt-calcium (Wnt/Ca$^{2+}$) pathway.

In some embodiments of this aspect and other aspects described herein, the activator of Wnt signaling pathway can be selected from the group consisting of Wnt3a, FGF18, beta-catenin, norrin, R-spondin2, variants thereof, and a combination of two or more thereof.

In some embodiments of this aspect and other aspects described herein, the concentration of the activator of Wnt signaling pathway can range from about 0.1 µM to about 10 µM, or from about 0.5 µM to about 5 µM, or from about 1 µM to about 5 µM. In one embodiment of this aspect and other aspects described herein, the concentration of the activator of Wnt signaling pathway is about 3 µM.

(iv) Vascular endothelial growth factor (VEGF): As used interchangeably herein and throughout the specification, the terms "vascular endothelial growth facto" or "VEGF" generally refers to a VEGF polypeptide or a fragment thereof that is similar or identical to the sequence of a wild-type VEGF or fragment thereof. For example, a VEGF polypeptide or fragment thereof has an amino acid sequence that is at least 70% or more (including at least 75%, at least 80%, at least 85%, at least 90%, at least 95%, at least 97%, at least 99%, or 100%) identical to that of a wild-type activin A (beta A-beta A), and is capable of having the normal functioning of VEGF with respect to differentiation of pluripotent stem cells into podocytes. The VEGF used in the methods of various aspects described herein can be naturally occurring or recombinant protein or peptide.

In some embodiments of this aspect and other aspects described herein, the concentration of the VEGF can range from about 10 ng/mL to about 250 ng/mL or from about 25 ng/mL to about 200 ng/mL, or from about 25 ng/mL to about 150 ng/mL or from about 30 ng/mL to about 100 ng/mL, or from about 40 ng/mL to about 75 ng/mL. In one embodiment of this aspect and other aspects described herein, the concentration of the VEGF is about 50 ng/mL.

In some embodiments of this aspect and other aspects described herein, other angiogenic and/or vasculogenic factors, including, e.g., but not limited to, angiogenin, epidermal growth factor (EGF), heregulin, annexin A3, endothelin, insulin-like growth factor, and a combination of two or more thereof, can be used instead of or in combination with VEGF.

(v) Retinoic acid: Retinoic acid is a metabolite of vitamin A (retinol) that mediates the functions of vitamin A required for growth and development. As used herein and throughout the specification, the term "retinoic acid" generally refers to a naturally occurring retinoic acid or a derivative thereof (e.g., an artificially modified retinoic acid that retains at least 70% or higher of the functions of a naturally-occurring retinoic acid). Examples of retinoic acid and derivative thereof include, but are not limited to, (2E,4E,6E,8E)-3,7-dimethyl-9-(2,6,6-trimethylcyclohexen-1-yl)nona-2,4,6,8-tetraenoic acid, AM580 (4-[[(5,6,7,8-tetrahydro-5,5,8,8-tetramethyl-2-naphthalenyl)carbonyl]amino]-benzoic acid), TTNPB (4-[(1E)-2-(5,6,7,8-tetrahydro-5,5,8,8-tetramethyl-2-naphthalenyl)-1-propen-1-yl]-benzoic acid), retinol palmitate, retinol, retinal, 3-dehydroretinoic acid, 3-dehydroretinol, 3- dehydroretinal, and compounds described in Abe, E. et al., Proc. Natl. Acad. Sci., U.S.A., 78: 4990-4994, 1981; Schwartz, E. L. et al., Proc. Am. Assoc. Cancer Res., 24: 18, 1983; Tanenaga, K. et al., Cancer Res. 40: 914-919, 1980; Tamura, K. et al., Cell Differ. Dev. 32: 17-26, 1990; and Strickland, S. et al., Cancer Res. 43: 5268-5272, 1983.

In some embodiments of this aspect and other aspects described herein, the concentration of the retinoic acid can range from about 0.01 µM to about 1 µM, or from about 0.05 µM to about 0.75 µM, or from about 0.075 µM to about 0.5 µM, or from about 0.075 µM to about 0.25 µM. In one embodiment of this aspect and other aspects described herein, the concentration of the retinoic acid is about 0.1 µM.

In some embodiments, the podocyte induction medium can further comprise B27 supplement. As used herein and throughout the specification, the term "B27 supplement" refers to a composition comprising, essentially consisting of, or consisting of biotin, DL Alpha Tocopherol acetate, DL Alpha-Tocopherol, Vitamin A (acetate), BSA fatty acid free Fraction V, catalase, human recombinant insulin, human transferrin, superoxide dismutase, corticosterone, D-galactose, ethanolamine HCl, glutathione (reduced), L-carnitine HCl, linoleic acid, linolenic acid, progesterone, putrescine 2HCl, sodium selenite, and T3 (triodo-1-thyronine).

In some embodiments, the podocyte induction medium can further comprise glutamine or a derivative thereof. In some embodiments, the glutamine can be a stabilized form of L-glutamine and/or L-alanyl-L-glutamine.

In some embodiments, the podocyte induction medium can further comprise a member of FGF family (e.g., FGF9).

In some embodiments, the podocyte induction medium does not include TGF-beta or FGF2.

In some embodiments, the podocyte induction medium does not include an inhibitor of SMAD signaling (e.g., but not limited to, Noggin and SB431542).

In some embodiments, the podocyte induction medium does not include an activator of Hippo signaling.

In one embodiment, the podocyte induction medium is DMEM/F12 basal medium supplemented with activin A, BMP (e.g., BMP-7), a GSK-3 inhibitor (e.g., CHIR99021 or an activator of Wnt signaling pathway, VEGF, retinoic acid, B27 supplement, and optional antibiotics (e.g., Penicillin-Streptomycin).

Individual components in the podocyte induction medium can each be independently present in solution (e.g., in a soluble form) or be immobilized on a biomaterial substrate in which the cells are cultured. In some embodiments, at least one or more (including, e.g., at least two or more) of the components (i)-(v) in the podocyte induction medium can be immobilized on a biomaterial substrate. In some embodiments, the immobilized component can form a gradient or uniform distribution. Immobilization can be accomplished by any methods known in the art, including, e.g., but not limited to, drying, adsorption, covalent cross-linking, or a combination of two or more thereof. In some embodiments, at least one or more of the components (i)-(v) in the podocyte induction medium can be immobilized on a biomaterial substrate by dry-coating a surface of the biomaterial substrate with a protein component of interest. In some embodiments, at least one or more of the components (i)-(v) in the podocyte induction medium can be immobilized on a biomaterial substrate by incubating a biomaterial substrate surface/scaffold with a solution of a protein component of interest. In some embodiments, at least one or more of the components (i)-(v) in the podocyte induction medium can be chemically or covalently immobilized on a biomaterial substrate. Some exemplary chemical reactions that can be used to achieve covalent immobilization include, but are not limited to, carbodiimide crosslinking (EDC), N-Hydroxysuccinimide Esters (NHS esters), sulfo-NHS chemistries, and a combination of two or more thereof. These crosslinking chemistries can enable direct conjugation by using carboxylates, primary amines, free thiols (sulfhydryls), aldehydes, carbonyls, and/or ketones on a protein component of interest. In some embodiments, VEGF, activin-A, and/or BMP (e.g., BMP-7) can be immobilized on a biomaterial substrate using any immobilization methods described above or known in the art.

As used herein, the term "pluripotent stem cells" or "PS cells" refers to cells with the capacity, under different conditions, to differentiate to cell type(s) characteristic of all three germ cell layers (endoderm, mesoderm and ectoderm). Pluripotent stem cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell. Pluripotent stem cells can be derived from any organism of interest, including, e.g. human, primate, non-human primate, canine, feline, murine, equine, porcine, avian, bovine etc.

In some embodiments, the pluripotent stem cells can comprise embryonic stem cells, induced pluripotent stem cells, or a combination thereof. As used herein, the term "embryonic stem (ES) cell" refers to a cell that (a) can self-renew, (b) can differentiate to produce all types of cells in an organism (pluripotent), and (c) is derived from a developing organism or is an established ES cell line which was derived from a developing organism. Embryonic stem cells may be obtained from the inner cell mass of the embryonic blastocyst (see U.S. Pat. Nos. 5,843,780, 6,200, 806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235, 970, which are incorporated herein by reference). In culture, ES cells typically grow as flat colonies with large nucleo-cytoplasmic ratios, defined borders and prominent nucleoli. In addition, hES cells express SSEA-3, SSEA-4, TKA-1-60, TRA-1-81, and Alkaline Phosphatase, but not SSEA-1. Examples of methods for identifying and characterizing ES cells may also be found in, for example, U.S. Pat. No. 7,029,913, which is incorporated herein by reference in its entirety.

The disclosure described herein, in some embodiments, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

In some embodiments, no human embryos are destroyed in preparation of the PS cells for use in the methods, compositions and kits described herein.

In some embodiments, the pluripotent stem cells are induced pluripotent stem cells. The term "induced pluripotent stem cell" or "iPSC" or "iPS cell" refers to a cell derived from reprogramming of the differentiation state of a differentiated cell (e.g. a somatic cell) into a pluripotent cell. An induced pluripotent stem cell (a) can self-renew, (b) can differentiate to produce all types of cells in an organism, and (c) is derived from a somatic cell. iPS cells have an ES cell-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, T AI60, TRA I81, TDGF 1, Dnmt3b, FoxD3, GDF3, Cyp26al, TERT, and zfp42. iPS cells can be generated by providing the cell with "reprogramming factors", i.e., one or more, e.g., a cocktail, of biologically active factors that act on a cell to alter transcription, thereby reprogramming a cell to pluripotency. Methods for generating and characterizing iPS cells are known in the art, and examples of which can be found in, for example, U.S. Patent Application Nos. US20090047263, US20090068742, US20090191 159, US20090227032, US20090246875, and US20090304646, the disclosures of which are incorporated herein by reference. In some embodiments, the PS cells are obtained from somatic cell nucleus transfer (SCNT), e.g., as described in Tachibana et al., Cell (2013) 153: 1228-1238; and Langerova et al., Cell Reprogram. (2013) 15: 481-483.

The pluripotent stem cells can be contacted with the podocyte induction medium for a pre-determined period of time, depending on subsequent use of the differentiated cells. For example, in some embodiments, if the differentiated cells were to be used for transplantation, it can be desirable that the pluripotent stem cells are contacted with the podocyte induction medium for a shorter period of time such that they are not fully differentiated into post-mitotic podocytes, and can integrate better with other cells upon transplantation. Accordingly, in some embodiments, the pluripotent stem cells can be contacted with the podocyte induction medium until at least a portion of the cells display one or more podocyte-specific marker (e.g., but not limited to, nephrin). In some embodiments, the pluripotent stem cells can be contacted with the podocyte induction medium until the cells reach a desirable differentiation stage (e.g., podocyte progenitors or precursor cells, immature podocytes, or mature podocytes). In some embodiments, the pluripotent stem cells can be contacted with the podocyte induction medium until the cells differentiate into post-mitotic podocytes (e.g., substantially incapable of proliferation). Accordingly, the contact period of time can range from about 1 day to 1 week to 1 month or longer. In some embodiments, the contact period of time can be at least about 3 days or longer. In some embodiments, the contact period of time can be at least about 5 days or longer. In some embodiments, the contact period of time can be at least about 7 days, at least about 8 days, at least about 9 days, at least about 10 days, at least about 15 days or longer. In some embodiments, the contact period of time can range from about 5 days to about 20 days or from about 7 days to about 10 days.

The optimum period of time for each differentiation stage can be determined, for example, by immunostaining the cells for presence of one or more (e.g., one, two, three, four, or more) markers specific for each stage (e.g., podocyte progenitors, immature podocytes, or mature podocytes). Distinct markers specific for each stage of PS cell differentiation are known in the art. For example, mesodermal cells can be characterized by the presence of at least one or more of mesodermal cell-specific markers, including, e.g., but not limited to, Brachyury, Goosecoid, Snail, Twist-1, Twist-2, Wnt-8a, N-Cadherin, MIXL1 (Mix/Bix paired-like homeodomain protein), GDF-1 (Growth/differentiation factors-1), and a combination of two or more thereof. Intermediate mesodermal cells can be characterized by the presence of at least one or more of the intermediate mesodermal cell-specific markers, including, e.g., but not limited to, OSR1 (Odd-Skipped Related Transcription Factor 1), Pax2 (Paired Box 2), Pax8 ((Paired Box 8), SIX2 (SIX homeobox 2), WT1 (Wilms tumor 1), Cited2 (Cbp/p300-interacting transactivator, with Glu/Asp-rich carboxy-terminal domain, 2), Eya1 (Eyes absent homolog 1), Sall1 (spalt-like transcription factor 1), and a combination of two or more thereof. Immature (mitotic) differentiated podocytes can be characterized by expression of at least one or more of intermediate mesodermal cell-specific markers (e.g., but not limited to, OSR1, OSR2, and PAX2) and at least one or more of podocyte-specific markers (e.g., but not limited to, WT1, nephrin, podocin, podocalyxin, synaptopodin, and APOL1). Mature (post-mitotic) differentiated podocytes can be characterized by absence of at least one (including, e.g., at least two, at least three or more) or all intermediate mesodermal cell-specific markers (e.g., but not limited to, PAX2, OSR1, and OSR2), and expression of at least one or more podocyte-specific markers (e.g., but not limited to, WT1, nephrin, podocin, podocalyxin, synaptopodin, and APOL1).

While not necessary, in some embodiments, the PS cells form embryoid bodies and/or organoids prior to or during the contact with the podocyte induction medium. As used herein, "embryoid body", "embryoid bodies", "EBs" or "EB cells" refers to a morphological, three-dimensional, or organoid-type structure comprised of a population of undifferentiated and differentiated cells which are derived from pluripotent stem cells (e.g., primate pluripotent stem cells (pPS), embryonic stem (ES) cells, induced pluripotent stem (IPS) cells) that have undergone differentiation. Under culture conditions suitable for EB formation, ES cells proliferate and form small mass of cells that begin to differentiate. In the first phase of differentiation, usually corresponding, to about days 1-4 of differentiation for human cells, the small mass of cells forms a layer of endodermal cells on the outer layer, and is considered a "simple embryoid body." In the second phase, usually corresponding to about days 3-20 post-differentiation for human cells, "complex embryoid bodies" are formed, which are characterized by extensive differentiation of ectodermal and mesodermal cells and derivative tissues. As used herein, the term "embryoid bodies" or "EB" encompasses both simple and complex embryoid bodies unless otherwise required by context. The determination of when embryoid bodies have formed in a culture of ES/iPS cells is routinely made by persons of skill in the art by, for example, visual inspection of the morphology, detection of cell markers. Floating masses of about 20 cells or more (e.g., ES/iPS cells) are considered to be suspension embryoid bodies. (see. e.g., Schmit R., et al, 1991, Genes Dev. 5:728-740; Doetschman, T. C, et al., 1985, J. Embryol. Exp. Morph. 87:27-45). Suspension EBs can be plated onto an adherent substrate to generate adherent EBs.

Embryoid body formation can be typically induced by culturing PS cell colonies/aggregates in suspension or non-adherent conditions. In some embodiments, a suspension culture can be initiated by first detaching the PS cells (e.g., in clumps) and then culturing them in nonadherent cell culture or tissue culture devices or vessels such as poly-HEMA [Poly(2-hydroxyethyl methacrylate)]-coated plates, Corning's Ultra-Low Attachment Surface, or any rotating vessel/bioreactor that can minimize cell attachment. Exemplary culture media typically used to form embryoid bodies include, without limitations, a basal medium (e.g., but not limited to, DMEM/DMEM/F12, RPMI and/or IMDM) supplemented with serum components (such as Fetal Bovine/Calf Serum or human serum) or a serum replacement (e.g., KnockOut™ Serum Replacement). Alternatively, embryoid bodies can be generated by using a serum-free medium. This approach can be used when the PS cell differentiation is desirable to be biased into a specific lineage.

In some embodiments, the embryoid bodies can be cultured using one or more embodiments of the podocyte inducing media described herein, alone or in combination with other embryoid body formation media such as those mentioned above.

The term "organoid" is used herein to mean a 3-dimensional growth of cells in culture that retains characteristics of a tissue or an organ in vivo, e.g. prolonged tissue expansion with proliferation, multilineage differentiation, recapitulation of cellular and tissue ultrastructure, and function, etc.

In another aspect, a method of generating a population of podocytes comprises contacting a population of mesodermal cells and/or intermediate mesodermal cells with a podocyte induction medium as described herein (for example, comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid), wherein the podocyte induction medium is serum-free.

The method produces a population of cells that comprises an increased percentage of podocytes, e.g., by at least about 30% or more, including, e.g., at least about 40%, at least about 50%, at least about 60%, at least about 70%, at least about 80%, at least about 90%, or more, as compared to a population of pluripotent stem cells or mesoderm or intermediate mesoderm cells not contacted with the podocyte induction medium. In some embodiments, the method can produce a population of cells that comprises an increased percentage of podocytes, e.g., by at least about 1.1-fold or more, including, e.g., at least about 1.5-fold, at least about 2-fold, at least about 3-fold, at least about 4-fold, at least about 5-fold, at least about 10-fold, or more, as compared to a population of pluripotent stem cells or mesodermal cells and/or intermediate mesodermal cells not contacted with the podocyte induction medium.

In some embodiments, at least about 70% or higher, including, e.g., at least about 80%, at least about 90%, at least about 95%, or more (up to 100%) of the mesodermal cells and/or intermediate mesodermal cells in the population of cells can be differentiated into podocytes.

As used interchangeably herein, the term "mesodermal cell" or "mesoderm cell" refers to a cell which can make copies of itself (division and proliferation) with limited self-renewal capacity (as opposed to pluripotent cells that can replicate indefinitely), and which has the ability to differentiate into all cell types constituting mesodermal tissues. A mesodermal cell generally expresses, for example, the cell markers Brachyury(+), Goosecoid(+), Snail(+), Twist-1(+), Twist-2(+), Wnt-8a(+), N-Cadherin(+), MIXL1 (+), GDF-1(+), SH2(+), SH3(+), SH4(+), CD29(+), CD44 (+), CD14(−), CD34(−), and CD45(−), but such cells are not limited to these markers. In some embodiments, the mesodermal cells are derived from pluripotent stem cells.

As used interchangeably herein, the term "intermediate mesodermal cell" or "intermediate mesoderm cell" refers to a cell capable of differentiating into pronephros, mesonephros, mesonephric duct, metanephros, adrenal cortex, or genital gland, and also expressing OSR1. In some embodiments, the intermediate mesodermal cells are derived from pluripotent stem cells or mesodermal cells. Intermediate mesodermal cells coexpress OSR1 and Pax2, and they express very little to no brachyury. In contrast, mesodermal cells express brachyury, goosecoid, and MIXL1. Mesodermal cells may also express Pax2, but are negative for OSR1 until intermediate mesoderm development is initiated.

The mesodermal cells or intermediate mesodermal cells can be contacted with the podocyte induction medium for a pre-determined period of time, depending on subsequent use of the differentiated cells. For example, in some embodiments, if the differentiated cells were to be used for transplantation, it can be desirable that the pluripotent stem cells are contacted with the podocyte induction medium for a shorter period of time such that they are not fully differentiated into post-mitotic podocytes, and can integrate better with other cells upon transplantation. Accordingly, in some embodiments, the mesodermal cells or intermediate mesodermal cells can be contacted with the podocyte induction medium until at least a portion of the cells display one or more podocyte-specific marker (e.g., but not limited to, nephrin). In some embodiments, the mesodermal cells or intermediate mesodermal cells can be contacted with the podocyte induction medium until the cells reach a desirable differentiation stage (e.g., podocyte progenitors or precursor cells, immature podocytes, or mature podocytes). In some embodiments, the mesodermal cells or intermediate mesodermal cells can be contacted with the podocyte induction medium until the cells differentiate into post-mitotic podocytes. Accordingly, the period of time can range from about 1 day to 1 week to 2 weeks or longer. In some embodiments, the period of time can be at least about 1 day, at least about 2 days, at least about 3 days, at least about 4 days, at least about 5 days or longer. The optimum period of time for each differentiation stage can be determined, for example, by immunostaining the cells for markers specific for each stage (e.g., podocyte progenitors, immature podocytes, or mature podocytes) as described earlier.

In some embodiments, the mesodermal cells and/or intermediate mesodermal cells can be derived or produced from a population of pluripotent stem cells. Methods for differentiating pluripotent stem cells into mesodermal cells and/or intermediate mesodermal cells are known in the art, for example, as described in International Patent Application Nos.: WO 2011/115308, WO 2012/011610, and WO 2013/094771, the contents of each of which are incorporated herein by reference.

In some embodiments, the mesodermal cells can be derived from pluripotent stem (PS) cells by contacting a population of pluripotent stem cells with a serum-free first mesoderm differentiation medium comprising activin A and an inhibitor of glycogen synthase kinase 3 (GSK-3) or an activator of Wnt signaling pathway. In some embodiments, the pluripotent stem cells can be contacted with the first mesoderm differentiation medium for a period of time until at least a portion of the cells display one or more mesodermal cell-specific marker. Non-limiting examples of mesodermal cell-specific markers include Brachyury, Goosecoid, Snail, Twist-1, Twist-2, Wnt-8a, N-Cadherin, MIXL1 (Mix/Bix paired-like homeodomain protein), GDF-1 (Growth/differentiation factors-1), and a combination of two or more thereof. In some embodiments, the period of time can range from about 12 hours to about 10 days, or about 1 day to about 5 days, or about 1 day to about 3 days, or about 1 day to about 2 days. In some embodiments, the period of time can be no more than 7 days, no more than 6 days, no more than 5 days, no more than 4 days, no more than 3 days, no more than 2 days, no more than 1 day or less.

In some embodiments, the intermediate mesodermal cells can be produced by contacting mesodermal cells or PS cell-derived mesodermal cells with a serum-free second mesoderm differentiation medium comprising BMP and an inhibitor of glycogen synthase kinase 3 (GSK-3) or an activator of Wnt signaling pathway. In some embodiments, the mesodermal cells are contacted with the second mesoderm differentiation medium for a period of time until at least a portion of the mesodermal cells display one or more intermediate mesodermal cell-specific marker. Non-limiting examples of intermediate mesodermal cell-specific markers include OSR1 (Odd-Skipped Related Transcription Factor 1), Pax2 (Paired Box 2), Pax8 ((Paired Box 8), SIX2 (SIX homeobox 2), WT1 (Wilms tumor 1), Cited2 (Cbp/p300-interacting transactivator, with Glu/Asp-rich carboxy-terminal domain, 2), Eya1 (Eyes absent homolog 1), Sall1 (spalt-like transcription factor 1), and a combination of two or more thereof. In some embodiments, the period of time can be at least about 5 days or longer, including, e.g., at least about 10 days, at least about 15 days or longer. In some embodiments, the period of time can range from about 3 days to about 30 days, or about 5 days to about 25 days, or about 10 days to about 20 days, or about 15 days to about 20 days. In some embodiments, the period of time can be no more than 3 weeks, no more than 2 weeks, or no more than 1 week.

In another aspect, a method of generating a population of podocytes is provided herein. The method comprises: (a) contacting a population of pluripotent cells with a serum-free first mesoderm differentiation medium comprising activin A and an inhibitor of glycogen synthase kinase 3 (GSK-3) or an activator of Wnt signaling pathway; (b) contacting a population of cells from step (a) with a serum-free second mesoderm differentiation medium comprising BMP and an inhibitor of glycogen synthase kinase 3 (GSK-3) or an activator of Wnt signaling pathway; and (c) contacting a population of cells from step (b) with a serum-free podocyte induction medium as described herein (for example, comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid). The method produces a population of cells that comprises an increased percentage of podocytes, as compared to the cells from step (b) not contacted with the podocyte induction medium.

The method produces a population of cells that comprises an increased percentage of podocytes, e.g., by at least about 30% or more, including, e.g., at least about 40%, at least about 50%, at least about 60%, at least about 70%, at least about 80%, at least about 90%, or more, as compared to the pluripotent stem cells not contacted with the podocyte induction medium. In some embodiments, the method can produce a population of cells that comprises an increased percentage of podocytes, e.g., by at least about 1.1-fold or more, including, e.g., at least about 1.5-fold, at least about 2-fold, at least about 3-fold, at least about 4-fold, at least about 5-fold, at least about 10-fold, or more, as compared to the pluripotent stem cells not contacted with the podocyte induction medium.

In some embodiments, at least about 70% or higher, including, e.g., at least about 80%, at least about 90%, at least about 95%, or more (up to 100%) of the pluripotent stem cells can be differentiated into podocytes.

In some embodiments, the contact period of time in step (a) can range from about 12 hours to about 10 days, or about 1 day to about 5 days, or about 1 day to about 3 days, or about 1 day to about 2 days. In some embodiments, the contact period of time in step (a) can be no more than 7 days, no more than 6 days, no more than 5 days, no more than 4 days, no more than 3 days, no more than 2 days, no more than 1 day or less.

In some embodiments, the contact period of time in step (b) can range from about 3 days to about 30 days, or about 5 days to about 25 days, or about 10 days to about 20 days, or about 15 days to about 20 days. In some embodiments, the contact period of time in step (b) can be at least about 5 days or longer, including, e.g., at least about 10 days, at least about 15 days or longer. In some embodiments, the contact period of time in step (b) can be no more than 3 weeks, no more than 2 weeks, or no more than 1 week.

In some embodiments, the contact period of time in step (c) can range from about 12 hours to about 20 days, or about 1 day to about 15 days, or about 2 days to about 10 days, or about 3 days to about 5 days. In some embodiments, the contact period of time in step (c) can be at least about 5 days, at least about 10 days, at least about 12 days, at least about 14 days or longer. In some embodiments, the contact period of time in step (c) can be no more than 7 days, no more than 6 days, no more than 5 days, or less. In one embodiment, the contact period of time in step (c) can vary from about 5 days to about 15 days. The contact period of time in step (c) can vary depending on, e.g., differentiation rate of the cells and/or subsequent use of the differentiated cells. For example, in some embodiments, if the differentiated cells were to be used for transplantation, it can be desirable that the cells from step (b) can be contacted with the podocyte induction medium for a shorter period of time such that they are not fully differentiated into post-mitotic podocytes, and can integrate better with other cells upon transplantation. In these embodiments, the contact period of time can range from about 12 hours to about 3 days, or about 1 day to about 2 days. Accordingly, in some embodiments, the cells from step (b) can be contacted with the podocyte induction medium until at least a portion of the cells display one or more podocyte-specific marker (e.g., but not limited to, nephrin). In some embodiments, the cells from step (b) can be contacted with the podocyte induction medium until the cells reach a desirable differentiation stage (e.g., podocyte progenitors or precursor cells, immature podocytes, or mature podocytes). In some embodiments, the cells from step (b) can be contacted with the podocyte induction medium until the cells differentiate into post-mitotic podocytes. The optimum period of time for each differentiation stage can be determined, for example, by immunostaining the cells for markers specific for each stage (e.g., podocyte progenitors, immature podocytes, or mature podocytes). For example, immature (mitotic) differentiated podocytes can be characterized by expression of at least one or more of intermediate mesodermal cell-specific markers (e.g., but not limited to, OSR1, OSR2, and PAX2) and at least one or more of podocyte-specific markers (e.g., but not limited to, WT1, nephrin, podocin, podocalyxin, synaptopodin, and APOL1). Mature (post-mitotic) differentiated podocytes can be characterized by absence of at least one (including, e.g., at least two, at least three or more) or all intermediate mesodermal cell-specific markers (e.g., but not limited to, PAX2, OSR1, and OSR2), and expression of at least one or more podocyte-specific markers (e.g., but not limited to, WT1, nephrin, podocin, podocalyxin, synaptopodin, and APOL1).

The cell populations cultured according to the methods of various aspects described herein can be monitored to assess changes in the cells imparted by culturing (e.g., during one or more time points in the culture method disclosed herein) so as to characterize the cell population produced. The expression of certain markers can be determined by detecting the presence or absence of the marker transcript or protein expression. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art.

Other methods which are known in the art can also be used to quantitate marker gene expression. For example, the expression of a marker gene product can be detected by using antibodies specific for the marker gene product of interest by e.g. FACS analysis or immunocytochemistry. In certain processes, the expression of marker genes characteristic of the cell population of interest as well as the lack of significant expression of marker genes characteristic of pluripotent stem cells and other cell types can be determined.

First mesoderm differentiation medium: In some embodiments of the methods of various aspects described herein, the first mesoderm differentiation medium can be prepared from a basal culture medium supplemented with at least activin A, and a GSK-3 inhibitor or an activator of Wnt signaling pathway.

In the methods of various aspects described herein, the concentrations of each individual component in the first mesoderm differentiation medium can vary from ng/mL to mg/mL or from nM to µM.

In some embodiments, the concentration of the activin A can range from about 50 ng/mL to about 500 ng/mL or from about 75 ng/mL to about 250 ng/mL, or from about 75 ng/mL to about 150 ng/mL, or from about 90 ng/mL to about 110 ng/mL. In one embodiment, the concentration of the activin A is about 100 ng/mL.

In some embodiments, the concentration of the inhibitor of GSK-3 or an activator of Wnt signaling pathway can range from about 0.1 µM to about 10 µM, or from about 0.5 µM to about 5 µM, or from about 1 µM to about 5 µM. In one embodiment, the concentration of the inhibitor of GSK-3 or an activator of Wnt signaling pathway is about 3 µM.

In some embodiments, the first mesoderm differentiation medium can further comprise a Rho-associated protein kinase (ROCK) inhibitor, e.g., at a concentration ranging from about 1 µM to about 20 µM. Example Rho-associated protein kinase (ROCK) inhibitors include, but are not limited to, Y27632, HA-100, H-1152, (+)-trans-4-(1-aminoethyl)-1-(pyridin-4-ylaminocarbony I) cyclohexane dihydro-chloride monohydrate (described in WO0007835 L WO00057913), imidazopyridine derivatives (described in U.S. Pat. No. 7,348,339), substituted pyrimidine and pyridine derivatives (described in U.S. Pat. No. 6,943,172) and substituted isoquinoline-sulfonyl compounds (described in EP00187371), or GSK429286A, or Thiazovivin, or an analog or derivative thereof. In one embodiment, the ROCK inhibitor can be added to the first mesoderm differentiation medium to reach a final concentration of about 10 µM.

In some embodiments, the first mesoderm differentiation medium can further comprise B27 supplement as defined herein.

In some embodiments, the first mesoderm differentiation medium can further comprise glutamine or a derivative thereof. In some embodiments, the glutamine can be a stabilized form of L-glutamine and/or L-alanyl-L-glutamine.

In one embodiment, the first mesoderm differentiation medium is DMEM/F12 basal medium supplemented with activin A, a GSK-3 inhibitor (e.g., CHIR99021) or an activator of Wnt signaling pathway, a ROCK Inhibitor (e.g., Y27632), B27 supplement, and optional antibiotics (e.g., Penicillin-Streptomycin).

Individual components in the first mesoderm differentiation medium can each be independently present in solution (e.g., in a soluble form) or be immobilized on a biomaterial substrate in which the cells are cultured. In some embodiments, the immobilized component can form a gradient or uniform distribution.

Second mesoderm differentiation medium: In some embodiments of the methods of various aspects described herein, the second mesoderm differentiation medium can be prepared from a basal culture medium supplemented with at least BMP, and a GSK-3 inhibitor or an activator of Wnt signaling.

In the methods of various aspects described herein, the concentrations of each individual component in the second mesoderm differentiation medium can vary from ng/mL to mg/mL or from nM to µM.

In some embodiments, the concentration of the inhibitor of GSK-3 or an activator of Wnt signaling pathway can range from about 0.1 µM to about 10 µM, or from about 0.5 µM to about 5 µM, or from about 1 µM to about 5 µM. In one embodiment, the concentration of the inhibitor of GSK-3 or an activator of Wnt signaling pathway is about 3 µM.

In some embodiments, the concentration of the BMP can range about 50 ng/mL to about 500 ng/mL or from about 75 ng/mL to about 250 ng/mL, or from about 75 ng/mL to about 150 ng/mL, or from about 90 ng/mL to about 110 ng/mL. In one embodiment, the concentration of the BMP is about 100 ng/mL.

In some embodiments, the second mesoderm differentiation medium can further comprise B27 supplement as defined herein.

In some embodiments, the first mesoderm differentiation medium can further comprise glutamine or a derivative thereof. In some embodiments, the glutamine can be a stabilized form of L-glutamine and/or L-alanyl-L-glutamine.

In one embodiment, the second mesoderm differentiation medium is DMEM/F12 basal medium supplemented with BMP (e.g., BMP-7), a GSK-3 inhibitor (e.g., CHIR99021) or an activator of Wnt signaling pathway, B27 supplement, and optional antibiotics (e.g., Penicillin-Streptomycin).

Individual components in the second mesoderm differentiation medium can each be independently present in solution (e.g., in a soluble form) or be immobilized on a biomaterial substrate in which the cells are cultured. In some embodiments, the immobilized component can form a gradient or uniform distribution.

The pluripotent stem cells, mesodermal cells, and/or intermediate mesodermal cells in the methods of various aspects described herein can be cultured in any appropriate mode, including, e.g., adherent cultures (2-dimensional or 3-dimensional), suspension cultures (e.g., non-adherent cultures), scaffold cultures, or a combination of two or more thereof. The optimum or appropriate mode of cell culture can be determined on an experimental basis. Without wishing to be bound by theory, cell differentiation methods that are based on adherent cultures are generally more likely to produce a desired cell population at higher yields than suspension cultures.

In some embodiments of this aspect and other aspects described herein, the pluripotent stem cells, mesodermal cells, and/or intermediate mesodermal cells can be cultured under an adherent condition during the contacting step. As used herein, culturing under "adherent conditions" it is meant culturing under conditions that promote adhesion of cells to a surface of a cell or tissue culture device or vessel in which they are cultured (e.g., a surface of a transwell, microwell, or a microchannel) or to a surface of a cell culture scaffold with which they are in contact (e.g., a gel scaffold). In some instances, cells may be induced to adhere to a surface simply by keeping the culture stationary. In some instances, a surface to which it is desirable to promote adhesion can be coated with one or more extracellular matrix molecules, including, e.g., but not limited to, fibronectin, laminin, poly-lysine, collagen, vitronectin, hyaluronic acid, peptides, gelatin, matrigel, or a combination of two or more.

Figure 10A:
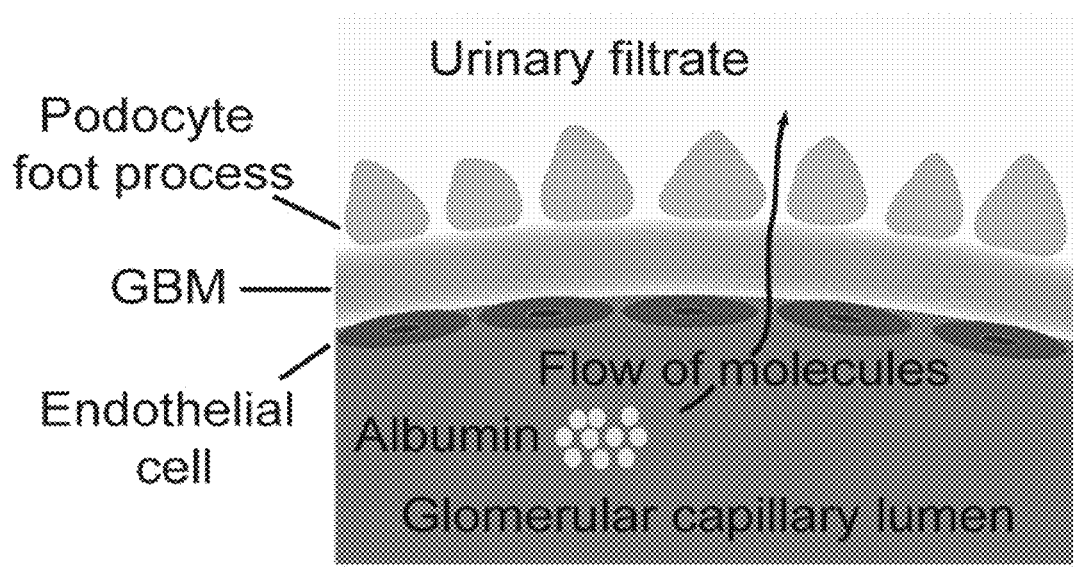
Figure 10B:
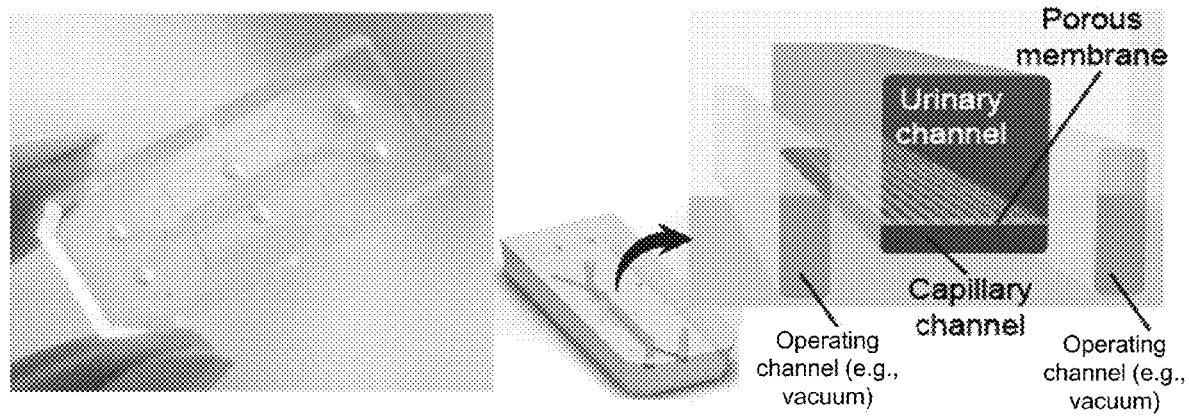

In some embodiments of this aspect and other aspects described herein, the pluripotent stem cells, mesodermal cells, and/or intermediate mesodermal cells can be subjected to a mechanical strain and/or shear stress during and/or after the differentiation process. For example, a fluid (e.g., an appropriate medium depending on the stage of the differentiation process) can be continuously flown over the cells at a flow rate that generates a physiologically-relevant shear stress to the cells during and/or after the differentiation process. By way of example only, in some embodiments, a fluid (e.g., an appropriate medium depending on the stage of the differentiation process) can be continuously flown over the cells at a flow rate that generates a shear stress of at least about 0.00001 dyne/$cm^2$ or higher, including, e.g., at least about 0.0001 dyne/$cm^2$, at least about 0.001 dyne/$cm^2$, or higher. In some embodiments, a fluid (e.g., an appropriate medium depending on the stage of the differentiation process) can be continuously flown over the cells at a flow rate that generates a shear stress of about 0.00001 dyne/cm$^2$ to about 0.1 dyne/cm$^2$ or about 0.0001 dyne/cm$^2$ to about 0.01 dyne/cm$^2$. In some embodiments where podocyte differentiation is performed in an organ-on-a-chip device (including, e.g., the one as shown in FIG. 10B), the volumetric flow rates applied to both channels can be the same or different. When the same volumetric flow rate is applied to both channels, the shear stress applied to the cells in both channels can be the same or different, depending on the size of the channels. For example, as shown in Example 3, when the fluid was flowed at a rate of about 60 μL/hr in both the top and bottom channels of the organ-on-a-chip device, this corresponds to a shear stress of about 0.00068 dyne/cm$^2$ for the top (podocyte) channel and a shear stress of about 0.017 dyne/cm$^2$ for the bottom channel that mimics a capillary with or without endothelial cells. The levels of the shear stress can be further tuned to influence cell differentiation and/or function. It should be noted that in some embodiments, the chamber dimensions (e.g., heights and/or widths) of a cell culture device can be varied to achieve different levels of fluid shear stress, which can influence cell differentiation and/or cell function.

In some embodiments, the cells can be periodically stretched or compressed during and/or after the differentiation process. Static or cyclic mechanical strain can be applied to the cells. By way of example only, in one embodiment, a cyclic strain at about 1 hertz and 10% stretch can be applied during and/or after the differentiation process. The frequency and/or degree of mechanical strain applied to cells can be differentially tuned to influence cell differentiation and/or function. While mechanical strain is not necessary, application of mechanical strain to differentiated podocytes can enhance extension of podocyte foot processes. Thus, mechanical force can be applied during or after podocyte differentiation using the methods described herein to facilitate interactions between podocytes and endothelial cells or any other cell type, e.g., when in a co-culture, thereby modulating tissue development and function.

As used herein, the term "mechanical strain," when use in connection with cells, generally refers to deformation of cells or changes in cell shape resulting from externally applied mechanical stresses. Methods and devices to deform cells are known in the art and can be used herein. In some embodiments, the cell culture devices as described in International Pat. App. No. WO 2015/138034 and WO/2015/138032; and in U.S. Pat. No. 8,647,861, the contents of each of which are incorporated herein by reference in their entirety, can be used to perform the differentiation process and subject the cells to a controllable mechanical strain.

In some embodiments of this aspect and other aspects described herein, the pluripotent stem cells, mesodermal cells, and/or intermediate mesodermal cells can be co-cultured with another cell types such as endothelial cells (e.g., glomerular endothelial cells). In some embodiments, the pluripotent stem cells, mesodermal cells, and/or intermediate mesodermal cells and another cell types such as endothelial cells can be co-cultured in individual chambers separated by a fluid-permeable structure (e.g., a porous membrane). In these embodiments, while not necessary, application of mechanical strain to the pluripotent stem cells, mesodermal cells, and/or intermediate mesodermal cells can enhance extension of differentiated podocyte foot processes through the fluid-permeable structure and interact with another cell type cultured on the other side of the fluid-permeable structure. For example, FIG. 10F shows application of mechanical strain to hiPS-derived podocytes can enhance extension of podocyte foot processes through the porous membrane of an organ-on-a-chip device and interact with glomerular endothelial cells cultured on the other side of the membrane.

While not necessary, it can be desirable to have cell culture environment mimic the physiological microenvironment of a kidney or glomerulus, and/or to promote cell adhesion to a substrate surface. Accordingly, in some embodiments, the pluripotent stem cells, mesodermal cells, intermediate mesodermal cells, and/or differentiated podocytes can be cultured on a surface coated with at least one or more (e.g., at least two or more, including, at least three, at least four or more) extracellular matrix proteins. Non-limiting examples of extracellular matrix include, but are not limited to, laminin, collagen, fibronectin, vitronectin, hyaluronic acid, peptides, gelatin, matrigel, decellularized matrix, and a combination of two or more thereof. In some embodiments, the pluripotent stem cells, mesodermal cells, and/or intermediate mesodermal cells can be cultured on a surface coated with laminin and/or collagen (e.g., but not limited to collagen I). Examples of laminin that can be used to coat a surface for cell differentiation and/or culture include, but are not limited to laminin-511, a fragment of laminin-511 (e.g., laminin 511-E8), laminin 521 (also known as laminin 11), or a combination of two or more thereof.

In some embodiments, the pluripotent stem cells, mesodermal cells, and/or intermediate mesodermal cells can be cultured on a surface coated with decellularized matrix. As used herein, the term "decellularized matrix" refers to a composition derived from or generated by removing the cellular components of an isolated population of cells or tissues without any significant damage to the extracellular matrix. In some embodiments, the decellularized matrix can be derived from glomerular endothelial cells (e.g., human glomerular endothelial cells). In some embodiments, the decellularized matrix can be derived from podocytes. In some embodiments, the decellularized matrix can be derived from a tissue, e.g., but not limited to a kidney tissue.

In some embodiments of this aspect and other aspects described herein, the pluripotent stem cells, mesodermal cells, intermediate mesodermal cells, and/or podocytes can be cultured under a non-adherent condition, e.g., a suspension. As used herein, culturing under "non-adherent conditions" it is meant culturing under conditions that suppress adhesion of cells to a surface of a cell or tissue culture device or vessel in which they are cultured (e.g., a surface of a transwell, microwell, or a microchannel) or to a surface of a cell culture scaffold with which they are in contact (e.g., a biomaterial scaffold). In some instances, cells may be maintained in a non-adherent state by agitating the culture. In some instances, a surface to which it is desirable to suppress adhesion can be coated with one or more anti-adhesion molecules, including, e.g., but not limited to, agarose, polyhydroxyethyl methacrylate (poly-HEMA), and/or anti-integrin molecules.

In some embodiments of this aspect and other aspects described herein, the pluripotent stem cells, mesodermal cells, intermediate mesodermal cells, and/or podocytes can be embedded in a biomaterial scaffold during the contacting step. For example, biomaterials such as, but not limited to, silk fibroin, polyethylene oxide (PEO), polyethylene glycol (PEG), fibronectin, keratin, polyaspartic acid, polylysine, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, and/or other biocompatible polymers, can be used as a scaffold material during the contacting step.

In some embodiments of the methods described herein where multi-stages of cell cultures are involved, cells in each stage can be independently cultured in the same culture mode (e.g., adherent, suspension, or scaffold), or in different culture modes (e.g., adherent, suspension, or scaffold). For example, in one embodiment, all steps (a)-(c) of the methods described herein can be performed under adherent conditions. In another embodiment, one of the steps (a)-(c) of the differentiation methods described can be performed under non-adherent condition while the other steps can be performed under adherent conditions.

The culture temperature of the differentiation methods described herein ranges from about 30° C. to 40° C., preferably about 37° C., but the temperature is not limited thereto. Cell culture is carried out under an atmosphere containing air/$CO_2$. The $CO_2$ concentration can ranges from about 2% to about 5%.

The pluripotent stem cells, mesodermal cells, and/or intermediate mesodermal cells used in the methods of various aspects described herein can be of any species, including, e.g., mammalian cells (for example, without limitation; primate, and human) and any animal of interest, including without limitation; mouse, hamster, rabbit, dog, cat, transgenic animal domestic animals, such as equine, bovine, murine, ovine, canine, feline, etc. In some embodiments of this aspect and other aspects described herein, the pluripotent stem cells, mesodermal cells, and/or intermediate mesodermal cells can be human cells.

The cells can also be cultured cells, e.g. in vitro or ex vivo. For example, cells cultured in vitro in a culture medium. Alternatively, for ex vivo cultured cells, cells can be obtained from a subject, where the subject is healthy and/or affected with a kidney or glomerular disease or disorder. Cells can be obtained, as a non-limiting example, by biopsy or other surgical means know to those skilled in the art.

The methods of various aspects described herein generally can efficiently generate podocytes from the pluripotent stem cells, mesodermal cells and/or intermediate mesodermal cells. For example, the methods of various aspects described herein can induce differentiation of at least about 80% or more (up to 100%) of the pluripotent stem cells, mesodermal cells and/or intermediate mesodermal cells into podocytes. Accordingly, while not necessary, in some embodiments where it is desirable to generate a substantially pure population of podocytes, the methods of various aspects described herein can further comprise selecting the podocytes upon the contacting step. Stated another way, in some embodiments, the population of podocytes can be further enriched, isolated and/or purified, e.g. by using an affinity tag (e.g., anti-WT1, anti-nephrin, anti-podocin, anti-APOL1, and/or anti-synaptopodin antibody) and/or FACS sorting. Additionally or alternatively, podocyte-specific markers (e.g., nephrin) or live-cell mRNA probes (See Bao et al., Fluorescent probes for live-cell RNA detection, Annu Rev. Biomed. Engin. 2009, 11: 25-47; and Ricardo and Vaca J. Nucleic acids vol. 2011: Article ID 741723: 1-15) can be used for selection of podocytes.

In some embodiments, a substantially pure population of podocytes can be obtained by selecting differentiated cells for at least one or more of the following criteria:
 a. the podocytes are substantially negative for a pluripotency marker;
 b. the podocytes are substantially positive for at least one or more podocyte-specific marker(s), including, e.g., nephrin, WT1, and/or podocin (e.g., the expression level of the podocyte-specific marker(s) is comparable to or greater than a reference level, e.g., corresponding to the level present in mature podocytes in vivo or established podocyte cell lines);
 c. the podocytes are substantially negative for a progenitor cell marker (including, e.g., but not limited to Pax-2 and/or OSR-1 (odd-skipped related transcription factor protein 1);
 d. the podocytes are substantially incapable of proliferation (e.g., terminally differentiated cells); and
 e. the podocytes have a size ranging from about 30 μm to about 90 μm, when they are dissociated or non-adherent, or are in suspension.

As used herein, the term "substantially incapable of proliferation" refers to cells that are prevented from undergoing cell division. When the term is used in connection with a population of cells, it can mean that at least about 70% or more, including, e.g., at least about 80%, at least about 90%, at least about 95% or more (including up to 100%) of the total cell population do not undergo cell division. Cell division generally involves active DNA synthesis. Thus, undetectable or no incorporation of EdU, BrdU, or a nucleoside analog of thymidine into DNA of the podocytes after culturing for a period of time is indicative of podocytes that do not undergo cell division.

Podocyte differentiation by any embodiment of the methods described herein can be performed in any cell or tissue culture devices, including, e.g., but not limited to microwells, transwells, tissue culture plates, and/or flasks, microfluidic devices (including, e.g., but not limited to organ-on-a-chip devices), and any combinations thereof. In some embodiments, all stages of differentiation process from undifferentiated pluripotent stem cells to podocytes can be performed in the same cell culture device. In some embodiments, one or more stages of differentiation process from undifferentiated pluripotent stem cells to podocytes can be performed in one cell culture device, and the cells can then be transferred to another cell culture device (e.g., for the same or different format) to complete podocyte differentiation. By way of example only, in some embodiments, mesoderm differentiation (e.g., differentiation of undifferentiated pluripotent stem cells into mesoderm cells) and/or intermediate mesoderm differentiation (e.g., differentiation of undifferentiated pluripotent stem cells or mesoderm cells to intermediate mesoderm cells) can be performed in a non-organ-on-a-chip device (e.g., a microplate), and the cells can then be transferred to an organ-on-a-chip device to undergo podocyte differentiation using the podocyte induction media described herein. In some embodiments, undifferentiated human iPS cells can be differentiated to intermediate mesoderm stage in a cell culture device other than an organ-on-a-chip device, and the cells are then seeded into an organ-on-a chip device to induce podocyte differentiation using one or more embodiments of the podocyte induction medium described herein.

Upon podocyte differentiation, the podocytes can be cultured or maintained in any art-recognized cell cultured medium that is used to maintain podocytes. For example, a cell culture medium from Cell Systems, Catalog No. 4Z0-500-R, can be used to culture and maintain podocytes after differentiation. In some embodiments, the podocyte differentiation medium can be used or modified to culture and maintain podocytes.

Cells Produced by the Differentiation Methods Described Herein and Compositions Comprising the Same Isolated populations of podocytes produced by the methods of any aspects described herein are also provided.

In some embodiments, the podocytes do not express any of pluripotency markers known by one of ordinary skill in the art, including but not limited to Alkaline Phosphatase, SSEA3, SSEA4, Sox2, Oct3/4, Nanog, T AI60, TRA I81, TDGF 1, Dnmt3b, FoxD3, GDF3, Cyp26al, TERT, and zfp42.

In some embodiments, the podocytes can be post-mitotic (mature) podocytes. Mature (post-mitotic) differentiated podocytes are substantially negative for at least one or more (including, e.g., at least two, at least three or more) intermediate mesodermal cell-specific markers described herein (e.g., but not limited to, PAX2, OSR1, and OSR2), and substantially positive for at least one or more (including, e.g., at least two, at least three or more) podocyte-specific markers described herein (e.g., but not limited to, WT1, nephrin, podocin, podocalyxin, synaptopodin, and APOL1). In some embodiments, mature (post-mitotic) differentiated podocytes can be substantially negative for PAX2, OSR1, and OSR2; and substantially positive for WT1, nephrin, podocin, podocalyxin, synaptopodin, and APOL1.

In some embodiments, the podocytes can be immature podocytes. Immature (mitotic) differentiated podocytes can express at least one or more (including, e.g., at least two, at least three or more) intermediate mesodermal cell-specific markers described herein (e.g., but not limited to, OSR1, OSR2, PAX2, or a combination of two or more). Further, they can express one or more podocyte-specific markers described herein (e.g., but not limited to, WT1, nephrin, podocin, podocalyxin, synaptopodin, and APOL1).

In some embodiments, the isolated population of podocytes can comprise at least 80%, at least 90%, at least 95%, or up to 100% of podocytes.

In some embodiments, the podocytes can comprise at least one or more genetic modifications. In some embodiments, the podocytes can be genetically modified or engineered to express at least one or more mesodermal-specific reporters (e.g., but not limited to, fluorescently-labeled Brachyury, Goosecoid, SNAIL, TWIST-1, TWIST-2, WNT-8a, N-Cadherin, MIXL1, or GDF-1); kidney-specific reporters (e.g., but not limited to, fluorescently-labeled Wilm's tumor protein 1 (WT1), GDNF (glial cell derived neurotrophic factor), RET (ret proto-oncogene), WNT4 (wingless-type MMTV integration site family, member 4), CDH16 (cadherin 16, KSP-cadherin), CLCN5 (chloride channel, voltage-sensitive 5), CYP27/CYP27A1 (Cytochrome P450, Family 27, Subfamily A, Polypeptide), or SLC12A1 (solute carrier family 12 (sodium/potassium/chloride transporter), member 1); podocyte-specific reporters (e.g., but not limited to fluorescently-labeled nephrin, Apolipoprotein L1 (APOL1), alpha-actinin 4, podocin, podocalyxin, WT1, and synaptopodin), or a combination of two or more thereof. In some embodiments, the podocytes can be genetically modified or engineered to correct or introduce defect(s) or mutation(s) in podocyte genes (e.g., but not limited to nephrin, WT1, APOL1, alpha-actinin 4, podocin, podocalyxin, synaptopodin, and a combination of two or more thereof).

In some embodiments, the differentiated podocytes can be larger in size than undifferentiated pluripotent stem cell, mesodermal cell, and/or intermediate mesodermal cells, e.g., by at least 50% or more, including, e.g., at least 60%, at least 70%, at least 80%, at least 90%, at least 95% or more. In some embodiments, the differentiated podocytes can be larger in size than undifferentiated pluripotent stem cell, mesodermal cell, and/or intermediate mesodermal cells, e.g., by at least 1.1-fold or more, including, e.g., at least 1.5-fold, at least 2-fold or more. In some embodiments, the differentiated podocytes can have a cell size ranging from about 30 µm to about 90 µm, or about 40 µm to about 70 µm, when they are dissociated (e.g., non-adherent) or in a suspension. As the podocytes attach and spread on a surface (e.g., a solid substrate surface with or without extracellular matrix proteins), the cells can be larger in size, e.g., up to about 250 µm or higher.

In some embodiments, the podocytes can exhibit an increased uptake of exogenous albumin, e.g., by at least about 10% or more, including, e.g., at least 20%, at least 30%, at least 40%, at least 50%, at least 60%, at least 70%, at least 80%, at least 90%, at least 95% or more, as compared to mature podocytes naturally occurring in vivo or immortalized podocytes. In some embodiments, the podocytes can exhibit an increased uptake of exogenous albumin, e.g., by at least about 1.1-fold or more, including, e.g., at least 1.5-fold, at least 2-fold, at least 3-fold, at least 4-fold, at least 5-fold, at least 10-fold, or more, as compared to mature podocytes naturally occurring in vivo or immortalized podocytes. In these embodiments, the podocytes express receptors for IgG and albumin transport. Methods to measure cell uptake of an exogenous molecule are known in the art and also described in the Examples herein, e.g., using fluorescently labeled albumin.

In some embodiments, upon injection of the podocytes into a kidney tissue, the podocytes can migrate and localize into glomerular structures of the kidney tissue more efficiently than mature podocytes naturally occurring in vivo or immortalized human podocyte cell line, e.g., by at least 30% or more, including, e.g., at least 40%, at least 50%, at least 60%, at least 70%, at least 80%, at least 90%, at least 95% or more. In some embodiments, upon injection of the podocytes into a kidney tissue, the podocytes can migrate and localize into glomerular structures of the kidney tissue more efficiently than mature podocytes naturally occurring in vivo or immortalized human podocyte cell line, e.g., by at least about 1.1-fold or more, including, e.g., at least 1.5-fold, at least 2-fold, at least 3-fold, at least 4-fold, at least 5-fold, at least 10-fold, or more. An exemplary method to assess such capability of podocytes is described in Example 2.

One aspect provided herein relates to a synthetic tissue scaffold comprising a cell-compatible biopolymer and an isolated population of podocytes distributed therein, wherein the isolated population of podocytes is produced by the methods of any aspects described herein.

Non-limiting examples of a cell-compatible biopolymer include, but are not limited to, silk fibroin, polyethylene oxide (PEO), polyethylene glycol (PEG), fibronectin, keratin, polyaspartic acid, polylysine, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, and/or other biocompatible polymers.

In some embodiments, the synthetic tissue scaffold can further comprise one or more kidney-associated cells. The kidney-associated cells can be distributed in the biopolymer. Non-limiting examples of kidney-associated cells include, but are not limited to, endothelial cells, mesangial cells, epithelial cells, smooth muscle cells or myocytes, granular cells (Juxtaglomerular cells), parietal cells, proximal tubular cells, loop of Henle thin segment cells, duct cells, connective tissue fibroblasts, pericytes, insulin-producing cells, and a combination of two or more thereof.

Another aspect described herein relates to a biological ink comprising the isolated population of podocytes described herein mixed with a viscous extracellular matrix for use in a 3-D printer. In some embodiments, the isolated population of podocytes described herein can be mixed with a viscous gelatin to form a biological ink of podocytes. The resulting biological ink can be fed into a 3-D printer, which is programmed to arrange different cell types, along with other materials, into a precise three-dimensional shape.

Certain other aspects described herein relate to compositions, such as cell cultures or cell populations, comprising podocytes generated by the methods described herein. In some embodiments, pluripotent stem cells, and/or mesodermal cells, and/or intermediate mesodermal cells from which the podocytes are derived comprise less than about 25%, less than about 20%, less than about 15%, less than about 10%, less than about 5%, less than about 4%, less than about 3%, less than about 2%, less than about 1%, or less than 0.5% of the total cells in the culture.

Some other aspects described herein relate to compositions, such as cell cultures or cell populations, produced by the methods described herein and which comprise podocytes as the majority cell type. In some embodiments, the methods described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% podocytes. In some embodiments, pluripotent stem cells, and/or mesodermal cells, and/or intermediate mesodermal cells from which the podocytes are derived comprise less than about 25%, less than about 20%, less than about 15%, less than about 10%, less than about 5%, less than about 4%, less than about 3%, less than about 2%, less than about 1%, or less than 0.5% of the total cells in the culture or population. In some embodiments, the cells of the cell cultures or cell populations comprise human cells.

Methods of Modeling a Kidney-Specific Condition in vitro

Podocytes (e.g., immature or mature) produced by the methods of various aspects described herein can be used in different applications where podocytes are required, including, e.g., but not limited to, as an in vitro model for a kidney/glomerular disorder, therapeutic applications (e.g., tissue regeneration and/or repair or transplantation), drug discovery and/or developments, and/or tissue engineering. In one aspect, a method of modeling a kidney-specific condition in vitro is provided herein. The method comprises culturing in a cell or tissue culture device the isolated population of podocytes described herein. In some embodiments, the podocytes can be post-mitotic podocytes.

The podocytes can be cultured in any cell or tissue culture device selected to suit the need of an application. Examples of a cell or tissue culture device include, but are not limited to, a transwell, a microwell, a microfluidic device, a bioreactor, a culture plate, or any combinations thereof.

In some embodiments, the methods described herein can be performed in a microfluidic device. In one embodiment, the microfluidic device can be an organ-on-a-chip device. Examples of various organ-on-a-chip devices, e.g., as described in International Patent Application Nos: WO 2010/009307, WO 2012/118799, WO 2013/086486, WO 2013/086502, WO 2015/138034, WO2015/138032, and in U.S. Pat. No. 8,647,861, the contents of each of which are incorporated herein by reference in their entireties, can be utilized to culture the podocytes described herein for modeling a kidney-specific condition in vitro. In one embodiment, the organ-on-a-chip device can comprise a first channel and a second channel separated by a membrane. The membrane can be porous (e.g., permeable or selectively permeable), non-porous (e.g., non-permeable), rigid, flexible, elastic, or any combination thereof. In some embodiments, the membrane can be porous, e.g., allowing exchange/transport of fluids (e.g., gas and/or liquids), passage of molecules such as nutrients, cytokines and/or chemokines, cell transmigration, or any combinations thereof. In some embodiments, the membrane can be non-porous. In some embodiments, a first surface of the membrane facing the first channel comprises the podocytes adhered thereon. In some embodiments, a second surface of the membrane facing the second channel can comprise kidney capillary endothelial cells or glomerular endothelial cells adhered thereon.

The podocytes can be pre-formed and then transferred to the cell or tissue culture device for modeling a kidney-specific condition in vitro, or they have been differentiated in the cell or tissue culture device from pluripotent stem cells, mesodermal cells and/or intermediate mesodermal cells using the differentiation methods of various aspects described herein, prior to the culturing.

For example, in some embodiments, the podocyte differentiation processes can be performed in a suitable cell culture device, including, e.g., but not limited to microwells, transwells, tissue culture plates and/or flasks, microfluidic devices, and any combinations thereof. In some embodiments, the podocyte differentiation processes can be performed in a microfluidic device or in an organ-on-a-chip device. In some embodiments, the organ-on-a-chip device can comprise a first chamber (e.g., a channel), a second chamber (e.g., a channel), and a porous membrane separating the first structure and the second structure. The first chamber and the second chamber can be of substantially equal heights or of different heights. FIG. 10B shows an organ-on-a-chip device, in which the first structure (e.g., a channel) and the second structure (e.g., a channel) are of different heights. In some embodiments, the organ-on-a-chip device can further comprise at least one operating channel on either one or both sides of the first and second structures. Pneumatic pressures or vacuum can be applied to the operating channel to cause the membrane flex or stretch. As described earlier, an exemplary organ-on-a-chip device as described in the International Pat. App. No. WO 2015/138034, and WO2015/138032 and/or in U.S. Pat. No. 8,647,861, the contents of each of which are incorporated herein by reference, can be used to produce pluripotent stem cell-derived podocytes and/or to simulate the structure and/or function of a glomerular capillary wall in vivo. The glomerular basement membrane is modeled by a porous membrane that is amenable to functionalization with appropriate extracellular matrix (ECM) protein(s). The first channel and the second channel can be of substantially equal (e.g., within 10% or within 5% or less) heights or of different heights. In some embodiments, the height ratio of the first channel to the second channel can range from about 2:1 to about 10:1. In some embodiments, the height ratio of the first channel to the second channel can be about 5:1. Podocytes are generally larger in size than endothelial cells; thus a higher channel for podocyte culture can provide more space for podocytes to develop. The channel dimensions (e.g., heights and/or widths) can be varied to achieve different levels of fluid shear stress, which can influence cell differentiation and/or cell function.

For example, undifferentiated pluripotent stem cells and/or their derivatives including, e.g., mesoderm or intermediate mesoderm cells can be cultured on one side of a porous membrane of an organ-on-a-chip device facing the first structure (e.g., first channel), while the other side of the membrane facing the second structure (e.g., second channel) can optionally have endothelial cells (e.g., glomerular endothelial cells) cultured thereon. As shown in Example 3, the undifferentiated pluripotent stem cells and/or their derivatives including, e.g., mesoderm or intermediate mesoderm cells, can be contacted with appropriate media at different stages of the differentiation process as described herein under static flow (i.e., no flow) or continuous fluid flow. Application of mechanical strain to the cells during and/or after the podocyte differentiation process is optional. As shown in FIG. 10B, mechanical strain can be applied to cells cultured on a flexible membrane by actuating or mechanically flexing or stretching the membrane, e.g., a PDMS membrane. In some embodiments, vacuum can be applied to the operating channels of the organ-on-a-chip device (e.g., as shown in FIG. 10B) to periodically stretch the membrane, thereby applying mechanical strain to the cells cultured thereon.

To assess the glomerular filtration function of the in vitro organ-on-a-chip device simulating a glomerular capillary wall, albumin and/or inulin can be continuously infused into the second structure (e.g., a channel) of the organ-on-a-chip device, wherein the side of the membrane facing the second structure comprises glomerular endothelial cells cultured thereon, while the other side facing the first structure comprised PS-derived podocytes cultured thereon. The second structure comprising glomerular endothelial cells modeled a "capillary" channel, while the first structure comprising hiPS-derived podocytes modeled a "urinary" channel. Selective retention of albumin in the "capillary" channel and filtration of inulin into the "urinary" channel are indicative of a functional glomerulus simulated in vitro.

The pluripotent stem cells, mesodermal cells, and/or intermediate mesodermal cells can be derived from normal, healthy cells or diseased cells. In some embodiments, the diseased cells can be derived from a subject carrying a kidney and/or glomerular disorder. Examples of a kidney and/or glomerular disorder include, without limitations, podocyte injury, proteinuria, glomerulosclerosis, diabetic nephropathy, chemotherapy-related nephrotoxicity, and a podocytopathy resulting from one or more mutations in podocyte genes (e.g., genes encoding nephrin, WT1, APOL1, alpha-actinin 4, podocin, podocalyxin, synaptopodin, or a combination of two or more thereof).

In some embodiments, diseased podocytes can be differentiated from induced pluripotent stem cells derived from patients carrying a kidney or glomerulus disorder or at least one or more genetic mutations associated with a kidney or glomerulus disorder. The diseased podocytes can then be manipulated, e.g., using genome engineering technologies such as CRISPRs (clustered regularly interspaced short palindromic repeats), to introduce or correct mutations present in the cells.

In some embodiments where normal, healthy podocytes are used, the podocytes can be contacted with an agent that induces the podocytes to acquire at least one phenotypic characteristic associated with a kidney and/or glomerular disorder, thereby modeling a kidney and/or glomerular disorder in vitro. By way of example only, in some embodiments, doxorubicin and/or Adriamycin can be introduced to induce podocytes injury to model a kidney or glomerulus-specific condition in vitro.

Accordingly, the kidney-specific in vitro model described herein can be used to model podocyte defects that result from genetic and/or non-genetic causes.

Methods for Screening Agents for Treatment of a Kidney and/or Glomerular Disorder Not only can an in vitro model of a kidney or glomerulus-specific condition (a normal or diseased condition) be used to elucidate mechanisms of kidney development and/or disease progression, but it can also be employed to advance therapeutic discovery. Accordingly, a method of screening for an agent to reduce at least one phenotypic characteristic of podocytes associated with a kidney and/or glomerular disorder is also provided herein. The method comprises (a) culturing the isolated population of podocytes described herein that display at least one phenotypic characteristic associated with the kidney and/or glomerular disorder; (b) contacting the podocytes with a library of candidate agents; and (c) detecting response of the podocytes to the candidate agents to identify an agent based on detection of the presence of a reduction in the phenotypic characteristic of the podocytes associated with the kidney and/or glomerular disorder.

The candidate agents can be selected from the group consisting of proteins, peptides, nucleic acids (e.g., but not limited to, siRNA, anti-miRs, antisense oligonucleotides, and ribozymes), small molecules, and a combination of two or more thereof.

Effects of the candidate agents on the podocytes can be determined by measuring response of the cells and comparing the measured response with podocytes that are not contacted with the candidate agents. Various methods to measure cell response are known in the art, including, but not limited to, cell labeling, immunostaining, optical or microscopic imaging (e.g., immunofluorescence microscopy and/or scanning electron microscopy), spectroscopy, gene expression analysis, cytokine/chemokine secretion analysis, metabolite analysis, polymerase chain reaction (PCR), immunoassays, ELISA, gene arrays, spectroscopy, immunostaining, electrochemical detection, polynucleotide detection, fluorescence anisotropy, fluorescence resonance energy transfer, electron transfer, enzyme assay, magnetism, electrical conductivity (e.g., trans-epithelial electrical resistance (TEER)), isoelectric focusing, chromatography, immunoprecipitation, immunoseparation, aptamer binding, filtration, electrophoresis, use of a CCD camera, mass spectroscopy, or any combination thereof. Detection, such as cell detection, can be carried out using light microscopy with phase contrast imaging and/or fluorescence microscopy based on the characteristic size, shape and refractile characteristics of specific cell types.

Methods of Treatment and Pharmaceutical Compositions

In another aspect, the podocytes generated by the differentiation methods described herein and/or synthetic tissue scaffolds described herein can be used for kidney regeneration or as cell-based therapeutics for treatment of a kidney and/or glomerular disorder (including, e.g., but not limited to, podocyte injury, proteinuria, glomerulosclerosis, diabetic nephropathy, chemotherapy-related nephrotoxicity or combinations thereof. Thus, methods of treating a kidney and/or glomerular disorder are also provided herein. In one embodiment, the method comprises transplanting to a subject in need thereof (e.g., suffering from a kidney and/or glomerular disorder) an isolated population of podocytes generated by the differentiation methods of any aspects described herein and/or a synthetic tissue scaffold described herein. As used herein, the term "transplant" or "transplanting" refers to the process of implanting or transferring at least one cell to a subject. The term "transplant" or "transplanting" includes, e.g., autotransplantation (removal and transfer of cell(s) from one location on a patient to the same or another location on the same patient, e.g. after differentiation into podocytes), allotransplantation (transplantation between members of the same species), and xenotransplantation (transplantations between members of different species).

In some embodiments, the podocytes and/or the synthetic tissue scaffold can be transplanted at or in close proximity to a pre-determined location of a kidney of the subject. For example, the podocytes and/or the synthetic tissue scaffold can be transplanted at or in close proximity to a damaged area of a kidney of the subject. The transplanted podocytes can migrate and localize into at least one or more glomerular capillary structure of the kidney tissue, thereby facilitate regeneration and/or repair of the kidney tissue. Example 2 shows that upon microinjection of human iPS-derived podocytes into a kidney tissue, the podocytes migrated and localized into glomerular structures more efficiently than immortalized human podocyte cell line. The ability of human PS-derived podocytes to integrate into the kidney (e.g., developing embryonic kidney, adult kidney, and/or kidney at other developmental stages) and selectively localize to glomerular structures indicates that the cells can be used for tissue/organ regeneration and/or development of cell-based therapeutics.

Podocyte transplantation can be an autologous transplant or an allogeneic transplant. Thus, in some embodiments, the podocytes can be differentiated from pluripotent stem cells derived from somatic cells of the subject to be treated. As used herein, the term "somatic cell" refers to any cell other than a germ cell, a cell present in or obtained from a pre-implantation embryo, or a cell resulting from proliferation of such a cell in vitro. A somatic cell refers to any cells forming the body of an organism, as opposed to germline cells. There are adult somatic cells and embryonic somatic cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

In some embodiments, the podocytes to be transplanted into a subject in need thereof can be differentiated from pluripotent stem cells that were derived from skin fibroblasts of the subject.

In other embodiments, the differentiated podocytes can be allogeneic cells.

Following in vitro cell culture differentiation and optional further isolation as described herein, the podocytes are prepared for implantation. In some embodiments, the cells can be suspended in a compatible carrier, such as cell culture medium or a buffered solution. Those of skill in the art are well versed in determining dose. Cell density can vary from about $10^4$ to about $10^7$ cells/W. The volume of cell suspension to be implanted will vary depending on the site of implantation, treatment goal, and cell density in the solution. Several injections may be used in each host, particularly if the kidney lesion region is large.

In some embodiments, the podocytes can be encapsulated within permeable matrices prior to implantation. Encapsulation provides a barrier to the host's immune system and inhibits graft rejection and inflammation. Several methods of cell encapsulation can be employed. In some instances, podocytes can be individually encapsulated. In other instances, many cells can be encapsulated within the same matrix. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

For administration to a subject, a population of podocytes can be provided in any pharmaceutical composition. These pharmaceutical compositions can comprise a population of cells, formulated together with one or more pharmaceutically acceptable carriers (additives) and/or diluents.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition can further comprise a therapeutic agent, e.g., for treatment of a kidney or glomerulus disorder and/or for promoting regeneration and/or repair of an injured kidney tissue. The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; and substances used for the treatment, prevention, diagnosis, cure or mitigation of a disease or illness; substances which affect the structure or function of the body; or pro-drugs, which become biologically active or more active after they have been placed in a physiological environment.

In some embodiments, the therapeutic agent can comprise an antibiotic, an angiogenic factor, an antimicrobial agent, growth factor, peptide, and combinations thereof.

Kits

Kits for generating a population of podocytes are also provided herein. In some embodiments, the kit comprises: (a) a first container comprising activin A and an inhibitor of glycogen synthase kinase 3 (GSK-3) or an activator of Wnt signaling pathway; a second container comprising bone morphogenetic protein (BMP) and an inhibitor of glycogen synthase kinase 3 (GSK-3) or an activator of Wnt signaling pathway; and (c) a third container comprising (i) activin A, (ii) BMP, (iii) an inhibitor of GSK-3 or an activator of Wnt signaling pathway, (iv) vascular endothelial growth factor (VEGF), and (v) retinoic acid, and wherein the first container, the second container and the third container are each serum-free.

In some embodiments, individual components in the first, second or third container can be in a form of powder, e.g., lyophilized powder. The powder can be reconstituted upon use. In some embodiments, individual components in the first, second or third container can be in a form of liquid.

In some embodiments, the kit can further comprise one or more containers of basal cell culture medium (e.g., in a form of powder or in liquid). The powder can be reconstituted in an aqueous solution (e.g., water) upon use. Examples of cell culture basal media include, but are not limited to, Minimum Essential Medium (MEM), Eagle's Medium, Dulbecco's Modified Eagle Medium (DMEM), Dulbecco's Modified Eagle Medium: Nutrient Mixture F-12 (DMEM F12), F-10 Nutrient Mixture, Ham's F-10 Nutrient Mix, Ham's F12 Nutrient Mixture, Medium 199, RPMI, RPMI 1640, reduced serum medium, basal medium (BME), DMEM/F12 (1:1), and the like, and combinations thereof.

In some embodiments, the kit can further comprise one or more vials of pluripotent stem cells, mesodermal cells and/or intermediate mesodermal cells.

In some embodiments, the kit can further comprise a cell culture device. Examples of a cell culture device include, but are not limited to, a transwell, a microwell, a microfluidic device, a bioreactor, a culture plate, or any combinations thereof. In some embodiments, the kit can further comprise a microfluidic device. In some embodiments, the microfluidic device can be an organ-on-a-chip device. In one embodiment, the organ-on-a-chip device can comprise a first channel and a second channel separated by a membrane, where a first surface of the membrane facing the first channel comprises the podocytes adhered thereon. In some embodiments, a second surface of the membrane facing the second channel can comprise kidney capillary endothelial cells or glomerular endothelial cells adhered thereon. For example, in one embodiment, the organ-on-a-chip device can be a device as described in the International Pat. App. No. WO 2015/138034, and WO2015/138032 and/or in U.S. Pat. No. 8,647,861, the contents of each of which are incorporated herein by reference in their entirety. The first channel and the second channel can be of substantially equal (e.g., within 10% or within 5% or less) heights or of different heights. In some embodiments, the height ratio of the first channel to the second channel can range from about 2:1 to about 10:1. In some embodiments, the height ratio of the first channel to the second channel can be about 5:1. Podocytes are generally larger in size than endothelial cells; thus a higher channel for podocyte culture can provide more space for podocytes to develop.

In some embodiments, the kit can further comprise one or more vials of immortalized podocytes.

In some embodiments, the kit can further comprise one or more containers each containing a detectable label that specifically binds to a pluripotency marker, a podocyte-specific marker, or a progenitor cell marker.

In some embodiments, the kit can further comprise instructions for using the kit to perform generation of podocytes from pluripotent stem cells, mesodermal cells and/or intermediate mesodermal cells.

Podocyte Induction Media

Yet another aspect described herein is a podocyte induction medium for differentiation of pluripotent stem cells, mesodermal cells and/or intermediate mesodermal cells into podocytes. The podocyte induction medium is serum-free and comprises (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid.

In some embodiments, the podocyte induction media can be in a form of powder (e.g., lyophilized powder). The powder can be reconstituted in an aqueous solution (e.g., water) upon use to reach the desired concentrations as described herein.

In some embodiments, the podocyte induction media can be in a form of a liquid. In some embodiments, the concentration of the activin A can range from about 50 ng/mL to about 500 ng/mL. In some embodiments, the concentration of the BMP can range from about 50 ng/mL to about 500 ng/mL. In some embodiments, the concentration of the inhibitor of GSK-3 or the activator of Wnt signaling pathway can range from about 0.1 µM to about 10 µM. In some embodiments, the concentration of the VEGF can range from about 25 ng/mL to about 250 ng/mL. In some embodiments, the concentration of the retinoic acid can range from about 0.01 µM to about 1 µM. Other concentrations of each component in the podocyte induction media described in other aspects described herein are also applicable.

In one embodiment, the podocyte induction medium is DMEM/F12 basal medium supplemented with activin A, BMP (e.g., BMP-7), a GSK-3 inhibitor (e.g., CHIR99021) or an activator of Wnt signaling pathway, VEGF, retinoic acid, B27 supplement, and optional antibiotics (e.g., Penicillin-Streptomycin).

The concentrations of each individual component described herein and throughout the specification are generally the working concentrations for the differentiation methods of various aspects described herein. In some embodiments, the concentrations of each individual component in the podocyte induction medium can be increased, e.g., by 2-fold or more, including, e.g., 3-fold, 4-fold, 5-fold, 6-fold, 7-fold, 8-fold, 9-fold, 10-fold, or higher to create a concentrated podocyte induction medium. A user can dilute the concentrated podocyte induction medium to the working concentrations with an aqueous solution (e.g., sterilized water) upon use. Accordingly, concentrated podocyte induction media is also provided herein.

Embodiments of various aspects described herein can be defined in any of the following numbered paragraphs:

1. A method of generating a population of podocytes comprising:
    contacting a population of pluripotent stem cells with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free, thereby producing a population of cells that comprises an increased percentage of podocytes, as compared to a population of pluripotent stem cells which are not contacted with the podocyte induction medium.
2. The method of paragraph 2, wherein the pluripotent stem cells are contacted with the podocyte induction medium for at least about 3 days or longer.
3. The method of paragraph 1 or 2, wherein the pluripotent stem cells form embryoid bodies and/or organoids prior to or during the contacting step.
4. The method of any of paragraphs 1-3, wherein the pluripotent stem cells are embryonic stem cells.
5. The method of any of paragraphs 1-3, wherein the pluripotent stem cells are induced pluripotent stem cells.
6. A method of generating a population of podocytes comprising:
    contacting a population of mesodermal cells with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free, thereby producing a population of cells that comprises an increased percentage of podocytes, as compared to a population of mesodermal cells which are not contacted with the podocyte induction medium.
7. The method of paragraph 6, wherein the mesodermal cells are produced by contacting a population of pluripotent stem cells with a serum-free first mesoderm differentiation medium comprising activin A and an inhibitor of glycogen synthase kinase 3 (GSK-3) or an activator of Wnt signaling pathway.
8. The method of paragraph 7, wherein the mesodermal cells are contacted with the first mesoderm differentiation medium for a period of about 1 day to about 5 days.
9. The method of paragraph 6, wherein the mesodermal cells are intermediate mesodermal cells.
10. The method of paragraph 9, wherein the intermediate mesodermal cells are produced by contacting mesodermal cells with a serum-free second mesoderm differentiation medium comprising BMP and an inhibitor of glycogen synthase kinase 3 (GSK-3) or an activator of Wnt signaling pathway.
11. The method of paragraph 10, wherein the intermediate mesodermal cells are contacted with the second mesoderm differentiation medium for a period of about 5 days or longer.
12. A method of generating a population of podocytes comprising:
    (a) contacting a population of pluripotent stem cells with a serum-free first mesoderm differentiation medium comprising activin A and an inhibitor of glycogen synthase kinase 3 (GSK-3) or an activator of Wnt signaling pathway;
    (b) contacting a population of cells from step (a) with a serum-free second mesoderm differentiation medium comprising BMP and an inhibitor of glycogen synthase kinase 3 (GSK-3) or an activator of Wnt signaling pathway; and
    (c) contacting a population of cells from step (b) with a podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free,
    thereby producing a population of cells that comprises an increased percentage of podocytes, as compared to a population of cells from step (b) which are not contacted with the podocyte induction medium.
13. A method of generating a population of podocytes comprising:
    (a) differentiating a population of pluripotent stem cells to mesodermal cells and/or intermediate mesodermal cells; and
    (b) culturing the mesodermal cells and/or intermediate mesodermal cells in the presence of a podocyte induction medium for a sufficient amount of time to produce podocytes, the podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free.
14. The method of any of paragraphs 1-13, further comprising exposing the cells to a mechanical strain and/or shear stress.
15. The method of any of paragraphs 1-14, wherein the cells are co-cultured with endothelial cells (e.g., glomerular endothelial cells).
16. The method of paragraph 15, wherein the cells and the endothelial cells are co-cultured in individual chambers separated by a porous or permeable membrane.
17. The method of paragraph 16, wherein application of mechanical strain to the cells enhances extension of podocyte foot processes through the membrane.

18. The method of any of paragraphs 1-17, wherein the GSK-3 inhibitor is CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), GSK-3 inhibitor VI, GSK-3 inhibitor VII, GSK-3 inhibitor X, GSK-3 inhibitor IX, GSK-3 inhibitor XII (TWS119), GSK-3 inhibitor XV, GSK-3 inhibitor XVI, lithium chloride, valproic acid, SB216763, SB415286, Indirubin, Kenpaullone, Hymenidin, or any combinations thereof.
19. The method of any of paragraphs 1-18, wherein the activator of Wnt signaling pathway is Wnt3a, FGF18, beta-catenin, norrin, R-spondin2, or any combinations thereof.
20. The method of any of paragraphs 1-19, wherein the BMP is BMP-2, BMP-4, BMP-7, or any combinations thereof.
21. The method of any of paragraphs 1-20, wherein the concentration of the activin A ranges from about 50 ng/mL to about 500 ng/mL.
22. The method of any of paragraphs 1-21, wherein the concentration of the BMP ranges from about 50 ng/mL to about 500 ng/mL.
23. The method of any of paragraphs 1-22, wherein the concentration of the inhibitor of GSK-3 or the activator of Wnt signaling pathway ranges from about 0.1 µM to about 10 µM.
24. The method of any of paragraphs 1-23, wherein the concentration of the VEGF ranges from about 25 ng/mL to about 250 ng/mL.
25. The method of any of paragraphs 1-24, wherein the concentration of the retinoic acid ranges from about 0.01 µM to about 1 µM.
26. The method of any of paragraphs 1-25, wherein at least one of the components (i)-(v) in the podocyte induction medium is immobilized on a biomaterial substrate.
27. The method of any of paragraphs 1-26, wherein the cells are cultured as adherent cells during the contacting step.
28. The method of paragraph 27, wherein the cells are cultured on a surface coated with at least one extracellular matrix protein.
29. The method of paragraph 28, wherein the extracellular matrix is selected from the group consisting of laminin, collagen, fibronectin, vitronectin, hyaluronic acid, peptides, gelatin, matrigel, decellularized matrix, and combinations thereof.
30. The method of paragraph 29, wherein the cells are cultured on a surface coated with laminin and/or collagen.
31. The method of paragraph 30, wherein the cells are cultured on a surface coated with decellularized matrix produced by glomerular endothelial cells, podocytes and/or a tissue.
32. The method of any of paragraphs 1-31, wherein the cells are cultured in suspension or embedded in a biomaterial scaffold during the contacting step.
33. The method of any of paragraphs 1-32, wherein the cells are human cells.
34. The method of any of paragraphs 1-33, further comprising selecting or obtaining the podocytes upon the contacting step with the podocyte induction medium.
35. The method of paragraph 34, wherein the podocytes are selected by at least one or more of the following criteria:
    a. the podocytes are substantially negative for a pluripotency marker;
    b. the podocytes are positive (e.g., above a threshold level) for at least one or more podocyte marker;
    c. the podocytes have low or substantially no expression of progenitor cell marker; and
    d. the podocytes are substantially incapable of proliferation.
36. The method of paragraph 34 or 35, wherein the selecting is performed by flow cytometry and/or immunostaining.
37. The method of any of paragraphs 1-36, wherein the podocytes are post-mitotic podocytes.
38. An isolated population of podocytes produced by the methods of any of paragraphs 1-37, and optionally in combination with a cell culture medium appropriate for podocyte culture.
39. The isolated population of podocytes of paragraph 38, wherein the cell culture medium is a podocyte induction medium.
40. An isolated population of podocytes produced by the methods of any of paragraphs 1-37 in the presence of a freezing medium or a cryogenic storage medium.
41. The isolated population of podocytes of paragraph 40, wherein the freezing medium or a cryogenic storage medium is a cell culture medium comprising serum protein and/or cryoprotectant, e.g., dimethyl sulfoxide (DMSO).
42. The isolated population of podocytes of any of paragraphs 38-41, wherein the podocytes are genetically modified.
43. The isolated population of podocytes of any of paragraphs 38-42, wherein the podocytes are post-mitotic podocytes.
44. The isolated population of podocytes of any of paragraphs 38-43, wherein the podocytes have a cell size ranging from about 30 µm to about 90 µm, when the podocytes are dissociated or non-adherent in a culture suspension.
45. The isolated population of podocytes of any of paragraphs 38-44, wherein the podocytes exhibit an increased uptake of exogenous albumin, as compared to mature podocytes naturally occurring in vivo or immortalized podocytes.
46. A synthetic tissue scaffold comprising a biopolymer and an isolated population of podocytes of any of paragraphs 38-45 distributed therein.
47. The synthetic tissue scaffold of paragraph 46, further comprising kidney-associated cells distributed in the biopolymer.
48. The synthetic tissue scaffold of paragraph 46 or 47, wherein the kidney-associated cells are selected from the group consisting of endothelial cells, mesangial cells, epithelial cells, smooth muscle cells or myocytes, granular cells (Juxtaglomerular cells), parietal cells, proximal tubular cells, loop of Henle thin segment cells, duct cells, connective tissue fibroblasts, pericytes, insulin-producing cells, and a combination of two or more thereof.
49. A method of modeling a kidney-specific condition in vitro comprising culturing an isolated population of podocytes of any of paragraphs 38-45 in a cell culture device.
50. The method of paragraph 49, wherein the podocytes were differentiated from pluripotent stem cells in the cell culture device prior to the culturing.

51. The method of paragraph 50, wherein the pluripotent stem cells are derived from normal, healthy cells or diseased cells.

52. The method of paragraph 51, wherein the diseased cells are derived from a subject carrying a kidney and/or glomerular disorder.

53. The method of any of paragraphs 49-52, further comprising contacting the podocytes with an agent that induces the podocytes to acquire at least one phenotypic characteristic associated with a kidney and/or glomerular disorder, thereby modeling a kidney and/or glomerular disorder in vitro.

54. The method of any of paragraphs 49-53, wherein the cell culture device is a transwell, a microwell, a microfluidic device, a reactor, or any combinations thereof.

55. The method of paragraph 54, wherein the microfluidic device is an organ-on-a-chip device.

56. The method of paragraph 55, wherein the organ-on-a-chip device comprises a first channel and a second channel separated by a membrane.

57. The method of paragraph 56, wherein a first surface of the membrane facing the first channel comprises the podocytes adhered thereon.

58. The method of paragraph 56 or 57, wherein a second surface of the membrane facing the second channel comprises kidney capillary endothelial cells or glomerular endothelial cells adhered thereon.

59. A method of screening for an agent to reduce at least one phenotypic characteristic of podocytes associated with a kidney and/or glomerular disorder comprising:
   a. culturing an isolated population of podocytes of any of paragraphs 38-45 that display at least one phenotypic characteristic associated with the kidney and/or glomerular disorder;
   b. contacting the podocytes with a library of candidate agents; and
   c. detecting response of the podocytes to the candidate agents to identify an agent based on detection of the presence of a reduction in the phenotypic characteristic of the podocytes associated with the kidney and/or glomerular disorder.

60. A method of treating a kidney and/or glomerular disorder comprising transplanting an isolated population of podocytes of any of paragraphs 38-45 and/or the synthetic tissue scaffold of any of paragraphs 46-48 to a subject in need thereof.

61. The method of paragraph 60, wherein the podocytes and/or the synthetic tissue scaffold are transplanted to a portion of a kidney of the subject.

62. The method of paragraph 60 or 61, wherein the subject in need thereof is determined to have a kidney and/or glomerular disorder.

63. The method of paragraph 62, wherein the kidney and/or glomerular disorder is characterized by podocyte injury, proteinuria, glomerulosclerosis, diabetic nephropathy, or combinations thereof.

64. The method of any of paragraphs 60-63, wherein the pluripotent stem cells are derived from at least one somatic cell of the subject.

65. The method of any of paragraphs 60-63, wherein the pluripotent stem cells are allogeneic cells.

66. The method of any of paragraphs 60-65, wherein the transplanted podocytes migrate and localize into at least one glomerular capillary structure of the kidney tissue.

67. A kit (e.g., for generating a population of podocytes) comprising:
   a. a first container comprising activin A and an inhibitor of glycogen synthase kinase 3 (GSK-3) or an activator of Wnt signaling pathway;
   b. a second container comprising bone morphogenetic protein (BMP) and an inhibitor of glycogen synthase kinase 3 (GSK-3) or an activator of Wnt signaling pathway; and
   c. a third container comprising (i) activin A, (ii) BMP, (iii) an inhibitor of GSK-3 or an activator of Wnt signaling pathway, (iv) vascular endothelial growth factor (VEGF), and (v) retinoic acid, and
   wherein the first container, the second container and the third container are each serum-free.

68. The kit of paragraph 67, wherein the components in the first, second or third container are in a form of powder.

69. The kit of paragraph 67, wherein the components in the first, second or third container are in a form of liquid.

70. The kit of any of paragraphs 67-69, further comprising a microfluidic device.

71. The kit of paragraph 70, wherein the microfluidic device is an organ-on-a-chip device.

72. The kit of paragraph 71, wherein the organ-on-a-chip device comprises a first channel and a second channel separated by a membrane.

73. The kit of paragraph 72, wherein a first surface of the membrane facing the first channel comprises the podocytes adhered thereon.

74. The kit of paragraph 72 or 73, wherein a second surface of the membrane facing the second channel comprises kidney capillary endothelial cells or glomerular endothelial cells adhered thereon.

75. The kit of any of paragraphs 67-74, further comprising a vial of undifferentiated pluripotent stem cells.

76. The kit of any of paragraphs 67-75, further comprising a vial of immortalized podocytes.

77. The kit of any of paragraphs 67-76, further comprising one or more containers each containing a detectable label or affinity tag that specifically binds to a pluripotency marker, a podocyte-specific marker, or a progenitor cell marker.

78. A podocyte induction medium comprising (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid, wherein the podocyte induction medium is serum-free.

79. The podocyte induction medium of paragraph 78, wherein the concentration of the activin A ranges from about 50 ng/mL to about 500 ng/mL.

80. The podocyte induction medium of paragraph 78 or 79, wherein the concentration of the BMP ranges from about 50 ng/mL to about 500 ng/mL.

81. The podocyte induction medium of any of paragraphs 78-80, wherein the concentration of the inhibitor of GSK-3 or the activator of Wnt signaling pathway ranges from about 0.1 μM to about 10 μM.

82. The podocyte induction medium of any of paragraphs 78-81, wherein the concentration of the VEGF ranges from about 25 ng/mL to about 250 ng/mL.

83. The podocyte induction medium of any of paragraphs 78-82, wherein the concentration of the retinoic acid ranges from about 0.01 μM to about 1 μM.

84. The podocyte induction medium of any of paragraphs 78-83, further comprising a population of podocytes.

85. The podocyte induction medium of paragraph 84, wherein the podocytes are generated by a method of any of paragraphs 1-37.

Some Selected Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±5%. When "0%" is used to describe the amount of a component, it is understood that this includes situations where only trace amounts of the component are present.

As used in this specification and the appended claims, the singular forms "a," "an," and "the" include singular and plural references unless the context clearly dictates otherwise. Thus for example, references to "the method" includes one or more methods, and/or steps of the type described herein and/or which will become apparent to those persons skilled in the art upon reading this disclosure and so forth. For example, the term "a GSK-3 inhibitor" includes reference to one or a plurality (e.g., two or more) of GSK-3 inhibitor(s) and the term "the GSK-3 inhibitor" includes reference to one or a plurality (e.g., two or more) of GSK-3 inhibitor(s) and equivalents thereof known to those skilled in the art, and so forth, it is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "a population of" when used in reference to pluripotent stem cells, mesodermal cells, intermediate mesodermal cells or podocytes, refers to cells of interest (e.g., pluripotent stem cells, mesodermal cells, intermediate mesodermal cells, or podocytes) that make up at least about 70%, at least about 80%, at least about 90%, or at least about 95% or more (up to 100%) of the total cell population. In some embodiments, the term "a population of" refers to the entire population (i.e., 100%) being the cells of interest (e.g., pluripotent stem cells, mesodermal cells, intermediate mesodermal cells, or podocytes).

The term "reprogramming" as used herein refers to a process that alters or reverses the differentiation state of a differentiated cell (e.g. a somatic cell). Reprogramming refers to a process of driving the differentiation of a cell backwards to a more undifferentiated or more primitive type of cell, and includes reprogramming a somatic cell to produce an induced pluripotent stem cell and/or reprogramming a somatic cell using somatic cell nuclear transfer (SCNT)-based methods to produce nuclear transfer embryonic stem cells (NT-ESCs) and/or human nuclear transfer embryonic stem cells (hNT-ESCs).

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "differentiated cell" is meant any cell (e.g., a primary cell) that is not, in its native form, pluripotent as that term is defined herein. The transition of a differentiated cell to pluripotency requires a reprogramming stimulus beyond the stimuli that lead to partial loss of differentiated character in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process such differentiated cell may be multipotent.

As used herein, the term "adult cell" refers to a cell found throughout the body after embryonic development.

In the context of cell ontogeny, the term "differentiate", or "differentiating" is a relative term meaning a "differentiated cell" is a cell that has progressed further down the developmental pathway than its precursor cell. Thus in some embodiments, a reprogrammed cell as this term is defined herein, can differentiate to lineage-restricted precursor cells (such as a ectodermal stem cell), which in turn can differentiate into other types of precursor cells further down the pathway (such as an tissue specific precursor or progenitor cell, for example, a podocyte precursor or progenitor cell), and then to an end-stage differentiated cell, which plays a characteristic role in a certain tissue type, e.g., podocyte, and may or may not retain the capacity to proliferate further.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "isolated" as used herein refers, in the case of a cell or a population of cells, to a cell or a population of cells that has or have been removed from an organism in which it was originally found or a descendant of such a cell. Optionally the cell(s) have been cultured in vitro, e.g., in the presence of other kidney-specific cells. Optionally the cell(s) are later introduced into a second organism or re-introduced into the organism from which they (or the cell(s) from which they are descended) were isolated.

The term "isolated population" with respect to an isolated population of cells as used herein refers to a population of cells that has been removed and separated from a mixed or heterogeneous population of cells. In some embodiments, an isolated population is a substantially pure population of cells.

The term "substantially pure", with respect to a particular cell population, refers to a population of cells that is at least about 75%, at least about 80%, at least about 85%, at least about 90%, or at least about 95% pure, with respect to the cells making up a total cell population. With regard to a population of differentiated podocytes, the term "substantially pure" refers to a population of cells that contain fewer than about 30%, of pluripotent stem cells, mesodermal cells, and/or intermediate mesodermal cells. In some embodiments, the population of cells can contain fewer than about 25%, or 20%, or 15%, or 10%, or 8%, or 7%, or 5%, or 1% of pluripotent stem cells, mesodermal cells, and/or intermediate mesodermal cells. Stated another way, the term "substantially pure" refers to a population of cells that contain at least about 70% of podocytes. In some embodiments, the population of cells contain at least about 80%, at least about 90%, at least about 95%, at least about 97%, at least about 99%, or up to 100% of podocytes.

The terms "enriching" or "enriched" are used interchangeably herein and mean that the yield (fraction) of cells of one type is increased by at least 10% over the fraction of cells of that type in the starting culture or preparation.

As used herein, the term "medium" or "media" are used interchangeably herein, and when used in reference to podocyte induction media (PIM), a first mesoderm differentiation medium and/or a second mesoderm differentiation medium, refers to a basal medium or media for culturing cells containing nutrients that maintain cell viability and support proliferation. The cell culture basal medium can contain any of the following in an appropriate combination: salt(s), buffer(s), amino acids, glucose or other sugar(s), antibiotics, and other components such as peptide growth factors, etc. Cell culture media ordinarily used for particular cell types are known to those skilled in the art. Examples of cell culture medium include Minimum Essential Medium (MEM), Eagle's Medium, Dulbecco's Modified Eagle Medium (DMEM), Dulbecco's Modified Eagle Medium: Nutrient Mixture F-12 (DMEM F12), F-10 Nutrient Mixture, Ham's F-10 Nutrient Mix, Ham's F12 Nutrient Mixture, Medium 199, RPMI, RPMI 1640, reduced serum medium, basal medium (BME), DMEM/F12 (1:1), and the like, and combinations thereof. The cell culture basal medium or media can be modified by adding one or more factors or components to suit the need of different applications. For example, to make the podocyte induction media (PIM) described herein, the cell culture basal medium or media can further comprise, or essentially consist of, or consist of (i) activin A, (ii) bone morphogenetic protein (BMP), (iii) an inhibitor of glycogen synthase kinase 3 (GSK-3) or an activator of Wnt signaling pathway, (iv) vascular endothelial growth factor (VEGF), and (v) retinoic acid. To make the first mesoderm differentiation media described herein, the cell culture basal medium or media can further comprise, or essentially consist of, or consist of activin A, and an inhibitor of glycogen synthase kinase 3 (GSK-3) or an activator of Wnt signaling pathway. To make the second mesoderm differentiation media described herein, the cell culture basal medium or media can further comprise, or essentially consist of, or consist of BMP and an inhibitor of glycogen synthase kinase 3 (GSK-3) or an activator of Wnt signaling pathway.

The term "serum-free" as used herein refers to a cell culture medium which does not contain serum.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% as compared to a reference level.

The terms "increased","increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. In some embodiments, such markers are proteins, and possess an epitope for antibodies or other binding molecules available in the art, and thus can be monitored by FACs analysis, and immunocytochemistry. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to filtrate particles, ability to migrate under particular conditions, and the ability to differentiate along particular lineages. Markers may be detected by any method available to one of skill in the art, including for example, detection of nucleic acid, e.g. mRNA, e.g. by quantitative PCR.

A "variant" polypeptide means a biologically active polypeptide having at least 70%, 75%, 80%, 85%, 90%, 95%, 98%, or 99% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues: and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, at least about 95%, or at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural polypeptide.

A "variant" of a small molecule, e.g., a GSK-3 inhibitor or an activator of Wnt signaling pathway, means a derivative of a parent molecule, e.g., a molecule having at least 70%, 75%, 80%, 85%, 90%, 95%, 98%, or 99% molecular structure identity with the parent molecule, and retaining at least 70%, 75%, 80%, 85%, 90%, 95%, 98%, or 99% function of the parent molecule.

As used herein, the term "subject" refers to any living organism which can be administered to the pharmaceutical compositions of the present invention and in which cancer or a proliferative disorder can occur. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. As used herein, the terms "subject" and "individual" are used interchangeably and are intended to refer to an animal, for example a human, to whom treatment, including prophylactic treatment, with the pharmaceutical composition according to the present invention, is provided, including, but not limited to humans and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

All patents, patent applications, and publications identified in this document are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The following examples are not intended to limit the scope of the invention, but are rather intended to be exemplary of certain embodiments.

Example 1

Figure 1A:
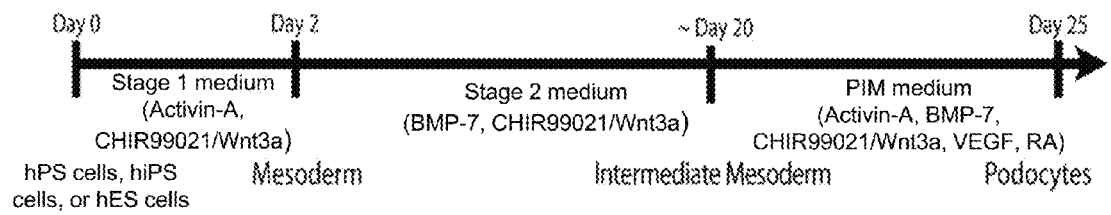
FIGS. 1A-1C show directed differentiation of hPS cells into podocytes according to one embodiment of the methods described herein.
Figure 1B:
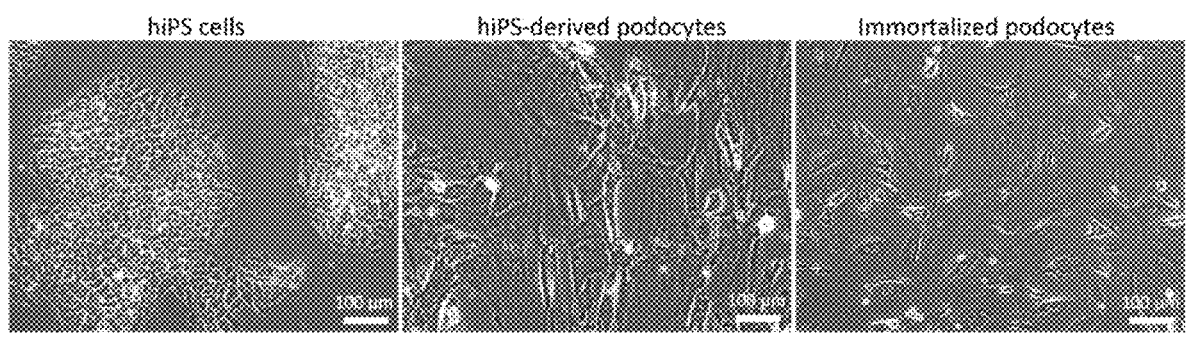

Exemplary Methods for Efficient Derivation of Podocytes from Human Pluripotent Stem Cells Presented in this Example is a highly efficient method for differentiation of human pluripotent stem (hPS) cells into podocytes. The method involved three sequential steps (FIG. 1A). First, hPS cells were induced to differentiate into mesoderm by treatment with a serum-free first mesoderm differentiation medium comprising Activin-A and a small molecule inhibitor of glycogen synthase kinase 3β (e.g., CHIR99021) or an activator of Wnt signaling. An example composition of the serum-free first mesoderm differentiation medium is listed in Table 1 below.

TABLE 1

Composition of the mesoderm induction or differentiation medium according to one embodiment described herein
Mesoderm induction or differentiation medium

| Component | Final concentration |
|---|---|
| Activin A | 100 ng/mL |
| CHIR99021 | 3 μM |
| Y27632 | 10 μM |
| B27 supplement | 1X |
| DMEM/F12 + GlutaMax (1X) | ~96.7% (v/v) |
| DMEM/F12 (Ham) (1:1) | |
| 2.438 g/L Sodium Bicarbonate | |
| Sodium Pyruvate | |
| Penicillin-Streptomycin (10,000 U/mL) | 1% (v/v) |

The mesoderm cells were then differentiated into intermediate mesoderm by treatment with a serum-free second mesoderm differentiation medium comprising bone morphogenetic protein 7 (BMP-7) and a small molecule inhibitor of glycogen synthase kinase 3β (e.g., CHIR99021) or an activator of Wnt signaling. An example composition of the serum-free second mesoderm differentiation medium is listed in Table 2 below.

TABLE 2

Composition of the intermediate mesoderm induction or differentiation medium according to one embodiment described herein
Intermediate mesoderm induction or differentiation medium

| Component | Final concentration |
|---|---|
| BMP-7 | 100 ng/mL |
| CHIR99021 | 3 μM |
| B27 supplement (e.g., from Life Technologies) | 1X |
| DMEM/F12 + GlutaMax (1X) | ~96.9% (v/v) |
| DMEM/F12 (Ham) (1:1) | |
| 2.438 g/L Sodium Bicarbonate | |
| Sodium Pyruvate | |
| Penicillin-Streptomycin (10,000 U/mL) | 1% (v/v) |

In some embodiments, the media used to induce mesoderm and intermediate mesoderm differentiation were based on the protocol described in Mae et al. (2013) *Monitoring and Robust Induction of Nephrogenic Intermediate Mesoderm From Human Pluripotent Stem Cells*. Nat. Commun. 4.

The intermediate mesoderm cells were then treated with a novel podocyte induction medium that efficiently induces formation of differentiated human podocytes. In one embodiment, the podocyte induction medium comprises Activin-A, BMP-7, a small molecule inhibitor of glycogen synthase kinase 3β (e.g., CHIR99021) or an activator of Wnt signaling, VEGF (vascular endothelial growth factor) and RA (retinoic acid). An example composition of the podocyte induction medium is listed in Table 3 below.

TABLE 3

Composition of the podocyte induction medium according to one embodiment described herein.
Podocyte induction medium

| Component | Final concentration |
|---|---|
| VEGF | 50 ng/mL |
| Activin A | 100 ng/mL |
| BMP-7 | 100 ng/mL |
| CHIR99021 | 3 μM |
| Retinoic acid | 0.1 μM |
| B27 supplement | 1X |
| Penicillin-Streptomycin (10,000 U/mL) | 1% (v/v) |
| DMEM/F12 + GlutaMax (1X) | ~96.5% (v/v) |
| DMEM/F12 (Ham) (1:1) | |
| 2.438 g/L Sodium Bicarbonate | |
| Sodium Pyruvate | |

The B27 supplement used in the composition of media listed in Tables 1-3 is a composition comprising, essentially consisting of, or consisting of biotin, DL Alpha Tocopherol acetate, DL Alpha-Tocopherol, Vitamin A (acetate), BSA fatty acid free Fraction V, catalase, human recombinant insulin, human transferrin, superoxide dismutase, corticosterone, D-galactose, ethanolamine HCl, glutathione (reduced), L-carnitine HCl, linoleic acid, linolenic acid, progesterone, putrescine 2HCl, sodium selenite, and T3 (triodo-1-thyronine).

Figure 1C:
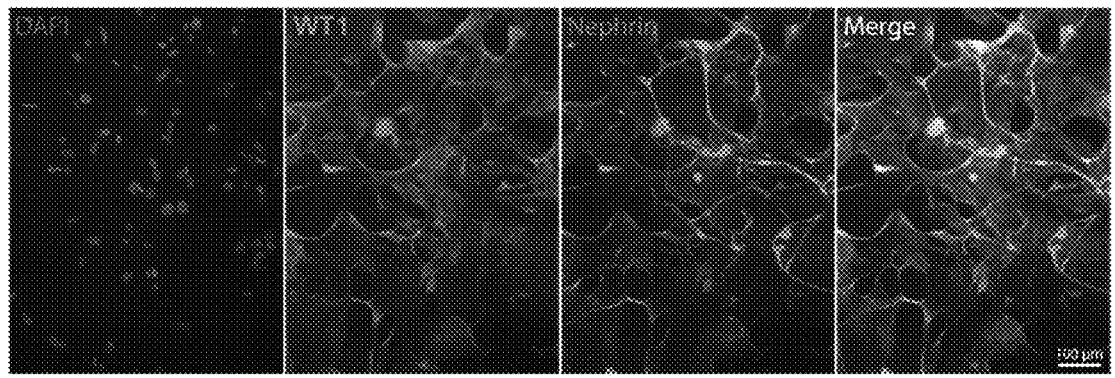
Figure 2A:
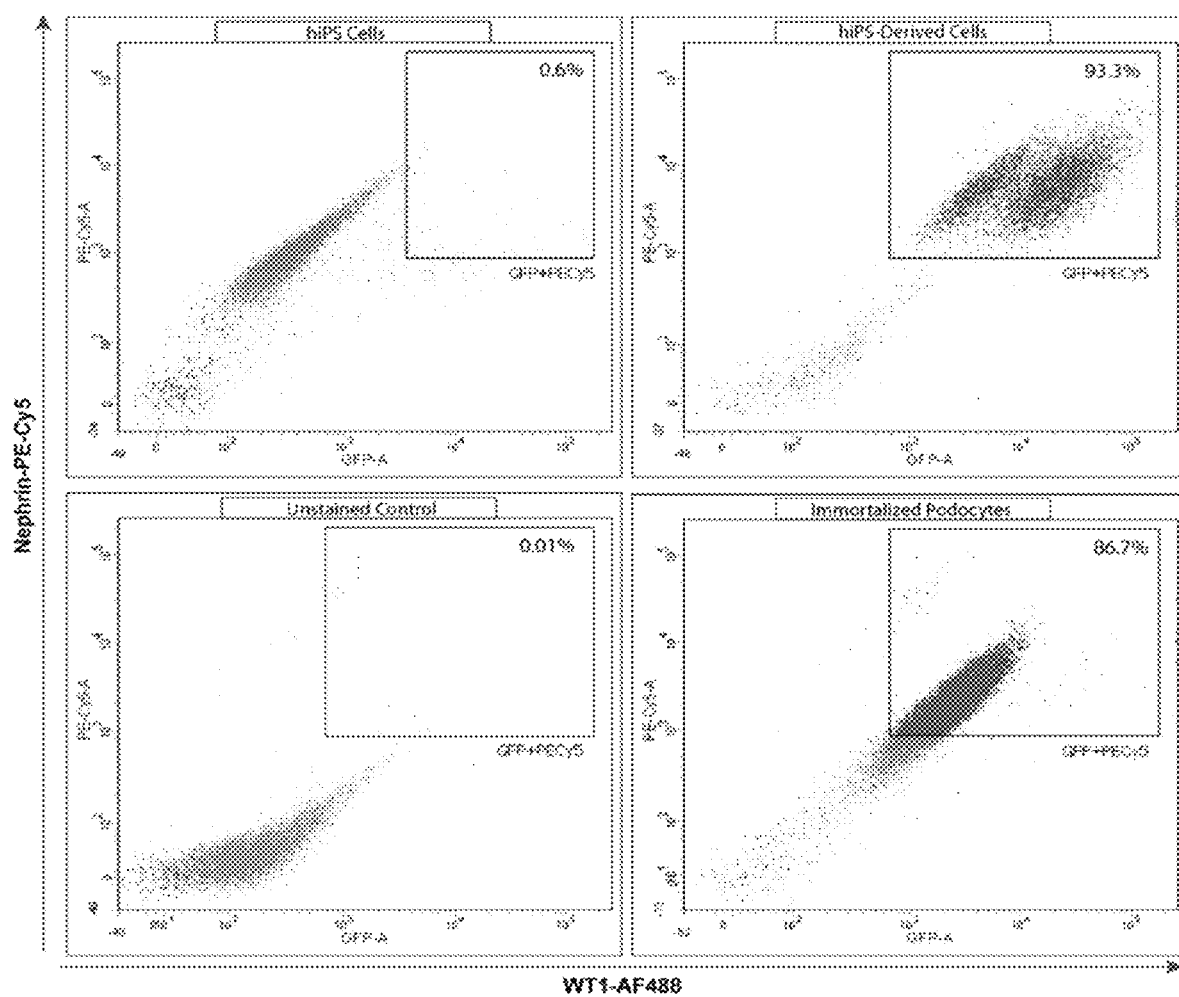
FIGS. 2A-2B show quantification of human iPS-derived podocytes.
Figure 2B:
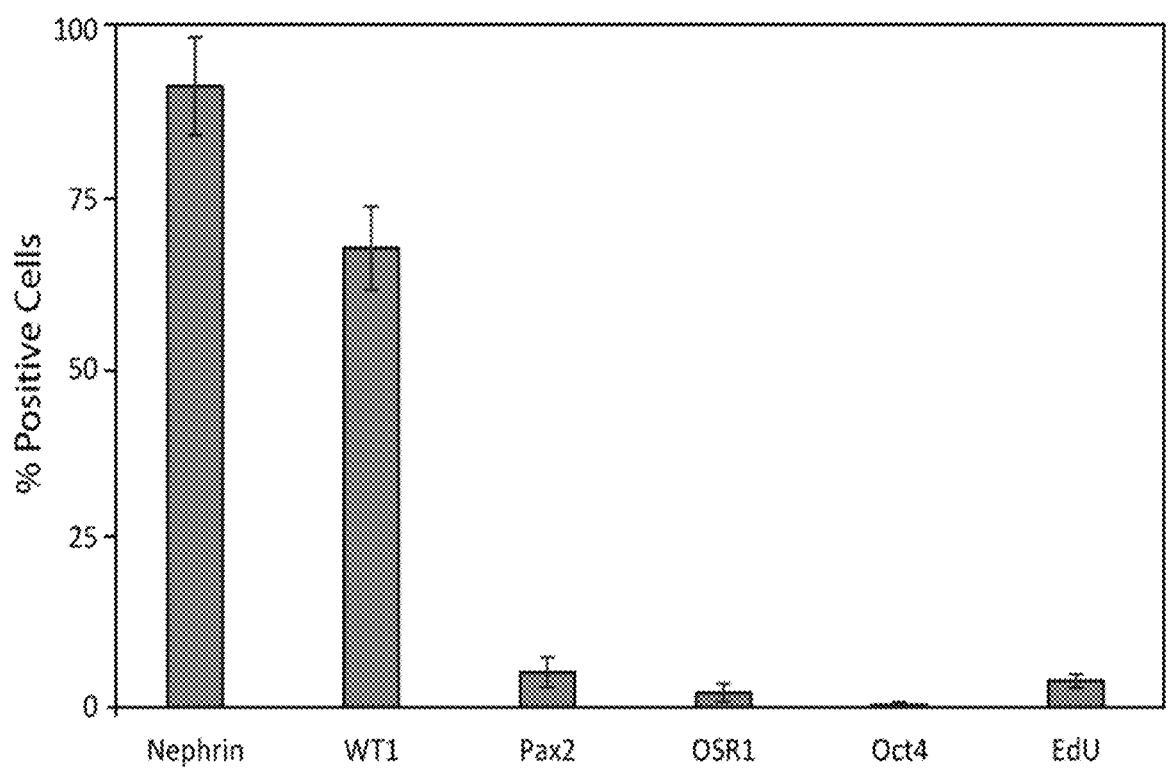

It was discovered that the novel podocyte induction medium functions rapidly (e.g., 3-5 days) and efficiently (e.g., ~93% or higher) induces the differentiation of hPS cell-derived intermediate mesoderm cells into podocytes (FIGS. 1B-1C and FIGS. 2A-2B). FIG. 1C shows that that hPS cell-derived podocytes immunostained for at least one marker of kidney cells, e.g., WT1 (Wilm's tumor protein 1) and at least one podocyte-specific marker (e.g., nephrin). Further, the hPS cell-derived podocytes showed a decrease in Oct4 pluripotency marker. The decrease in progenitor cell markers (e.g., Pax2 and OSR1) and lack of EdU incorporation also indicate that the hPS cell-derived podocytes were post-mitotic and terminally differentiated, as in mature podocytes (FIGS. 2A-2B).

In some embodiments, the podocyte differentiation method does not involve or require formation of embryoid bodies. In some embodiments, all three differentiation steps (FIG. 1A), e.g., as shown in this Example, the cells were immobilized on laminin-coated surfaces.

Example 2

Exemplary Additional Methods for Efficient Derivation of Podocytes from Human Pluripotent Stem Cells In some embodiments, the method for differentiation of human pluripotent stem (hPS) cells into podocytes as described in FIG. 1A can be modified, e.g., the time period for each stage can be optimized. FIG. 3A shows directed differentiation of hPS cells into podocytes according to another embodiment of the methods described herein. In this Example, the media used at different stages of the differentiation process can have the same formulations as described in Tables 1-3 above.

Figure 3B:
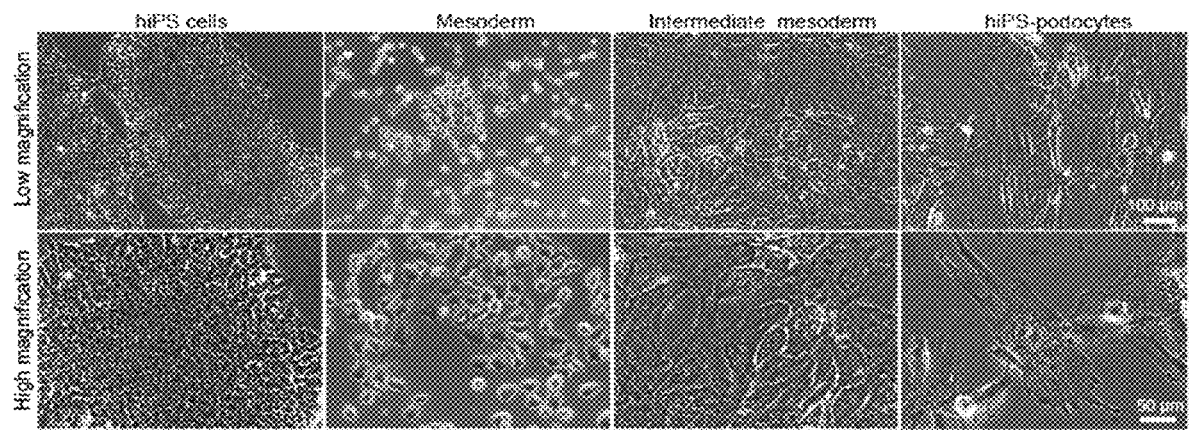

FIG. 3B show morphology of cells at different stages of the differentiation process from human induced pluripotent stem (hiPS) cells to mesoderm cells to intermediate mesoderm cells to podocytes. The hiPS-derived podocytes had comparable size (e.g., within 10% or less) as immortalized podocytes, which were used as positive control. The hiPS-derived podocytes were generally bigger in size than undifferentiated hiPS cells (FIGS. 4A-4B). As shown in FIG. 4B, the hiPS-derived podocytes had a cell size of about 30 µm to about 90 µm, when they were dissociated (e.g., in a suspension) or non-adherent on a surface.

The hiPS-derived podocytes were then characterized by flow cytometry and immunostaining for different cell markers. FIGS. 5A-5B show flow cytometry analyses for the expression of pluripotency and podocyte markers in human iPS cells, human iPS-derived podocytes, and immortalized human podocytes. Immortalized human podocytes were used as positive control for podocyte markers. The hiPS-derived podocytes show decreased or no expression of a pluripotency marker (e.g., Oct4) but increased expression of both kidney-specific marker (e.g., Wilm's tumor protein 1, WT1) and podocyte-specific marker (e.g., nephrin), as compared to undifferentiated pluripotent stem cells. In addition, the expressions of kidney-specific marker(s) and/or podocyte-specific marker(s) in the hiPS-derived podocytes are comparable (e.g., within 10% or less) to those in the immortalized podocytes.

FIG. 6A-6B show immunohistochemical analysis of human PS-derived podocytes. Consistent with the flow cytometry analyses as described above, human iPS-derived podocytes exhibited upregulation of podocyte markers (including, e.g., nephrin, WT1, and podocin), with corresponding decrease in pluripotency marker (including, e.g., Oct4). The decrease in progenitor cell markers (including, e.g., Pax2 and OSR1) and lack of EdU incorporation in human iPS-derived podocytes indicate that the cells are post-mitotic and terminally differentiated, as in mature podocytes. In some embodiments, the hiPS-derived podocytes can have lower expression of Pax2 than that in immortalized podocytes or mature podocytes, for example, by at least about 30% or more, including, e.g., at least about 40%, at least about 50%, at least about 60%, at least about 70%, at least about 80%, at least about 90% or more.

In some embodiments, the hiPS-derived podocytes can be selected for high expression levels (e.g., as comparable to the levels observed in mature podocytes) of podocyte-specific markers (e.g., but not limited to, nephrin, WT1, and/or podocin), and low or no expression of a pluripotency marker (including, e.g., Sox2, Oct 4, c-Myc, Klf4, Nanog, and/or Lin28). In some embodiments, the hiPS-derived podocytes can be further selected for low or no expression of progenitor cell markers (including, e.g., Pax2 and/or OSR1).

The hiPS-derived podocytes also expressed podocin in both the cell body and foot processes. They exhibited primary and secondary foot processes as in mature and functional glomerular podocytes in vivo (FIGS. 7A-7B).

To assess the function of the hiPS-derived podocytes, the cells were immunostained for receptors for IgG and/or albumin transport, as well as evaluated in a functional assay to measure uptake of exogenous albumin. FIG. 8A show that human iPS-derived podocytes expressed FcRn (IgG and albumin transport receptor) in the cell nucleus, cytoplasm, and foot processes. Human immortalized podocytes were used as positive control. Cells were counterstained with DAPI (nuclei). When the hiPS-derived podocytes were contacted with a fluid comprising albumin, albumin was taken up by the podocytes, which is a feature of functional glomerular podocytes. It is also noted that the hiPS-derived podocytes displayed enhanced ability to uptake exogenous albumin, as compared to immortalized podocytes (FIG. 8B).

Not only can the hiPS-derived podocytes exhibit functional capabilities as glomerular podocytes in vivo, they can also integrate into a kidney tissue and localize to glomerular capillary structures (FIGS. 9A-9C). The kidney tissue can be part of a developing embryonic kidney, an adult kidney, or a kidney at other developmental stages. In this Example, embryonic mouse kidneys (E16) were microinjected with pre-labeled (Qtracker655-labeled) human iPS-derived podocytes or immortalized human podocytes, and cultured for 3 days. Then, the kidneys were sectioned and counterstained with DAPI (nucleus). FIG. 9A shows that the microinjected hiPS-derived podocytes (visualized by the fluorescent label) integrated into the mouse kidneys. In addition, the microinjected human iPS-derived podocytes migrated and localized into glomerular structures (white arrow heads) more efficiently than immortalized human podocyte cell line (FIGS. 9B-9C). The ability of human PS-derived podocytes to integrate into the kidney and selectively localize to glomerular structures indicates that the cells can be used for tissue/organ regeneration and/or development of cell-based therapeutics.

Example 3

Differentiation of Human iPS Cells into Podocytes in a Microfluidic Device and Modeling of the Structure and Function of Human Glomerular Capillary Wall The podocyte differentiation processes described herein can be performed in any suitable cell culture device, including, e.g., microwells, transwells, tissue culture plates and/or flasks, microfluidic devices, and any combinations thereof. In some embodiments, the podocyte differentiation processes described herein can be performed in a microfluidic device or in an organ-on-a-chip device. In some embodiments, the organ-on-a-chip device can comprise a first chamber (e.g., a channel), a second chamber (e.g., a channel), and a porous membrane separating the first structure and the second structure. The first chamber and the second chamber can be of substantially equal (e.g., within 10% or within 5% or less) heights or of different heights. FIG. 10B shows an organ-on-a-chip device, in which the first structure (e.g., a channel) and the second structure (e.g., a channel) are of different heights. The height ratio of the first structure to the second structure can range from about 2:1 to about 10:1. In some embodiments, the height ratio of the first structure (where podocytes are cultured) to the second structure (which mimics a capillary with or without endothelial cells cultured therein) can be about 5:1, as used in this Example. Podocytes are generally larger in size than endothelial cells; thus a higher channel for podocyte culture can provide more space for podocytes to develop.

In some embodiments, the organ-on-a-chip device can further comprise at least one operating channel on either one or both sides of the first and second structures. Pneumatic pressures or vacuum can be applied to the operating channel to cause the membrane flex or stretch. An exemplary organ-on-a-chip device as described in the International Pat. App. No. WO 2015/138034, and/or in U.S. Pat. No. 8,647,861, the contents of each of which are incorporated herein by reference, can be used to produce pluripotent stem cell-derived podocytes and/or to simulate the structure and/or function of a glomerular capillary wall in vivo. The glomerular basement membrane is modeled by a porous membrane that is amenable to functionalization with appropriate extracellular matrix (ECM) protein(s).

For example, undifferentiated pluripotent stem cells and/or their derivatives including, e.g., mesoderm or intermediate mesoderm cells can be cultured on one side of a porous membrane of an organ-on-a-chip device (e.g., as shown in FIG. 10B) facing the first structure (e.g., first channel), while the other side of the membrane facing the second structure (e.g., second channel) can optionally have endothelial cells (e.g., glomerular endothelial cells) cultured thereon. The undifferentiated pluripotent stem cells and/or their derivatives including, e.g., mesoderm or intermediate mesoderm cells were contacted with appropriate media at different stages of the differentiation process as depicted in FIG. 3A.

In some embodiments, Stage I (mesoderm differentiation) and/or Stage II (intermediate mesoderm differentiation), for example as depicted in FIG. 3A, can be performed in a non-organ-on-a-chip device (e.g., a microplate), and the cells can then be transferred to an organ-on-a-chip device to undergo podocyte differentiation using the podocyte induction media described herein. For example, undifferentiated human iPS cells can be differentiated to intermediate mesoderm stage in a cell culture device other than an organ-on-a-chip device, and the cells are then seeded into an organ-on-a chip device to induce podocyte differentiation using one or more embodiments of the podocyte induction medium described herein (e.g., the formulation as shown in Table 3).

Figure 10C:
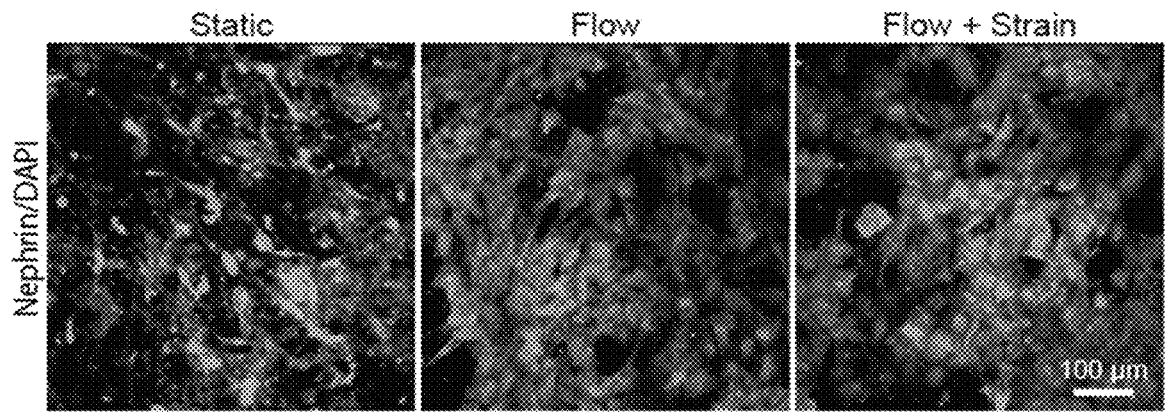
Figure 10D:
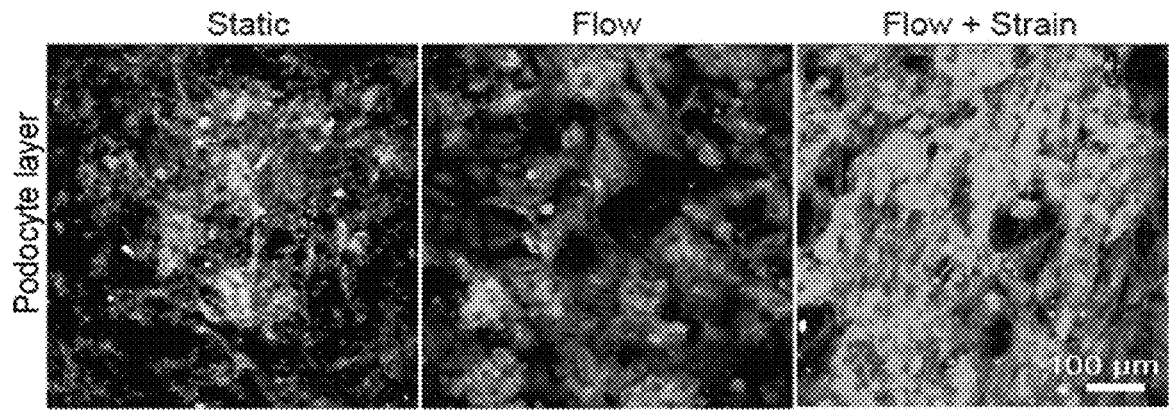

FIGS. 10C-10D show that pluripotent stem cells were able to differentiate into podocytes in the organ-on-a-chip device, with or without endothelial cells on the other side of the membrane, under static flow or fluid flow, alone or in combination with mechanical strain. In some embodiments where a continuous fluid flow was present, the fluid was flowed at a rate of about 60 µL/hr in both the top and bottom channels of the device. This corresponds to a shear stress of about 0.00068 dyne/cm$^2$ for the top (podocyte) channel and a shear stress of about 0.017 dyne/cm$^2$ for the bottom channel that mimics a capillary with or without endothelial cells. The levels of the shear stress can be further tuned to influence cell differentiation and/or function.

Mechanical strain was applied to the cells by actuating or mechanically flexing or stretching the porous membrane, e.g., a porous PDMS membrane. In some embodiments, vacuum was applied to the operating channels of the organ-on-a-chip device (e.g., as shown in FIG. 10B) to periodically stretch the membrane, thereby applying mechanical strain to the cells cultured thereon. In some embodiments, vacuum was applied to the operating channels such that a cyclic strain to the membrane was applied at 1 Hertz and 10% stretch. The frequency and/or degree of the mechanical strain can be differentially tuned to influence cell differentiation and/or function.

In some embodiments, undifferentiated pluripotent stem cells can be differentiated into podocytes in a non-microfluidic device (e.g., a microplate) and then transferred to an organ-on-a-chip device to establish an vitro model of a glomerular tissue-tissue interface.

Figure 10E:
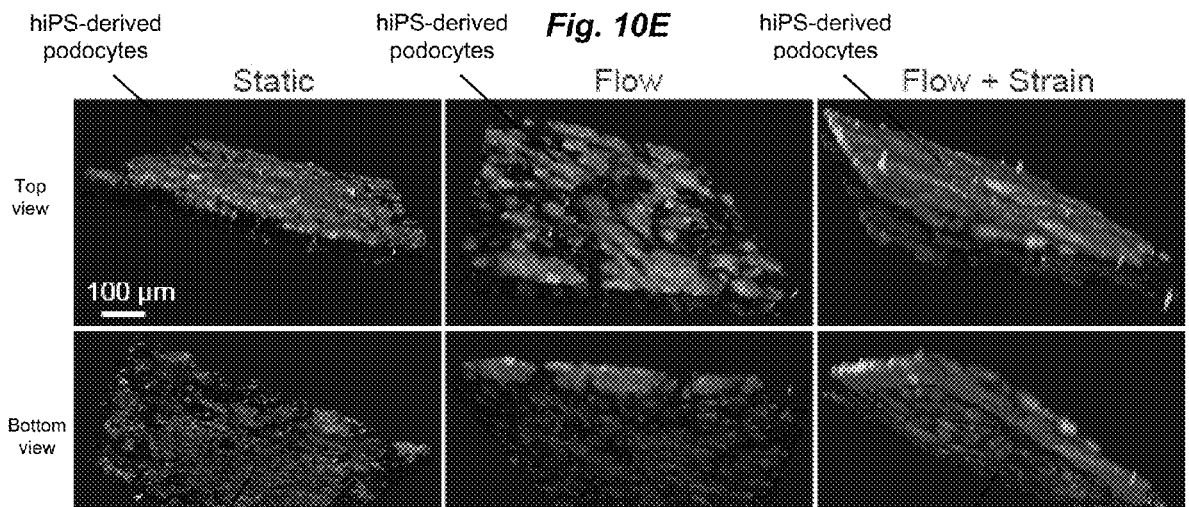
Figure 10F:
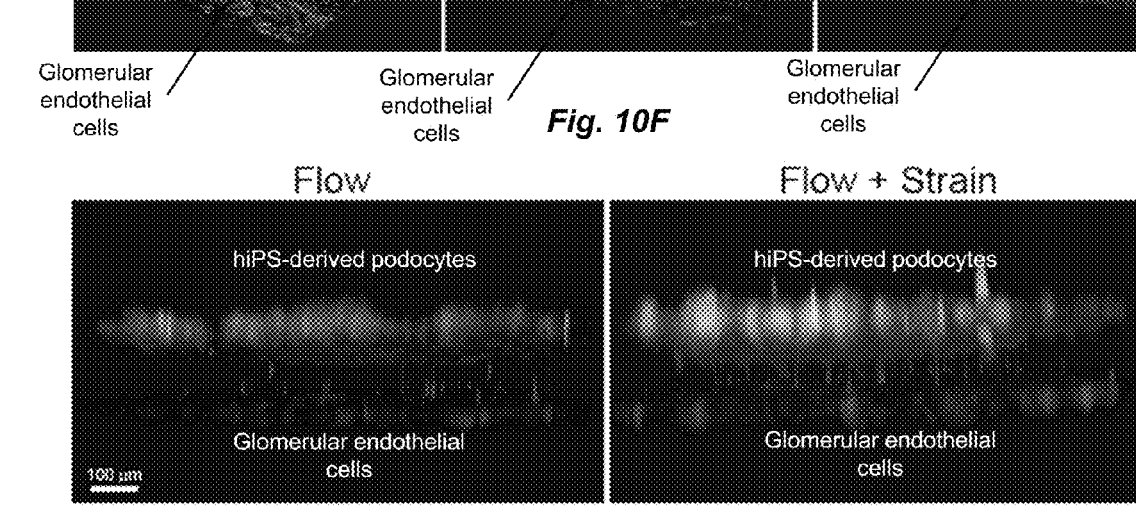

In some embodiments, an in vitro model of glomerular tissue-tissue interface can be established in an organ-on-a-chip device by co-culture of human iPS-derived podocytes on one side of the membrane and human glomerular endothelial cells on the other side of the membrane (FIG. 10E). Upon podocyte differentiation, regular cell culture medium (e.g., one from Cell Systems Product, Catalog No. 4Z0-500-R, or other media that are commonly used for maintaining podocytes) can be used to culture differentiated podocytes.

The cells can be cultured under static flow (i.e., no flow), or fluid flow. In some embodiments, the cells can be cultured under mechanical strain. While mechanical strain is not necessary, application of mechanical strain to hiPS-derived podocytes can enhance extension of podocyte foot processes through the membrane of the organ-on-a-chip device (FIG. 10F). Thus, mechanical force can be applied during or after podocyte differentiation using the methods described herein (e.g., as illustrated in FIG. 3A) to facilitate interactions between podocytes and endothelial cells or any other cell type, thereby modulating tissue development and function.

Figure 10G:
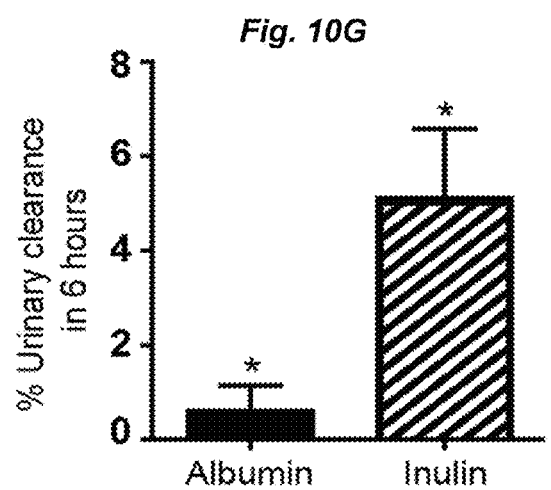

To assess the glomerular filtration function of the in vitro organ-on-a-chip device simulating a glomerular capillary wall, albumin and/or inulin were continuously infused into the second structure (e.g., a channel) of the organ-on-a-chip device, wherein the side of the membrane facing the second structure comprised glomerular endothelial cells cultured thereon, while the other side facing the first structure comprised hiPS-derived podocytes cultured thereon. The second structure comprising glomerular endothelial cells modeled a "capillary" channel, while the first structure comprising hiPS-derived podocytes modeled a "urinary" channel. FIG. 10G shows selective retention of albumin in the "capillary" channel and filtration of inulin into the "urinary" channel, as in functional glomerulus in vivo. Taken together, these data indicate the feasibility of differentiating human PS cells into podocytes in co-culture conditions or environments that mimic tissue-tissue interface. It also shows that the podocyte induction medium can be applied in static or fluidic flow conditions to support podocyte differentiation. The data also shows that mechanical forces can be used in conjunction with the podocyte induction medium to facilitate the differentiation of human PS cells and their derivatives into podocytes.

Example 4

Differentiation of Human iPS Cells into Podocytes on Different ECM Surface

Undifferentiated pluripotent stem cells can be cultured on a surface with or without ECM proteins to perform the podocyte differentiation method as described herein. FIG. 11 shows that iPS cells were differentiated into podocytes when they were cultured with podocyte induction medium as described herein on tissue culture surfaces functionalized with either the extracellular matrix (ECM) protein laminin 511, laminin 511-E8 (a fragment of laminin 511), laminin 521 (also known as laminin 11), or collagen I. A combination of two or more of the above ECM proteins can also facilitate the differentiation of human iPS cells into podocytes when used in combination with the podocyte induction medium. An exemplary surface functionalized with all of the above ECM proteins is shown (combination ECM). It should be noted that tissue culture surfaces lacking functionalization with ECM components or their mimetics can also facilitate differentiation of human PS cells into podocytes, albeit sub-optimal for cell adhesion.

In some embodiments, decellularized ECM proteins can be used to coat a surface on which undifferentiated pluripotent stem cells are cultured. FIG. 12 shows that podocytes were generated by differentiating and culturing human pluripotent stem cells on decellularized matrix, for example, produced by human glomerular endothelial cells. Other sources of decellularized matrix, e.g., produced from podocytes or kidney can also be used. This data indicate the versatility of differentiating and using human PS-derived podocytes for various applications, including, e.g., organ/tissue development, regeneration, and transplantation.

Example 5

Comparison of Conventional Podocyte Culture Medium and the Podocyte Induction Media Described Herein in Podocyte Differentiation Immortalized human podocytes were cultured in regular CSC (Cell Systems Corporation) medium typically used for culturing podocyte cell lines or one embodiment of the podocyte induction medium described herein (e.g., as shown in FIG. 3A: stage 3 human podocyte induction medium, or the formulation as shown in Table 3 above). Cells were immunostained for podocin. The data shows that immortalized human podocytes cultured with the podocyte induction medium described herein decrease proliferation and develop foot processes—both of which indicate enhanced podocyte specialization and maturation. Thus, this data underscores that the podocyte induction method described herein can be used to enhance differentiation and functional maturation of any podocyte cell type including precursor cells that give rise to the same, diseased or healthy cells.

The invention claimed is:

1. A method of generating a population of podocytes comprising: contacting, in a microfluidic device, on a surface coated with at least one extracellular matrix protein, a first population of cells comprising intermediate mesoderm cells with a podocyte induction medium comprising
    (i) activin A,
    (ii) bone morphogenetic protein (BMP),
    (iii) an inhibitor of glycogen synthase kinase 3 (GSK-3) or an activator of Wnt signaling pathway,
    (iv) vascular endothelial growth factor (VEGF), and
    (v) retinoic acid,
    wherein the podocyte induction medium is serum-free,
    wherein said contacting is under conditions that produce a second population of cells wherein said second population of cells comprises an increased percentage of podocytes, compared to a resultant percentage of podocytes produced from a population of intermediate mesoderm cells that are not contacted with the podocyte induction medium, and said second population of cells comprises at least about 90% podocytes; and
    wherein said podocytes are substantially negative for Paired Box 2 (PAX-2), and exhibit an increased uptake of exogenous albumin compared to immortalized podocytes.

2. The method of claim 1, wherein the podocytes are substantially incapable of proliferation in said podocyte induction medium.

3. The method of claim 1, further comprising differentiating a population of pluripotent stem cells to one or more of mesodermal cells and said intermediate mesoderm cells, prior to said contacting said first population of cells comprising said intermediate mesoderm cells with the podocyte induction medium.

4. The method of claim 3, wherein said method comprising contacting, under conditions that produce a population of cells that comprises mesodermal cells, said population of pluripotent stem cells with a serum-free first mesoderm differentiation medium comprising activin A and one or more of an inhibitor of glycogen synthase kinase 3 (GSK-3) and an activator of Wnt signaling pathway.

5. The method of claim 3, wherein said method comprising contacting, under conditions that produce said first population of cells that comprises said intermediate mesoderm cells, one or more said population of pluripotent stem cells and said mesodermal cells with a serum-free second mesoderm differentiation medium comprising BMP and one or more of an inhibitor of glycogen synthase kinase 3 (GSK-3) and an activator of Wnt signaling pathway.

6. The method of claim 1, further comprising exposing said first population of cells or said second population of cells in said microfluidic device to one or more of mechanical strain and shear stress.

7. The method of claim 6, wherein said first population of cells and said second population of cells are positioned on a membrane within said microfluidic device, and wherein application of mechanical strain to the cells comprises stretching said membrane so as to enhance differentiation into podocytes.

8. The method of claim 1, wherein said first population of cells or said second population of cells is cultured with endothelial cells.

9. The method of claim 1, wherein one or more of said GSK-3 inhibitor is selected from the group consisting of: CHIR 99021 (6-[[2-[[4-(2,4-Dichlorophenyl)-S-(5-methyl-IH-imidazol-2-yl)-2-pyrimidinyl]amino] ethyl] amino]-3-pyridinecarbonitrile), GSK-3 inhibitor VI, GSK-3 inhibitor VII, GSK-3 inhibitor X, GSK-3 inhibitor IX, GSK-3 inhibitor XII (TWSI19), GSK-3 inhibitor XV, GSK-3 inhibitor XVI, lithium chloride, valproic acid, SB216763, SB415286, Indirubin, Kenpaullone, Hymenidin, and any combinations thereof; wherein said activator of Wnt signaling pathway is selected from the group consisting of: Wnt3a, FGFI8, beta-catenin, norrin, R-spondin2, and any combinations thereof; and wherein said BMP is selected from the group consisting of: BMP-2, BMP-4, BMP-7, and any combinations thereof.

10. The method of claim 1, wherein
    (i) said activin is at a concentration of about 50 ng/mL to about 500 ng/mL;
    (ii) said BMP is at a concentration of about 50 ng/mL to about 500 ng/mL;
    (iii) said inhibitor of GSK-3 or said activator of Wnt signaling pathway is at a concentration of about 0.1 µM to about 10 µM;
    (iv) said VEGF is at a concentration of about 25 ng/mL to about 250 ng/mL; and
    (v) said retinoic acid is at a concentration of about 0.01 µM to about 1 µM.

11. The method of claim 1, further comprising culturing said podocytes in said microfluidic device.

12. The method of claim 1, wherein said microfluidic device comprises a first channel and a second channel separated by a membrane.

13. The method of claim 12, wherein said podocytes adhere to a first surface of the membrane facing the first channel.

14. The method of claim 13, wherein a second surface of the membrane facing the second channel comprises kidney capillary endothelial cells or glomerular endothelial cells adhered thereon.

15. A method of generating a population of podocytes comprising:
    a) contacting, on a surface coated with at least one extracellular matrix protein, a first population of cells comprising intermediate mesoderm cells with a podocyte induction medium comprising
        (i) activin A,
        (ii) bone morphogenetic protein (BMP),
        (iii) an inhibitor of glycogen synthase kinase 3 (GSK-3) or an activator of Wnt signaling pathway, (iv) vascular endothelial growth factor (VEGF), and
(iv) retinoic acid,
wherein the podocyte induction medium is serum-free, wherein said contacting is under conditions that produce a second population of cells that comprises an increased percentage of podocytes, as compared to a percentage of podocytes comprised in a population of cells comprising intermediate mesoderm cells that are not contacted with the podocyte induction medium, and said second population of cells comprises at least about 90% podocytes, and
wherein said podocytes are substantially negative for Paired Box 2 (PAX-2) protein, and exhibit extension of podocyte foot processes.

16. The method of claim 15, further comprising selecting the podocytes by at least one or more of the following criteria:
a. the podocytes are substantially negative for a pluripotency marker;
b. the podocytes are positive for at least one or more podocyte markers;
c. the podocytes are have low or substantially no expression of a progenitor cell marker.

17. The method of claim 15, wherein said podocytes are substantially incapable of proliferation.

18. The method of claim 17, further comprising culturing said podocytes in a microfluidic device.

19. The method of claim 18, wherein said microfluidic device comprises a first channel and a second channel separated by a membrane.

20. The method of claim 19, wherein said podocytes adhere to a first surface of the membrane facing the first channel.

21. The method of claim 20, wherein a second surface of the membrane facing the second channel comprises kidney capillary endothelial cells or glomerular endothelial cells adhered thereon.

22. The method of claim 15, wherein the extracellular matrix protein is selected from the group consisting of laminin, collagen, fibronectin, vitronectin, hyaluronic acid, peptides, gelatin, matrigel, decellularized matrix, and combinations thereof.

23. A method of generating a population of podocytes, comprising
(a) contacting, a surface coated with at least one extracellular matrix protein, a first population of cells comprising pluripotent stem cells with a serum-free first mesoderm differentiation medium comprising activin A and one or both of an inhibitor of glycogen synthase kinase 3 (GSK-3) and an activator of Wnt signaling pathway, wherein said contacting is under conditions that produce a second population of cells comprising mesodermal cells,
(b) contacting said second population of cells with a serum-free second mesoderm differentiation medium comprising BMP and on e or both of an inhibitor of glycogen synthase kinase 3 (GSK-3) and an activator of Wnt signaling pathway, wherein said contacting is under conditions that produce a third population of cells comprising intermediate mesoderm cells, and
(c) contacting said third population of cells in a microfluidic device with a serum-free podocyte induction medium comprising
(i) activin A,
(ii) bone morphogenetic protein (BMP),
(iii) an inhibitor of glycogen synthase kinase 3 (GSK-3) or an activator of Wnt signaling pathway,
(iv) vascular endothelial growth factor (VEGF), and
(v) retinoic acid,
wherein said contacting is under conditions that produce a fourth population of cells that comprises at least about 90% podocytes that are substantially negative for Paired Box 2 (PAX-2) protein.

24. The method of claim 23, wherein said a fourth population of cells comprises an increased percentage of podocytes as compared to a percentage of podocytes comprised in said third population of cells population of cells that are not contacted with said podocyte induction medium.

25. The method of claim 23, wherein one or both of said contacting step (a) and step (b) are in a microfluidic device.

26. The method of claim 23, wherein said podocytes are substantially incapable of proliferation.

27. The method of claim 2, wherein said podocytes that are substantially incapable of proliferation comprise at least about 80% podocytes that do not undergo cell division.

28. The method of claim 27, wherein said podocytes that are substantially incapable of proliferation comprise at least about 90% podocytes that do not undergo cell division.

29. The method of claim 17, wherein said podocytes that are substantially incapable of proliferation comprise at least about 80% podocytes that do not undergo cell division.

30. The method of claim 29, wherein said podocytes that are substantially incapable of proliferation comprise at least about 90% podocytes that do not undergo cell division.

31. The method of claim 26, wherein said podocytes that are substantially incapable of proliferation comprise at least about 80% podocytes that do not undergo cell division.

32. The method of claim 31, wherein said podocytes that are substantially incapable of proliferation comprise at least about 90% podocytes that do not undergo cell division.

33. The method of claim 2, wherein said podocytes that are substantially incapable of proliferation comprise podocytes that retain the capacity to proliferate.

34. The method of claim 17, wherein said podocytes that are substantially incapable of proliferation comprise podocytes that retain the capacity to proliferate.

35. The method of claim 23, wherein said podocytes that are substantially incapable of proliferation comprise podocytes that retain the capacity to proliferate.

36. A method of generating a population of podocytes comprising contacting, in a microfluidic device, on a surface coated with at least one extracellular matrix protein, a first population of cells comprising intermediate mesoderm cells with a podocyte induction medium comprising
(i) activin A,
(ii) bone morphogenetic protein (BMP),
(iii) an inhibitor of glycogen synthase kinase 3 (GSK-3) or an activator of Wnt signaling pathway,
(iv) vascular endothelial growth factor (VEGF), and
(v) retinoic acid,
wherein the podocyte induction medium is serum-free, wherein said contacting is done under conditions that produce a second population of cells containing at least about 90% podocytes that are substantially negative for Paired Box 2 (PAX-2) protein, and exhibit an increased uptake of exogenous albumin compared to immortalized podocytes.

37. The method of claim 36, wherein said second population of cells contains at least about 95% podocytes.

38. The method of claim 36, wherein said second population of cells contains about 100% podocytes.

39. A method for enhancing differentiation of intermediate mesoderm cells into podocytes, comprising contacting, on a surface coated with at least one extracellular matrix protein, a first population of cells comprising intermediate mesoderm cells with a serum-free podocyte induction medium comprising
- (i) activin A,
- (ii) bone morphogenetic protein (BMP),
- (iii) an inhibitor of glycogen synthase kinase 3 (GSK-3) or an activator of Wnt signaling pathway,
- (iv) vascular endothelial growth factor (VEGF), and
- (v) retinoic acid, wherein said contacting comprises applying mechanical strain to said first population of cells, thereby producing a second population of cells containing at least about 90% podocytes that are substantially negative for Paired Box 2 (PAX-2), exhibit an increased uptake of exogenous albumin compared to immortalized podocytes, and exhibit extension of podocyte foot processes, and enhancing differentiation of said intermediate mesoderm cells into said podocytes compared to differentiation of said intermediate mesoderm cells in the absence of said a serum-free podocyte induction medium and in the absence of said mechanical strain.

40. The method of claim 39, wherein said enhancing differentiation of intermediate mesoderm cells into podocytes comprises enhancing extension of podocyte foot processes.

41. The method of claim 39, wherein said enhancing differentiation comprises increasing the percentage of said podocytes in said second population of cells.

42. The method of claim 39, wherein said enhancing differentiation comprises increasing the percentage of podocytes that are substantially negative for PAX-2 in said second population of cells.

43. The method of claim 39, wherein said enhancing differentiation comprises increasing the percentage of podocytes that are substantially incapable of proliferation.

44. The method of claim 43, wherein said podocytes that are substantially incapable of proliferation comprise podocytes that do not undergo cell division.

45. The method of claim 43, wherein said podocytes that are substantially incapable of proliferation comprise podocytes that retain the capacity to proliferate.

46. The method of claim 39, wherein said first population of cells and said second population of cells are positioned on a membrane, and wherein application of said mechanical strain comprises stretching said membrane.

47. A method for enhancing differentiation of intermediate mesoderm cells into podocytes, comprising applying mechanical strain to a membrane that contains a first population of cells comprising intermediate mesoderm cells adhered to a first surface of said membrane, and a second population comprising endothelial cells adhered to a second surface of said membrane, wherein application of said mechanical strain is under conditions for enhancing differentiation of said intermediate mesoderm cells into said podocytes compared to differentiation of said intermediate mesoderm cells in the absence of said mechanical strains and in the absence of said endothelial cells, and said application of said mechanical strain produces a third population of cells containing at least about 90% podocytes that are substantially negative for Paired Box 2 (PAX-2), and exhibit extension of podocyte foot processes.

48. The method of claim 47, wherein said enhancing differentiation of intermediate mesoderm cells into podocytes comprises enhancing extension of podocyte foot processes.

49. The method of claim 47, wherein said enhancing differentiation comprises increasing the percentage of said podocytes in said second population of cells.

50. The method of claim 47, wherein said enhancing differentiation comprises increasing the percentage of podocytes that are substantially negative for PAX-2 in said second population of cells.

51. The method of claim 47, wherein said enhancing differentiation comprises increasing the percentage of podocytes that are substantially incapable of proliferation.

52. The method of claim 51, wherein said podocytes that are substantially incapable of proliferation comprise podocytes that do not undergo cell division.

53. The method of claim 51, wherein said podocytes that are substantially incapable of proliferation comprise podocytes that retain the capacity to proliferate.

54. The method of claim 47, wherein application of said mechanical strain comprises stretching said membrane.

55. The method of claim 47, further comprising contacting said first population of cells with a serum-free podocyte induction medium comprising
- (i) activin A,
- (ii) bone morphogenetic protein (BMP),
- (iii) an inhibitor of glycogen synthase kinase 3 (GSK-3) or an activator of Wnt signaling pathway,
- (iv) vascular endothelial growth factor (VEGF), and
- (v) retinoic acid.

56. A method of generating a population of podocytes comprising contacting, on a surface coated with at least one extracellular matrix protein, a first population of cells comprising intermediate mesoderm cells with a podocyte induction medium comprising
- (i) activin A,
- (ii) bone morphogenetic protein (BMP),
- (iii) an inhibitor of glycogen synthase kinase 3 (GSK-3) or an activator of Wnt signaling pathway,
- (iv) vascular endothelial growth factor (VEGF), and
- (iv) retinoic acid, wherein the podocyte induction medium is serum-free, wherein said contacting is under conditions that produce a second population of cells that comprises an increased percentage of podocytes, as compared to a percentage of podocytes comprised in a population of cells comprising intermediate mesoderm cells that are not contacted with the podocyte induction medium, and said second population of cells comprises at least about 90% podocytes, and wherein said podocytes are substantially negative for Paired Box 2 (PAX-2) protein.

57. The method of claim 56, wherein said surface coated with at least one extracellular matrix protein is comprised in a microfluidic device.

58. The method of claim 56, further comprising exposing said first population of cells or said second population of cells to one or more of mechanical strain and shear stress.

59. The method of claim 56, wherein said podocytes comprised in said second population of cells exhibit an increased uptake of exogenous albumin compared to immortalized podocytes.

* * * * *